(12) United States Patent
Yin et al.

(10) Patent No.: US 12,018,306 B2
(45) Date of Patent: Jun. 25, 2024

(54) **METHOD FOR CHEMICALLY SYNTHESIZING *HELICOBACTER PYLORI* CORE LIPOPOLYSACCHARIDE OLIGOSACCHARIDE ANTIGEN CARBOHYDRATE CHAIN**

(71) Applicant: Jiangnan University, Wuxi (CN)

(72) Inventors: Jian Yin, Wuxi (CN); Jing Hu, Wuxi (CN); Xiaopeng Zou, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 18/373,423

(22) Filed: Sep. 27, 2023

(65) Prior Publication Data
US 2024/0068001 A1    Feb. 29, 2024

Related U.S. Application Data

(63) Continuation of application No. PCT/CN2023/083341, filed on Mar. 23, 2023.

(30) Foreign Application Priority Data

May 9, 2022   (CN) .......................... 202210498276.1

(51) Int. Cl.
*C12P 19/04*   (2006.01)
(52) U.S. Cl.
CPC .................................. *C12P 19/04* (2013.01)
(58) Field of Classification Search
CPC ...................................................... C12P 19/04
USPC ...................................................... 536/18.5
See application file for complete search history.

(56) References Cited

FOREIGN PATENT DOCUMENTS

CN       114874345 A     8/2022

OTHER PUBLICATIONS

Xiaopeng Zou, "Total synthesis of core oligosaccharide antigens of Helicobacter pylori lipopolysaccharide" China Doctoral Dissertation Full Text Database Medical and Health Science and Technology Series, V01, pp. 1-166, Jun. 19, 2020.
Xiaopeng Zou, et al., Synergistic Glycosylation as Key to the Chemical Synthesis of an Outer Core Octasaccharide of Helicobacter pylori , Chem Eur. J., vol. 24, pp. 2868-2872 (2018).
Chemical Synthesis of the Highly Sterically Hindered Core Undecasaccharide of Helicobacter pylori Lipopolysaccharide for Antigenicity Evaluation with Human Serum , Xiaopeng Zou, et al., J. Am. Chem. Soc., vol. 144, pp. 14535-14547 (Published: Aug. 8, 2022).

*Primary Examiner* — Yih-Horng Shiao
(74) *Attorney, Agent, or Firm* — IPRO, PLLC

(57) ABSTRACT

The disclosure discloses a method for chemically synthesizing a *Helicobacter pylori* core lipopolysaccharide oligosaccharide antigen carbohydrate chain, and belongs to the technical field of carbohydrate chemistry. The disclosure uses D-glucose, D-galactose and D-mannose as starting materials, which undergo a series of protection and deprotection reactions to prepare eight monosaccharide blocks. The eight monosaccharide block compounds as shown in formulas 2 to 9 undergo glycosylation reactions under catalysis of corresponding activating reagents, to prepare *H. pylori* lipopolysaccharide core oligosaccharide antigen fragments as shown in formula 1. The disclosure further combines the synthesized oligosaccharide fragments with a chip to make a carbohydrate chip, screens the optimal antigen fragments using patient serum, or combines the synthesized oligosaccharide fragments with carrier proteins to make glycoconjugates.

6 Claims, 17 Drawing Sheets

METHOD FOR CHEMICALLY SYNTHESIZING *HELICOBACTER PYLORI* CORE LIPOPOLYSACCHARIDE OLIGOSACCHARIDE ANTIGEN CARBOHYDRATE CHAIN

TECHNICAL FIELD

The disclosure relates to a method for chemically synthesizing a *Helicobacter pylori* core lipopolysaccharide oligosaccharide antigen carbohydrate chain, and belongs to the technical field of carbohydrate chemistry.

BACKGROUND

*Helicobacter pylori* is a spiral shaped, flagellated, gram-negative bacterium that infects over 50% of people worldwide. Infection with *H. pylori* can cause gastritis, gastric ulcers, duodenal ulcers, and even gastric cancer, with over 60% of gastric cancer being considered related to infection with *H. pylori*. In 2021, the US Department of Health and Human Services listed *H. pylori* as a clear carcinogenic factor in the 15$^{th}$ Report on Carcinogens. At present, the main methods for treating *H. pylori* are a triple therapy and a quadruple therapy, which combine antibiotics and proton pump inhibitors. Due to the increasing number of drug-resistant bacteria, the efficiency of using antibiotics to remove *H. pylori* infection is gradually decreasing. The World Health Organization listed *H. pylori* as one of twelve infectious bacteria that urgently need new antibiotics in 2017. Therefore, the development of *H. pylori* vaccines has always been a research hotspot.

Lipopolysaccharides, which are specifically expressed on the surface of pathogenic bacteria, are important targets for the development of carbohydrate vaccines. There have been multiple marketed glycoconjugate vaccines for disease prevention and treatment, e.g., *Streptococcus pneumoniae* 13-valent glycoconjugate vaccines, meningitis glycoconjugate vaccines, and *Salmonella* conjugate vaccines. Surface oligosaccharide/polysaccharide antigens extracted from pathogenic bacteria cannot guarantee purity and homogeneity of structures, and important antigen epitopes may be lost during the extraction process, which limits the development and application of glycoconjugate vaccines.

Lipopolysaccharide (LPS) is the main antigen component on the surface of *H. pylori* cells, and is mainly composed of O-chain polysaccharides, core structures and lipid A. The core structure of *H. pylori* is composed of an outer core octasaccharide structure and a phosphorylated inner core trisaccharide structure, which are shown below:

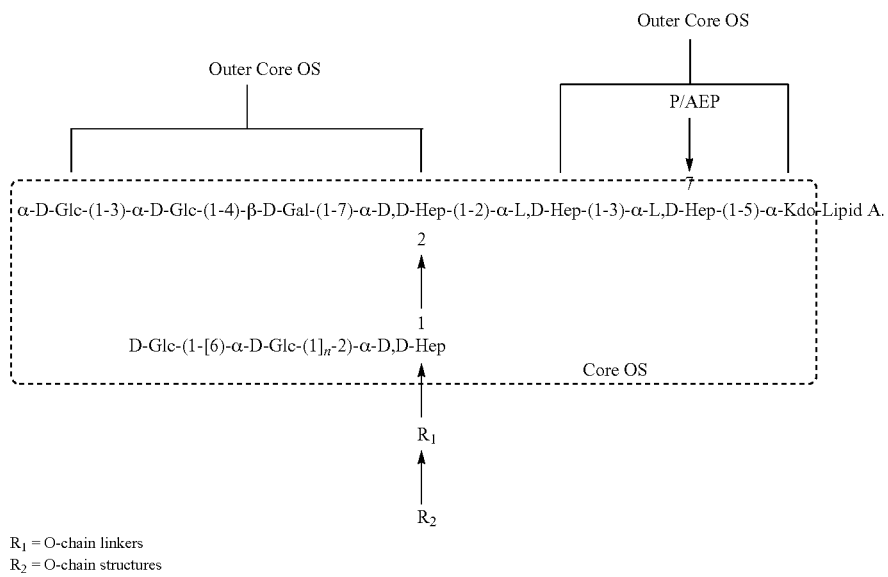

$R_1$ = O-chain linkers
$R_2$ = O-chain structures

*H. pylori* lipopolysaccharide core oligosaccharide is considered as a good immune target due to its structural specificity and structural conservation among different serotype strains. Mario's research team and colleagues found through research that glycoconjugates prepared from extracted *H. pylori* O1, O2, and O5 lipopolysaccharides and carrier proteins produced strong IgG antibodies in mice, and these antibodies could all recognize core oligosaccharide structures. Synthesizing structurally uniform and clear *H. pylori* core oligosaccharide antigens through chemical methods are of great significance for determination of *H. pylori* glycoantigen epitopes and development of *H. pylori* glycoconjugate vaccines.

SUMMARY

Technical problem: The technical problem to be solved by the disclosure is rapid and efficient preparation of a *Helicobacter pylori* lipopolysaccharide core oligosaccharide antigen carbohydrate chain through chemical methods.

Technical solution: The disclosure uses easily available glucose, galactose and mannose as starting materials, which undergo a series of chemical reactions to prepare eight monosaccharide blocks. These monosaccharide blocks undergo a series of glycosylation reactions based on activation of corresponding activating reagents to prepare *H. pylori* core oligosaccharide antigen fragments under a neighboring group participation effect, a solvent effect, a temperature effect, and the like. The prepared oligosaccharide fragments are deprotected and then combined with a chip through a connecting arm to prepare a carbohydrate chip for detecting the optimal carbohydrate antigen epitope. The prepared carbohydrate antigen fragments are combined with carrier proteins to prepare glycoconjugates, and further the immune activity of the glycoconjugates is studied to provide a theoretical basis for the development of *H. pylori* glycoconjugate vaccines.

A first objective of the disclosure is to provide a method for chemically synthesizing an *H. pylori* lipopolysaccharide core oligosaccharide antigen. The method involves synthesizing *H. pylori* core oligosaccharide antigen fragments using eight monosaccharide blocks, which are compounds 2-9 with the structures as follows:

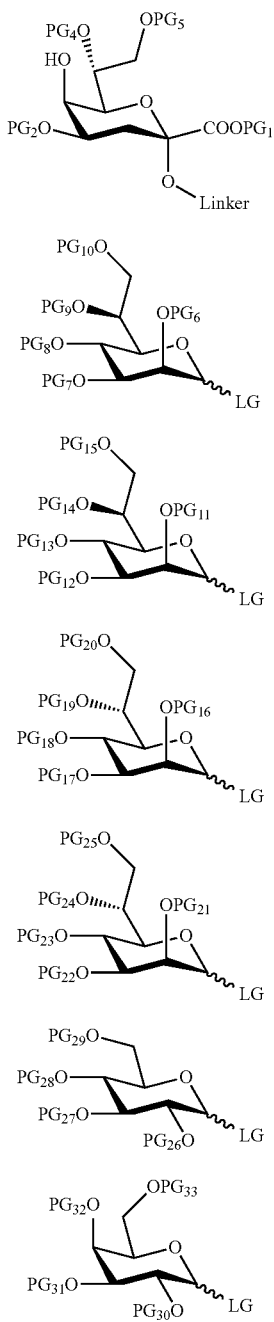

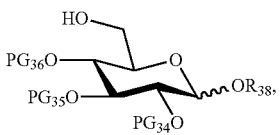

where $PG_2$, $PG_6$, $PG_8$, $PG_9$, $PG_{12}$, $PG_{13}$, $PG_{14}$, $PG_{15}$, $PG_{17}$, $PG_{18}$, $PG_{19}$, $PG_{22}$, $PG_{23}$, $PG_{25}$, $PG_{26}$, $PG_{28}$, $PG_{29}$, $PG_{30}$, $PG_{34}$, $PG_{35}$, and $PG_{36}$ are hydrogen (H), benzyl (Bn) and derivatives thereof, 2-naphthylmethyl (Nap) and derivatives thereof, or tert-butyldimethylsilyl (TBS), tert-butyldiphenylsilyl (TBDPS), or triethylsilyl (TES);

$PG_1$ is any of hydrogen, methyl (Me), ethyl (Et), tert-butyl (t-Bu), or benzyl (Bn);

$PG_4$ and $PG_5$ are any of propylidene, benzylidene, benzyl (Bn) and derivatives thereof, 2-naphthylmethyl (Nap) and derivatives thereof, or tert-butyldimethylsilyl (TBS), tert-butyldiphenylsilyl (TBDPS), or triethylsilyl (TES);

$PG_7$, $PG_{11}$, $PG_{16}$, $PG_{21}$, $PG_{27}$, $PG_{32}$, $PG_{33}$, and $RG_{38}$ are acetyl (Ac), chloroacetyl (ClAc), benzoyl (Bz), pivaloyl, acetylpropionyl (Lev), 9-pentamethoxycarbonyl (Fmoc), 2-naphthylmethyl (Nap) and derivatives thereof, and 2-p-methoxybenzyl (PMB);

$PG_{10}$ is one of acetyl (Ac), chloroacetyl (ClAc), benzoyl (Bz), pivaloyl, acetylpropionyl (Lev), or 9-pentamethoxycarbonyl (Fmoc);

a Linker is $-(CH_2)_n-N-Y_1Y_2$ or $-(CH_2)_n-S-Y_1$, where n=1-10, and $Y_1$ and $Y_2$ are any of hydrogen, acyl (acetyl and phthaloyl), benzyl and derivatives thereof, 2-naphthylmethyl, or benzylmethoxycarbonyl (Cbz); and a leaving group LG is selected from any of trichloroacetimidate ($CNHCCl_3$), N-phenyltrifluoroacetimidate glycoside ($CNPhCCl_3$), methylthio (SMe), ethylthio (SEt), phenylthiol (SPh), p-tolylthio (STol), dibenzyl phosphate, fluoro (F), chloro (Cl), bromo (Br), and iodo (I);

In one embodiment of the disclosure, the construction of a glycosidic bond is prepared by coupling a glycosyl donor with a glycosyl receptor under activation of an activating reagent.

In one embodiment of the disclosure, the activating reagent is one or more of TMSOTf, NIS-TMSOTf, NIS-TfOH, and NIS-AgOTf.

In one embodiment of the disclosure, the solvent is one or more of anhydrous dichloromethane, ether, toluene, methanol, tetrahydrofuran, N,N-dimethylformamide, or water.

In one embodiment of the disclosure, the reactions are all conducted by stirring under the protection of argon gas.

In one embodiment of the disclosure, the concentration of the glycosylation reactions is 0.02-0.05 M.

In one embodiment of the disclosure, $PG_{20}$ is monochloroacetyl; $PG_{24}$ is benzyl; and $PG_{31}$ is benzyl.

In one embodiment of the disclosure, a saccharide block donor 3 and a saccharide block receptor 2 undergo a glycosylation reaction to prepare a disaccharide compound 11 by the following synthesis route:

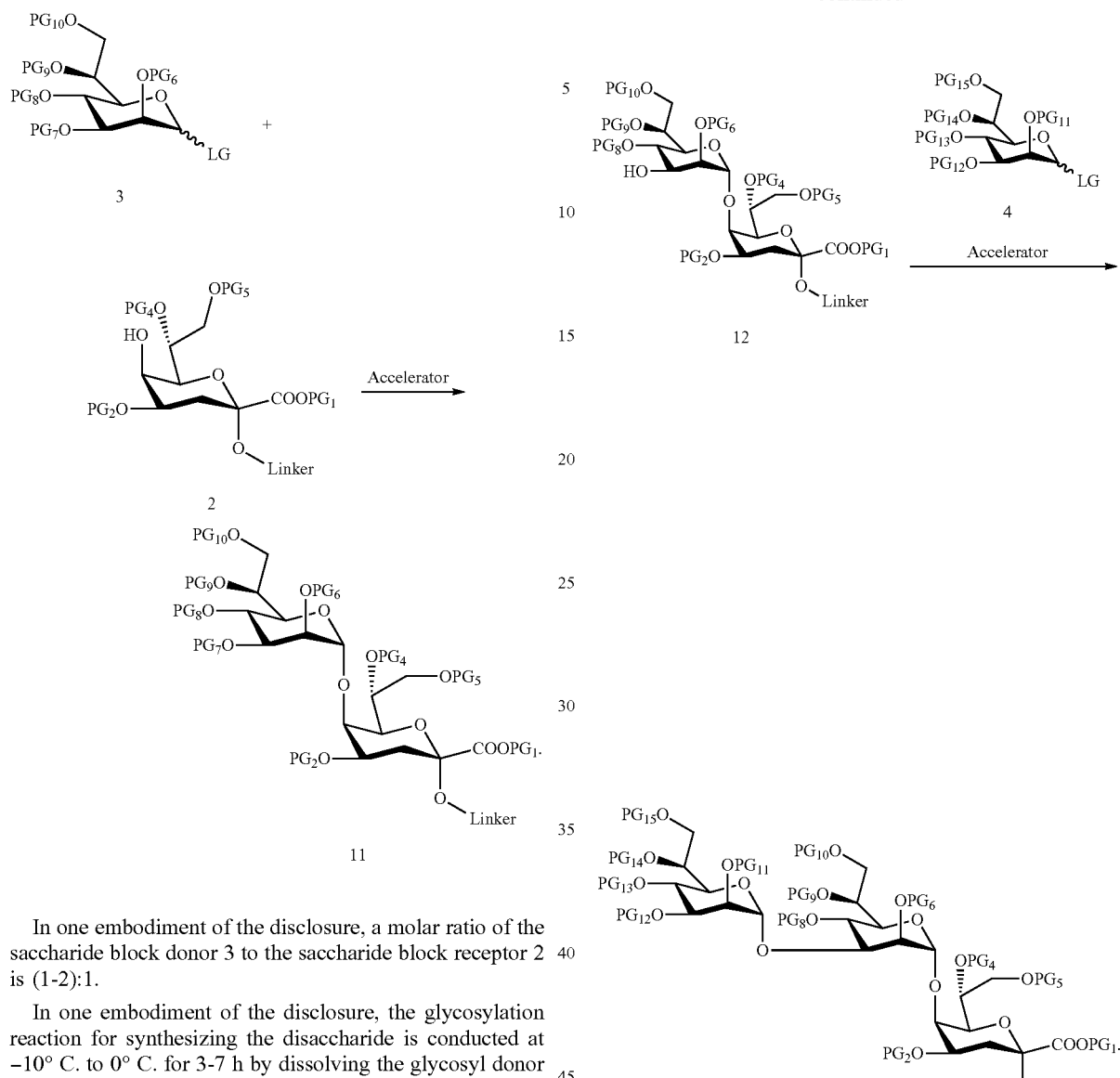

In one embodiment of the disclosure, a molar ratio of the saccharide block donor 3 to the saccharide block receptor 2 is (1-2):1.

In one embodiment of the disclosure, the glycosylation reaction for synthesizing the disaccharide is conducted at −10° C. to 0° C. for 3-7 h by dissolving the glycosyl donor and the glycosyl receptor in dichloromethane, and adding molecular sieves and 0.1-0.3 equivalent (molar equivalent compared to the donor) of an activating reagent.

In one embodiment of the disclosure, the synthesis route of the trisaccharide is as follows:

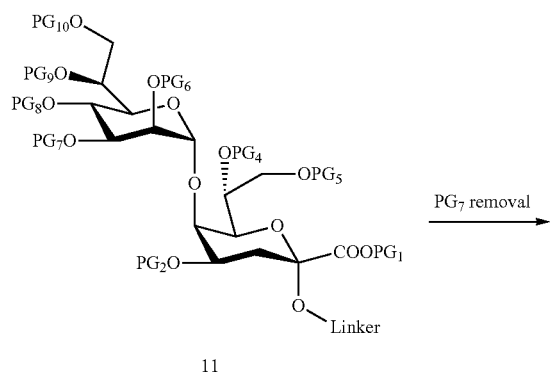

In one embodiment of the disclosure, the specific method for synthesizing the trisaccharide includes the steps: the disaccharide 11 selectively removes a $PG_7$ protecting group to prepare disaccharide 12; and the disaccharide 12 and a saccharide block donor 4 undergo a glycosylation reaction under an accelerator to prepare a trisaccharide compound 13.

In one embodiment of the disclosure, a molar ratio of the saccharide block donor 4 to the disaccharide 12 is (1-2):1.

In one embodiment of the disclosure, the glycosylation reaction for synthesizing the trisaccharide is conducted at −10° C. to 0° C. for 3-7 h by dissolving the glycosyl donor and the glycosyl receptor in dichloromethane, and adding molecular sieves and 0.1-0.3 equivalent (molar equivalent compared to the donor) of an activating reagent.

In one embodiment of the disclosure, the synthesis route of the tetrasaccharide is as follows:

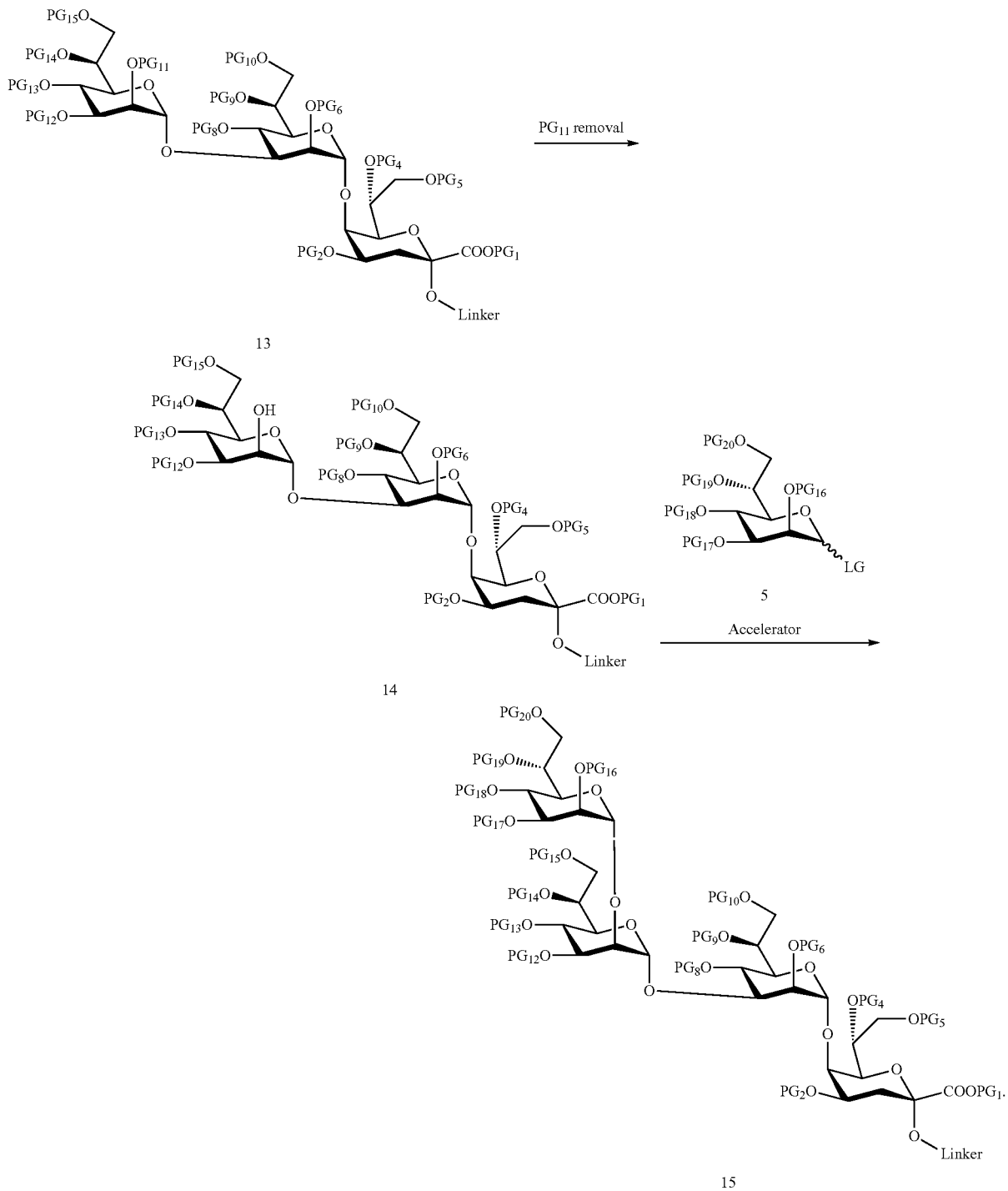

In one embodiment of the disclosure, the specific method for synthesizing the tetrasaccharide includes the steps: the trisaccharide 13 selectively removes a $PG_{11}$ protecting group to prepare trisaccharide 14; and the trisaccharide 14 and a saccharide block donor 5 undergo a glycosylation reaction under an accelerator to prepare a tetrasaccharide compound 15.

In one embodiment of the disclosure, a molar ratio of the donor 5 to the trisaccharide 14 is (1-2):1.

In one embodiment of the disclosure, the glycosylation reaction for synthesizing the tetrasaccharide is conducted at −20° C. to 0° C. for 3-7 h by dissolving the glycosyl donor and the glycosyl receptor in dichloromethane, and adding molecular sieves and 0.1-0.3 equivalent (molar equivalent compared to the donor) of an activating reagent.
In one embodiment of the disclosure, the synthesis route of the pentasaccharide is as follows:
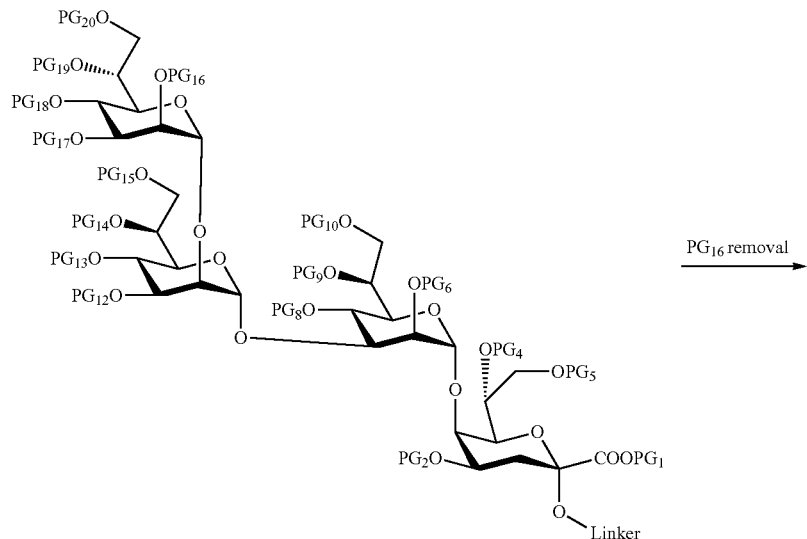
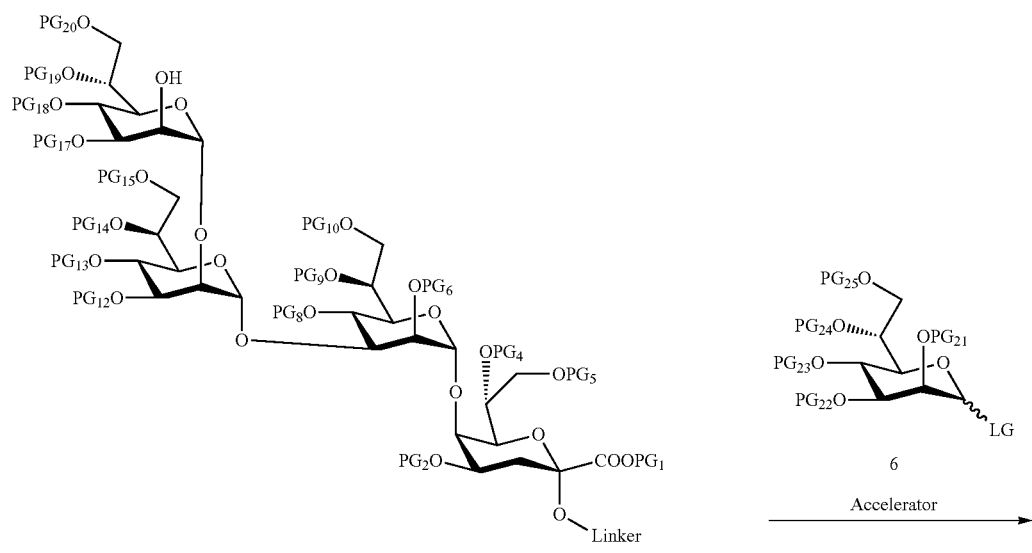
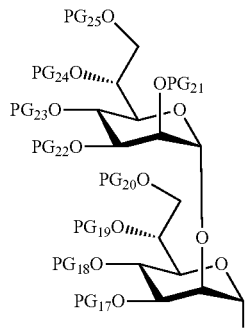

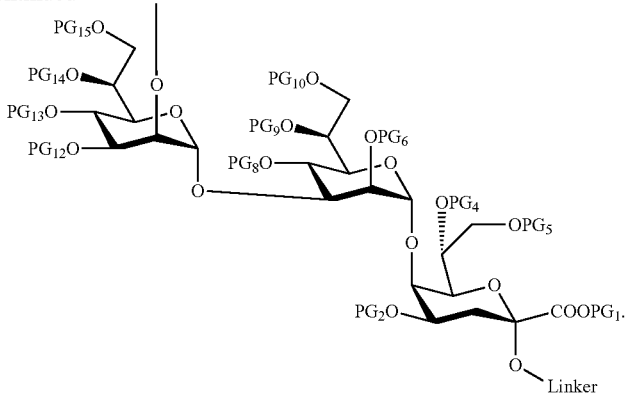

17

In one embodiment of the disclosure, the specific method for synthesizing the pentasaccharide includes the steps: the tetrasaccharide 15 selectively removes a $PG_{16}$ protecting group to prepare tetrasaccharide 16; and the tetrasaccharide 16 and a saccharide block donor 6 undergo a glycosylation reaction under an accelerator to prepare a pentasaccharide compound 17.

In one embodiment of the disclosure, a molar ratio of the saccharide block donor 6 to the tetrasaccharide 16 is (1-2):1.

In one embodiment of the disclosure, the glycosylation reaction for synthesizing the pentasaccharide is conducted at −20° C. to 0° C. for 3-7 h by dissolving the glycosyl donor and the glycosyl receptor in dichloromethane, and adding molecular sieves and 0.1-0.3 equivalent (molar equivalent compared to the donor) of an activating reagent.

In one embodiment of the disclosure, the synthesis route of the trisaccharide module 21 is as follows:

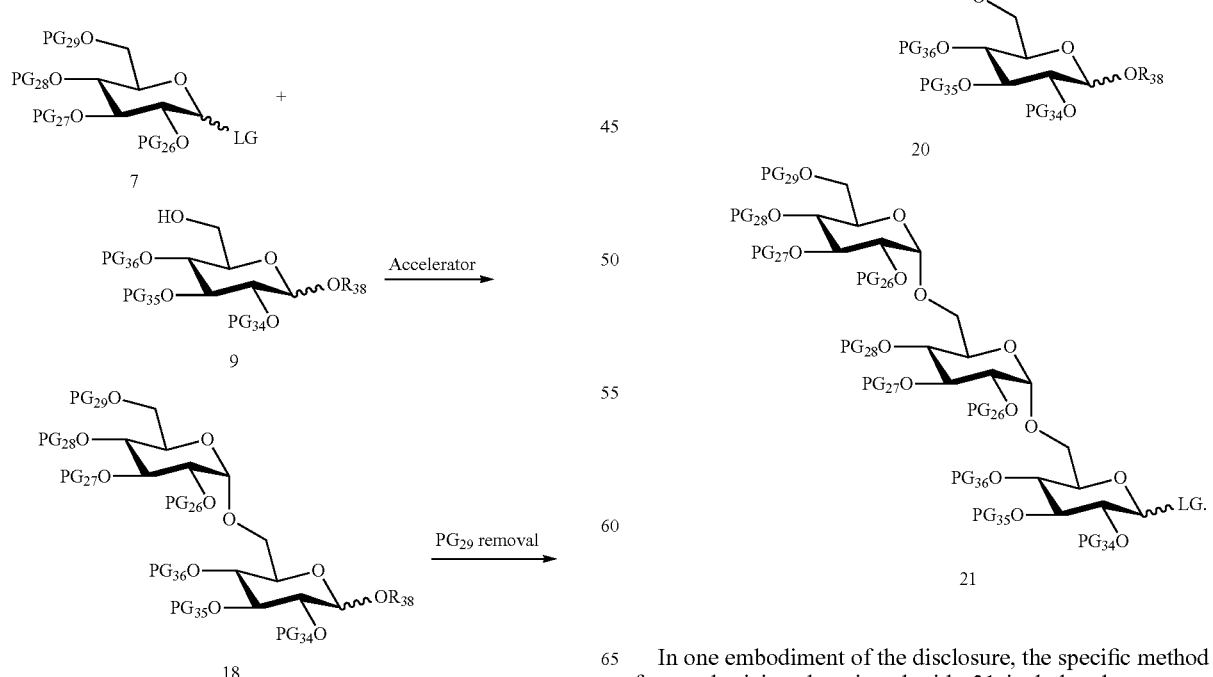

In one embodiment of the disclosure, the specific method for synthesizing the trisaccharide 21 includes the steps: a saccharide block donor 7 and a saccharide block receptor 9 undergo a glycosylation reaction under the catalysis of an accelerator to prepare disaccharide 18; the compound 18 selectively removes $PG_{29}$ to prepare disaccharide 19, and the compound 19 and a saccharide block donor 7 further undergo a glycosylation reaction under the catalysis of an accelerator to prepare a trisaccharide module 20; and after $PG_{38}$ is removed from the terminal of the trisaccharide module 20, the terminal hydroxyl reacts with trichloroacetonitrile or phenyltrifluoroacetyl chloride under an alkaline catalyst to prepare the trisaccharide 21 that can be used for a glycosylation reaction.

In one embodiment of the disclosure, a molar ratio of the saccharide block donor to the receptor in synthesis of the disaccharide is (1-2):1; and a molar ratio of the saccharide block donor to the receptor during synthesis of the trisaccharide is (1-2):1.

In one embodiment of the disclosure, the glycosylation reaction for synthesizing the trisaccharide is conducted at 0° C. to room temperature for 3-7 h by dissolving the glycosyl donor and the glycosyl receptor in dichloromethane and ether (1:2), and adding molecular sieves and 0.1-0.3 equivalent (molar equivalent compared to the donor) of an activating reagent.

In one embodiment of the disclosure, the synthesis route of the octasaccharide is as follows:

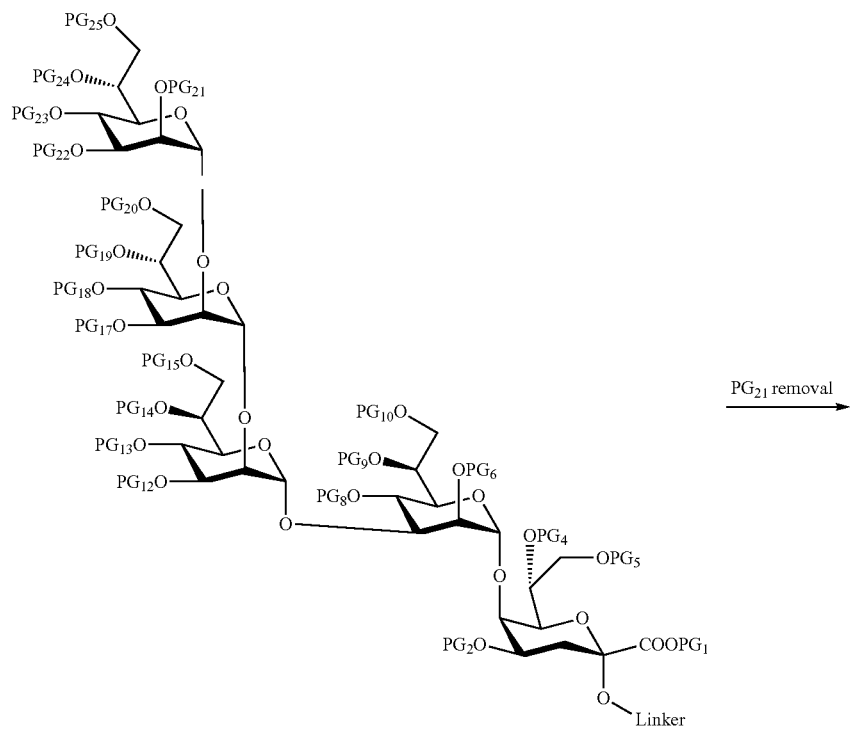

-continued
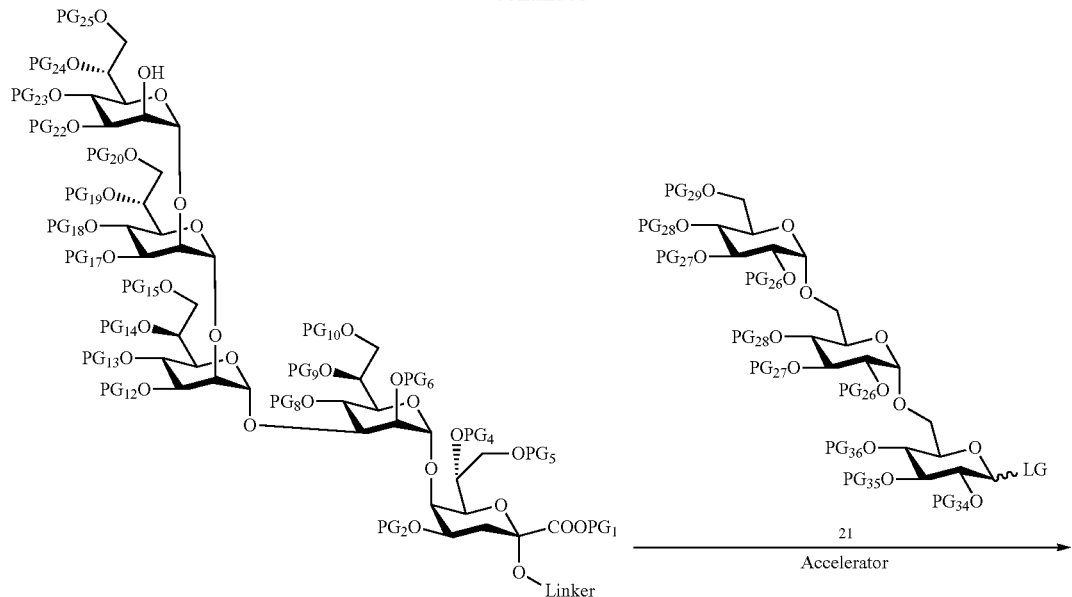
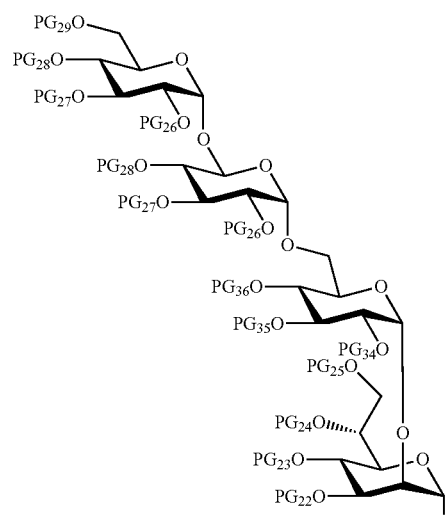

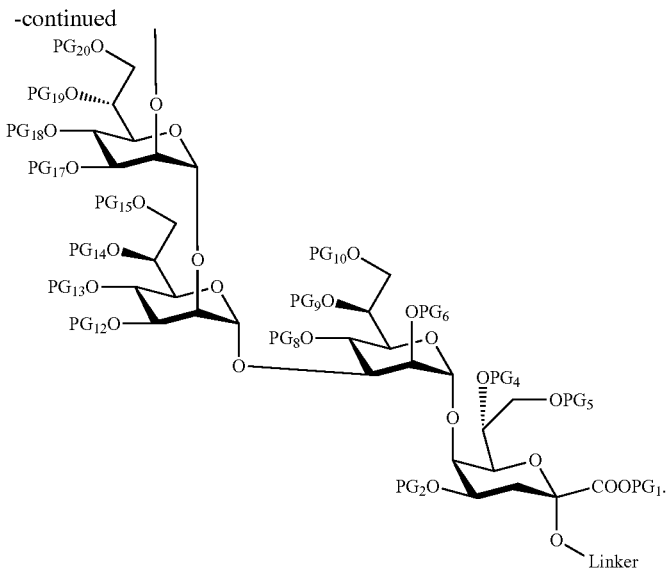

23

In one embodiment of the disclosure, the specific method for synthesizing the octasaccharide includes the steps: the pentasaccharide 17 selectively removes a $PG_{21}$ protective group to prepare pentasaccharide 22; and the pentasaccharide 22 and a trisaccharide donor 21 undergo a glycosylation reaction under an accelerator to prepare an octasaccharide compound 23.

In one embodiment of the disclosure, a molar ratio of the saccharide block donor 21 to the receptor 22 is (1-2):1.

In one embodiment of the disclosure, the glycosylation reaction for synthesizing the octasaccharide is conducted at 0° C. to room temperature for 3-7 h by dissolving the glycosyl donor and the glycosyl receptor in dichloromethane and ether (1:3), and adding molecular sieves and 0.1-0.3 equivalent (molar equivalent compared to the donor) of an activating reagent.

In one embodiment of the disclosure, the synthesis route of the disaccharide module 26 is as follows:

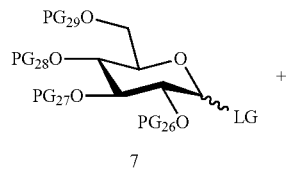

7

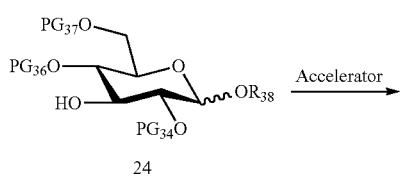

24

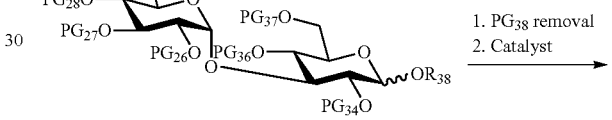

25

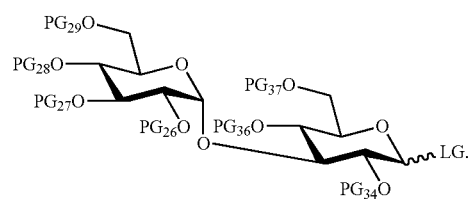

26

In one embodiment of the disclosure, the specific method for synthesizing the disaccharide 26 includes the steps: a glycosyl donor 7 and a receptor 24 undergo a glycosylation reaction under the catalysis of an accelerator to prepare disaccharide 25; and the compound 25 selectively removes $PG_{38}$, and the terminal hydroxyl reacts with trichloroacetonitrile or phenyltrifluoroacetyl chloride under an alkaline catalyst to prepare the disaccharide 26 that can be used for a glycosylation reaction.

In one embodiment of the disclosure, a molar ratio of the saccharide block donor to the receptor is (1-2):1.

In one embodiment of the disclosure, the glycosylation reaction for synthesizing the disaccharide is conducted at 0° C. to room temperature for 3-7 h by dissolving the glycosyl donor and the glycosyl receptor in dichloromethane and ether (1:2), and adding molecular sieves and thiophene.

In one embodiment of the disclosure, the synthesis route of the undecasaccharide is as follows:
$PG_{20}$ removal →
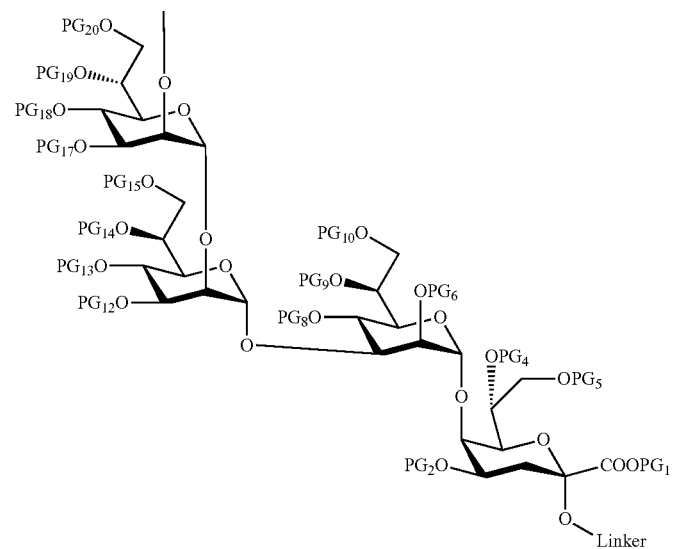
23
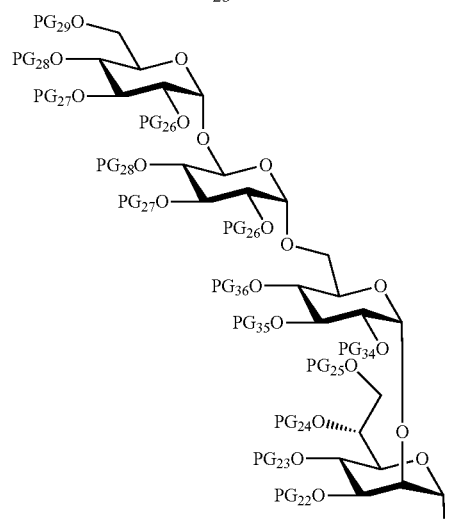

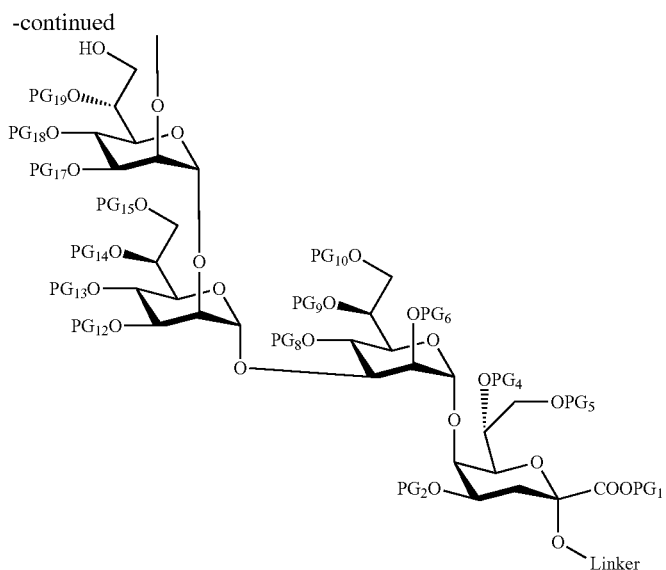
27
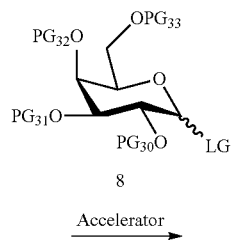
8
Accelerator →
PG$_{32}$ removal →

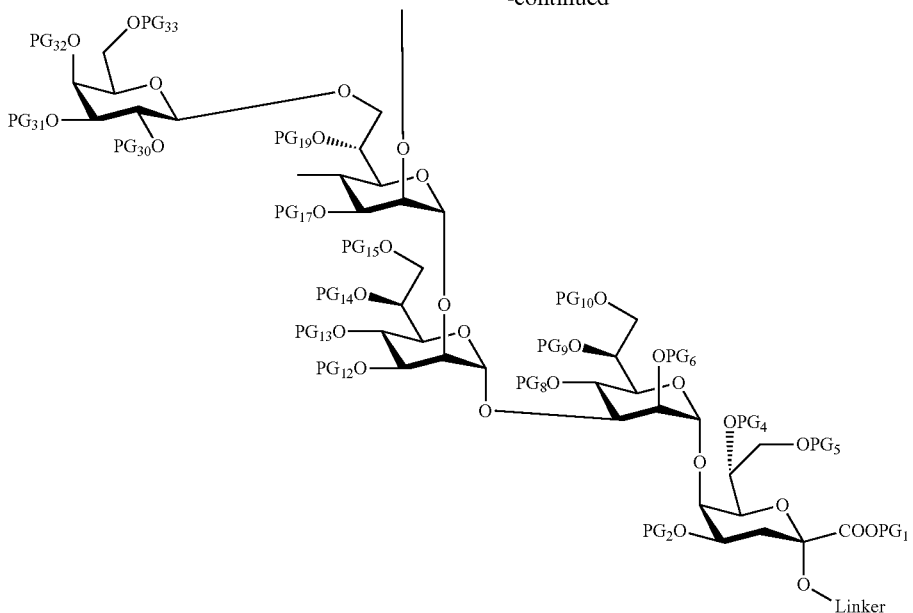
28
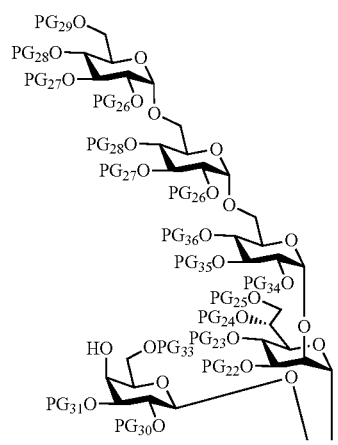
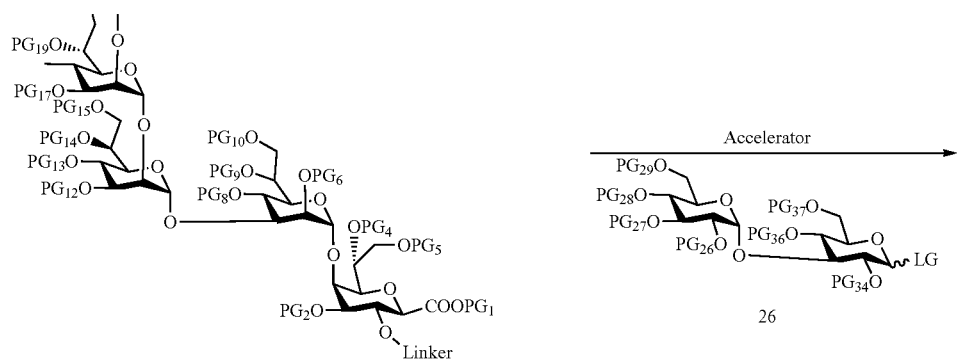
29

-continued

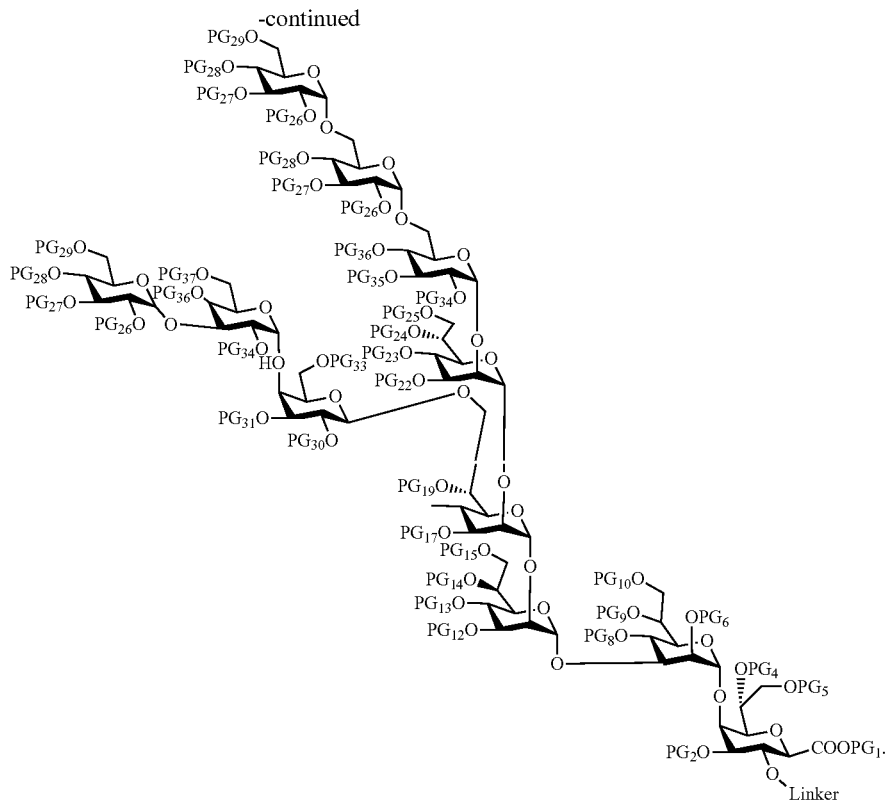

30

In one embodiment of the disclosure, the specific method for synthesizing the undecasaccharide 30 includes the steps: the octasaccharide 23 selectively removes a $PG_{20}$ protective group to prepare octasaccharide 27; the octasaccharide 27 and a monosaccharide donor 8 undergo a glycosylation reaction under an accelerator to prepare a nonasaccharide compound 28; and the nonasaccharide 28 selectively removes the protective group $PG_{32}$ to prepare a nonasaccharide receptor 29, and the nonasaccharide receptor and a glycosyl donor 26 undergo a glycosylation reaction under an accelerator to prepare the undecasaccharide 30.

In one embodiment of the disclosure, a molar ratio of the saccharide block donor to the receptor is (2-5):1.

In one embodiment of the disclosure, the glycosylation reaction for synthesizing the undecasaccharide 30 is conducted at 0° C. to room temperature for 3-7 h by dissolving the glycosyl donor and the glycosyl receptor in dichloromethane and ether (1:3), and adding molecular sieves and 0.1-0.3 equivalent (molar equivalent compared to the donor) of an activating reagent.

In one embodiment of the disclosure, the undecasaccharide 30 removes an acyl protecting group under an alkaline condition and an aromatic protecting group under a palladium on carbon/hydrogen condition to complete deprotection, resulting in completely deprotected undecasaccharide 1;

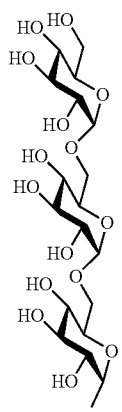

-continued

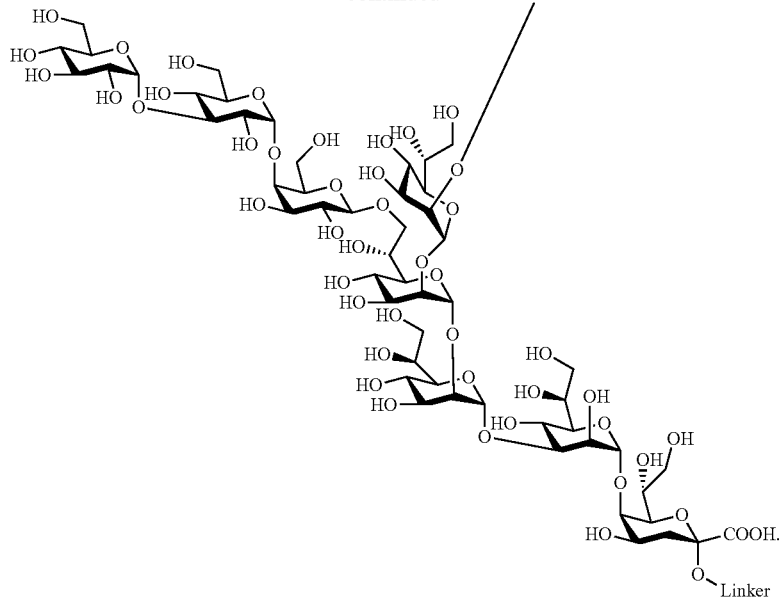

In one embodiment of the disclosure, the hydrogen gas pressure used for the deprotection is 4 atmospheres, and the solvents used include mixed solvents of ethyl acetate, methanol, water and acetic acid.

Based on the aforementioned method, the disclosure synthesizes an *H. pylori* core antigen oligosaccharide compound assembled with a linker, with the structural formula shown in formula I.

The disclosure further provides a method for preparing a carbohydrate antigen fragment chip for screening *H. pylori*, wherein a core oligosaccharide structure used is covalently bound to the chip through a linker, and the general formula can be expressed as carbohydrate-Linker-chip.

The disclosure further provides a method for preparing an *H. pylori* glycoprotein conjugate, wherein a core oligosaccharide molecule is connected to a carrier through a linker to prepare the glycoprotein conjugate, and the general formula can be expressed as carbohydrate-Linker-carrier protein. The carrier protein can be one of non-toxic mutant protein of diphtheria toxin (CRM197), keyhole limpet hemocyanin (KLH), bovine serum albumin (BSA), meningococcal outer membrane protein complex (OMPC), tetanus toxoid (TT), or diphtheria toxoid (DT).

The disclosure further provides use of the aforementioned *H. pylori* lipopolysaccharide core oligosaccharide antigen, carbohydrate chip, and glycoconjugate in preparation of *H. pylori* vaccines.

In one embodiment of the disclosure, a method for preparing the carbohydrate chip includes the step: oligosaccharide with an amino linker is covalently bound to the chip with a carboxyl-modified surface, and further bound to antibody serum.

In one embodiment of the disclosure, a method for preparing the glycoprotein conjugate includes the step: an amide bond is formed between oligosaccharide with an amino linker and the side chain carboxyl of aspartic acid or glutamic acid in a carrier protein.

Beneficial Effects

The disclosure involves preparing the core lipopolysaccharide antigen fragment undecasaccharide conservative to *H. pylori* based on chemical methods. The disclosure found an efficient route and method for preparing a core oligosaccharide antigen through a preferred protecting group strategy, a temperature effect, a solvent effect, and a preferred glycosyl assembly sequence. The reducing end of the chemically synthesized core oligosaccharide antigen is assembled with the amino linker, which can bind to a chip or a carrier protein, providing a theoretical basis for further development of *H. pylori* glycoconjugate vaccines.

DETAILED DESCRIPTION

Embodiments of the disclosure will be described in detail below with reference to the examples, but those skilled in the art will understand that the following examples are intended to illustrate the disclosure and are not to be considered as limiting the scope of the disclosure. If specific conditions are not indicated in the examples, they are carried out in accordance with conventional conditions or conditions suggested by manufacturers. Reagents or instruments used without manufacturers indicated are commercially available conventional products.

A yield calculation method in the disclosure is "product (mol)/reaction raw material (mol)*100%". The methods for identifying the structures of compounds in the disclosure include nuclear magnetic resonance spectroscopy (400 M, 600 M, 700 M), high-resolution mass spectrometry, and polarimetry. The results are listed in the specific synthesis process of each compound.

Example 1

Figure 1:
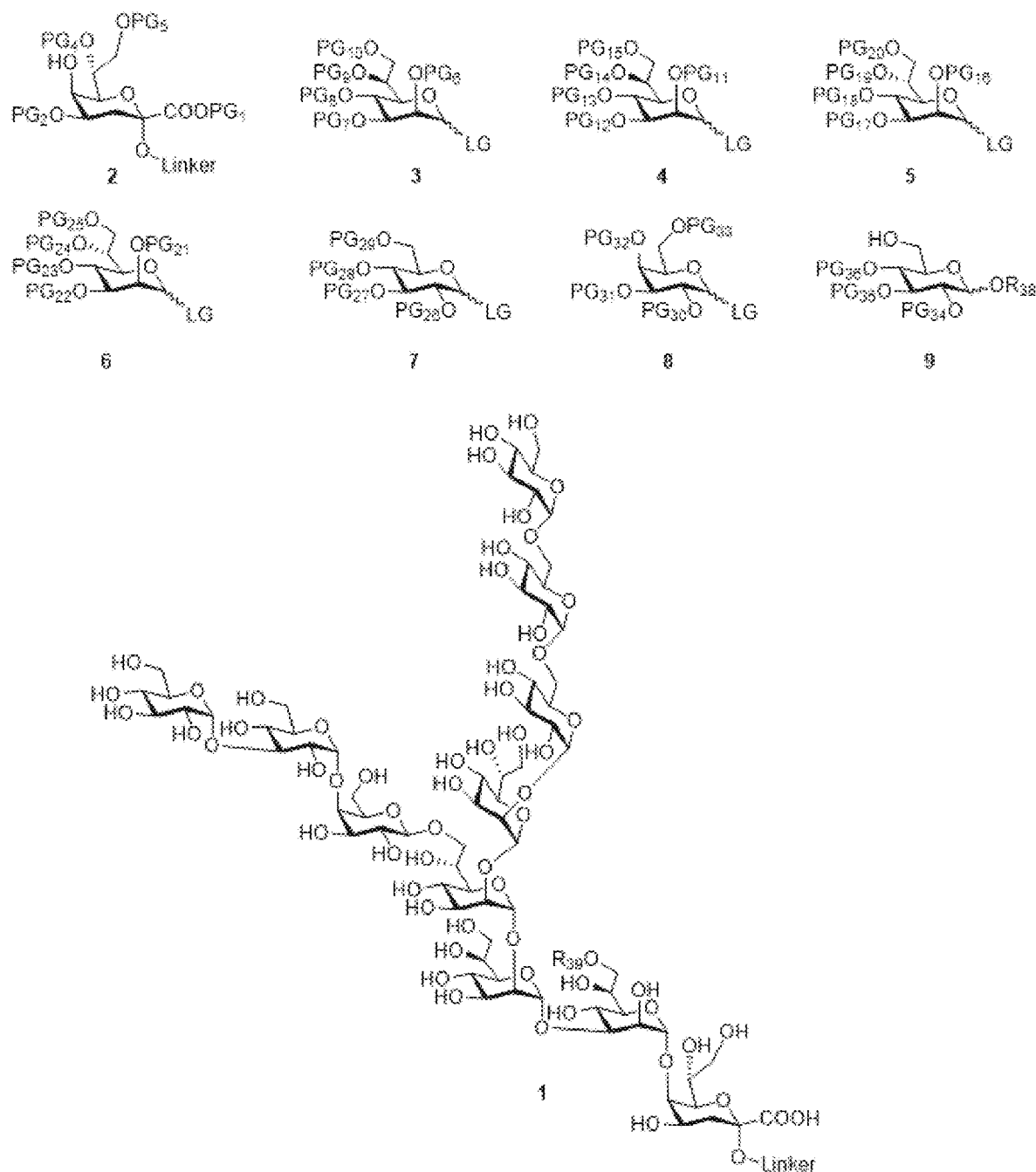
FIG. 1 shows the structural formulas of saccharide blocks required for synthesizing the *Helicobacter pylori* core oligosaccharide antigen and a target undecasaccharide.
Figure 2:
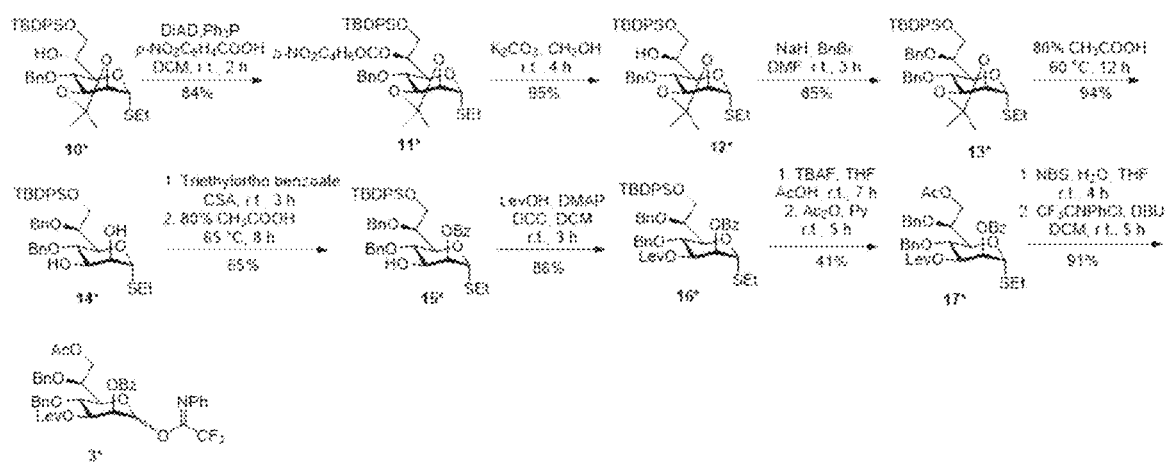
FIG. 2 shows the synthesis route of a saccharide block 3*.

A saccharide block 3* was synthesized as shown in FIG. 2:

Starting from a reported D,D-heptose compound 10*, by conducting configuration transformation through a Mitsunobu reaction, D,D-heptose 10* was converted into L,D-heptose 11*, with a yield of 84%. P-nitrobenzoyl was removed under a weakly alkaline potassium carbonate condition to prepare a compound 12*, with a yield of 95%. The compound 12* underwent a benzylation reaction under benzyl bromide and sodium hydride to prepare a compound 13*, with a yield of 85%. O2,3-propylidene was removed from the compound 13* by 80% acetic acid treatment to prepare a compound 14*, with a yield of 94%. Using camphor sulfonic acid (CSA), triethyl orthobenzoate, and 80% acetic acid, benzoyl was selectively introduced at C2 of the compound 14* for protection to prepare a compound 15*, with a yield of 65%. Then, the C3 hydroxyl was protected with acetylpropionyl to prepare a compound 16*, with a yield of 86%. C7 TBDPS was removed from the compound 16*, and then acetylation is conducted to prepare a compound 17*, with a yield of 41%. Through desulfurization and trifluoroacetylimine esterification, thioglucoside 17* was converted into a glycosyl donor 3*, with a two-step yield of 92%.

Specific experimental operations and steps:

Compound 11*: The compound 10* (2.5 g, 4.0 mmol) was dissolved in THF (50.0 mL). Triphenylphosphine (2.1 g, 8.0 mmol), p-nitrobenzoic acid (1.33 g, 8.0 mmol), and diisopropyl azodicarboxylate (DIAD) (1.5 mL, 8.0 mmol) were added at room temperature, and the reaction solution was stirred at room temperature for 2 h. After the reaction raw materials completely disappeared, the mixture was concentrated under reduced pressure and separated and purified using a silica gel chromatography column (petroleum ether/ethyl acetate, 20:1) to prepare the compound 11* (2.5 g, 3.36 mmol, 84%). $^1$H NMR (400 MHz, CHCl$_3$) δ8.47-8.02 (m, 3H, Ar), 7.77-7.04 (m, 16H, Ar), 5.74 (ddd, J=7.6, 6.3, 1.9 Hz, 1H, H-6), 5.57 (s, 1H, H-1), 4.80 (d, J=11.0 Hz, 1H, ArCH$_2$), 4.43 (d, J=11.0 Hz, 1H, CH$_2$), 4.37-4.34 (m, 1H, H-5), 4.33 (m, 1H, H-3), 4.20 (dd, J=5.6, 1.0 Hz, 1H, H-2), 3.98 (dd, J=10.3, 7.3 Hz, 1H, H-7), 3.84 (dd, J=10.3, 6.2 Hz, 1H, H-7'), 3.51 (dd, J=10.2, 6.8 Hz, 1H), H-4, 2.61-2.32 (m, 2H, SCH$_2$CH$_3$), 1.40 (s, 3H, CH$_3$), 1.36 (s, 3H, CH$_3$), 1.14 (t, J=7.4 Hz, 3H, SCH$_2$CH$_3$), 1.00 (s, 9H, TBDPS). $^{13}$C NMR (101 MHz, CHCl$_3$) δ163.7, 150.5, 137.6, 135.6, 135.5, 133.3, 133.0, 130.8, 129.8, 129.7, 128.5, 128.2, 127.7, 127.7, 123.4, 109.5, 79.8 (C-1), 78.7, 76.4, 75.0, 72.9, 72.6, 67.0, 62.1, 28.0, 26.7, 26.4, 24.3, 19.2, 14.2; HRMS (ESI) m/z calcd for C$_{42}$H$_{50}$NO$_9$SSi [M+H]$^+$ 772.2946, found 772.2947.

Compound 12*: The compound 11* (2.6 g, 3.4 mmol) was dissolved in a mixed solvent of MeOH/DCM (20:1, v/v, 57.0 mL), and potassium carbonate (0.57 g, 4.1 mmol) was added. The mixture was stirred at room temperature for 3 h. After TLC monitored that the reaction was complete, the reaction solution was directly concentrated under reduced pressure. After ethyl acetate was added and dissolved, the reaction solution was washed with a saturated saline solution. The organic phase was dried over Na$_2$SO$_4$, filtered and concentrated. The crude product was separated and purified with a silica gel chromatography column (petroleum ether/ethyl acetate, 15:1) to prepare the compound 12* (2.0 g, 3.23 mmol, 95%). [α]$^{22}_D$=62.7 (c 1.0, CHCl$_3$); $^1$H NMR (400 MHz, CDCl$_3$) δ7.65 (m, 4H, Ar), 7.48-7.27 (m, 11H, Ar), 5.56 (s, 1H, H-1), 4.94 (d, J=11.4 Hz, 1H, ArCH$_2$), 4.68 (d, J=11.4 Hz, 1H, ArCH$_2$), 4.31 (dd, J=7.2, 5.7 Hz, 1H, H-3), 4.18 (dd, J=5.6, 0.9 Hz, 1H, H-2), 4.12-4.04 (m, 2H, H-5, H-6), 3.82 (dd, J=10.2, 7.3 Hz, 1H, H-4), 3.74 (dd, J=10.0, 7.4 Hz, 1H, H-7), 3.63 (dd, J=10.0, 6.5 Hz, 1H, H-7'), 2.58-2.29 (m, SCH$_2$CH$_3$), 2.10 (br, 1H, OH), 1.53 (s, 3H, CH$_3$), 1.36 (s, 1H, CH$_3$), 1.16 (t, J=7.4 Hz, 3H, SCH$_2$CH$_3$), 1.07 (s, 9H, TBDPS). $^{13}$C NMR (101 MHz, CHCl$_3$) δ138.6, 135.7, 135.6, 135.6, 133.5, 133.3, 129.9, 129.9, 128.4, 128.0, 127.8, 127.7, 109.5, 79.8 (C-1), 78.8, 76.6, 75.7, 73.4, 69.4, 67.9, 65.0, 28.2, 27.0, 26.6, 24.2, 19.4, 14.3; HRMS (ESI) m/z calcd for C$_{35}$H$_{46}$O$_6$SSiNa [M+Na]$^+$ 645.2677, found 645.2672.

Compound 13*: The compound 12* (2.5 g, 4.0 mmol) was dissolved in anhydrous DMF (20.0 mL). After the solution was cooled to 0° C., sodium hydride (180 mg, 7.3 mmol, 60% dispersed in oil) was added. The reaction solution was stirred at 0° C. for half an hour, and then benzyl bromide (0.86 mL, 7.3 mmol) was added. The reaction solution was further stirred at room temperature for 3 h. After the reactants completely disappeared, the solution was cooled to 0° C., and water was added dropwise to quench the reaction. The mixture was extracted three times with DCM, and the organic phase was dried over anhydrous Na$_2$SO$_4$ and concentrated by reduced pressure distillation. The crude product was separated and purified using silica gel column chromatography (petroleum ether/ethyl acetate, 20:1) to prepare the compound 13* (2.4 g, 3.4 mmol, 85%). [α]$^{22}_D$=102.9 (c 1.0, CHCl$_3$); $^1$H NMR (400 MHz, CDCl$_3$) δ7.73-7.59 (m, 4H, Ar), 7.47-7.08 (m, 16H), 5.63-5.46 (m, 1H, H-1), 4.83 (d, J=11.6 Hz, 1H, ArCH$_2$), 4.60 (d, J=11.8 Hz, 1H, ArCH$_2$), 4.36-4.24 (m, 1H, H-3), 4.18 (d, J=11.8 Hz, 1H, ArCH$_2$), 4.16-4.14 (m, 2H, H-2, H-5), 4.11 (d, J=11.6 Hz, 1H, ArCH$_2$), 3.90-3.83 (m, 2H, H-4, H-6), 3.81 (dd, J=10.1, 3.6 Hz, 1H, H-7), 3.75 (dd, J=10.1, 7.0 Hz, 1H, H-7'), 2.66-2.27 (m, 2H, SCH$_2$CH$_3$), 1.57 (s, 1H, CH$_3$), 1.36 (s, 3H, CH$_3$), 1.15 (t, J=7.4 Hz, 3H, SCH$_2$CH$_3$), 1.06 (s, 9H, OTBDPS). $^{13}$C NMR (101 MHz, CDCl$_3$) δ138.8, 138.7, 135.9, 135.7, 133.6, 133.5, 129.9, 129.8, 128.3, 128.3, 128.1, 127.9, 127.7, 127.6, 127.5, 109.5, 79.9 (C-1), 79.1, 77.5, 77.2, 76.8, 76.6, 75.7, 73.6, 72.2, 68.4, 63.3, 28.1, 27.0, 26.6, 24.1, 19.3, 14.3; HRMS (ESI) m/z calcd for C$_{42}$H$_{52}$O$_6$SSiNa [M+Na]$^+$ 735.3146, found 735.3126.

Compound 14*: The compound 13* (1.52 g, 2.13 mmol) was dissolved in an 80% acetic acid aqueous solution (28.4 mL), and the reaction solution was heated to 60° C. and stirred for 12 h. After a TLC plate showed that the raw materials completely disappeared, the reaction was terminated by adding saturated NaHCO$_3$ to the reaction solution. The reaction solution was then extracted three times using DCM, and the organic phase was dried over Na$_2$SO$_4$, filtered and concentrated. The crude product was separated and purified by silica gel column chromatography (petroleum ether/ethyl acetate, 3:1) to prepare the compound 14* (1.39 g, 2.0 mmol, 94%). [α]$^{22}_D$=100.8 (c 1.0, CHCl$_3$); $^1$H NMR (700 MHz, CDCl$_3$) δ7.72-7.64 (m, 4H, Ar), 7.50-7.15 (m, 16H, Ar), 5.34 (s, 1H, H-1), 4.73 (d, J=11.7 Hz, 1H, ArCH$_2$), 4.64 (dd, J=11.8, 1.9 Hz, 1H, ArCH$_2$), 4.34 (d, J=11.6 Hz, 1H, ArCH$_2$), 4.29 (d, J=9.6 Hz, 1H, H-6), 4.26 (dd, J=11.9, 1.9 Hz, 1H, OH), 3.98-3.95 (m, 1H, H-2), 3.95-3.88 (m, 3H, H-4, H-5, H-7), 3.88-3.84 (m, 1H, H-7'), 3.77 (td, J=9.3, 1.9 Hz, 1H, H-3), 2.64-2.29 (m, 2H, SCH$_2$CH$_3$), 1.82 (s, 2H, OH), 1.19 (t, J=6.8 Hz, 3H, SCH$_2$CH$_3$), 1.10 (s, 9H, TBDPS). $^{13}$C NMR (176 MHz, CDCl$_3$) δ138.7, 138.1, 135.7, 135.5, 133.4, 133.3, 129.8, 129.8, 128.4, 128.4, 128.1, 127.8, 127.8, 127.7, 127.6, 127.4, 83.8 (C-1), 75.9, 73.8, 72.9, 72.8, 72.6, 70.1, 62.7, 26.9, 24.7, 19.2, 14.4; HRMS (ESI) m/z calcd for C$_{39}$H$_{48}$O$_6$SSiNa [M+Na]$^+$ 695.2833, found 695.2819.

Compound 15*: The compound 14* (1.39 g, 2.0 mmol) was dissolved in anhydrous DCM (20.0 mL). Triethyl orthobenzoate (635 μL, 3.0 mmol) and a catalytic amount of camphor sulfonic acid (CSA) (23.2 mg, 0.1 mmol) were added at room temperature. The reaction solution was further stirred for 3 h, an 80% acetic acid aqueous solution (1.0 mL) was added, and then the reaction solution was stirred at room temperature for 1 h. After the reaction was complete, the reaction solution was extracted three times using DCM. The organic phase was washed with saturated NaHCO$_3$, dried over anhydrous Na$_2$SO$_4$, filtered and concentrated. The crude product was separated and purified by silica gel column chromatography (petroleum ether/ethyl acetate, 3:1) to prepare the compound 15* (1.0 g, 1.3 mmol, 65%). [α]$^{22}_D$=23.6 (c 1.0, CHCl$_3$); $^1$H NMR (600 MHz, CDCl$_3$) δ8.09-7.82 (m, 2H, Ar), 7.66 (ddd, J=8.1, 5.7, 1.4 Hz, 4H), 7.55 (tt, J=7.4, 1.3 Hz, 1H), 7.45-7.18 (m, 19H), 5.44 (d, J=1.7 Hz, 2H), 4.73 (d, J=11.6 Hz, 1H), 4.70 (d, J=11.7 Hz, 1H), 4.36 (d, J=11.7 Hz, 1H), 4.35-4.34 (m, 1H), 4.25 (d, J=11.7 Hz, 1H), 4.23-4.20 (m, 2H), 4.03 (t, J=9.5 Hz, 1H), 3.96-3.83 (m, 3H), 2.62-2.46 (m, 3H), 2.06 (d, J=5.5 Hz, 1H), 1.18 (t, J=7.4 Hz, 3H), 1.08 (s, 9H). $^{13}$C NMR (151 MHz, CDCl$_3$) δ166.1, 138.5, 138.5, 135.7, 135.6, 135.5, 133.4, 133.3, 133.2, 129.9, 129.8, 129.7, 129.7, 128.4, 128.4, 128.3, 127.7, 127.6, 127.6, 127.5, 127.3, 81.9 (C-1), 77.2, 77.0, 76.9, 76.8, 76.0, 74.5, 74.2, 72.7, 71.7, 70.4, 62.5, 26.8, 25.1, 19.2, 14.5; HRMS (ESI) m/z calcd for C$_{46}$H$_{52}$O$_7$SSiNa [M+Na]$^+$ 799.3095, found 799.3093.

Compound 16*: The compound 15* (850 mg, 1.1 mmol) was dissolved in DCM (20.0 mL). Levulinic acid (192 mg, 1.65 mmol), dicyclohexylcarboimine (340 mg, 1.65 mmol), and N,N-dimethylpyridine (202 mg, 1.65 mmol) were respectively added, and the mixture was stirred at room temperature for 3 h. After the reaction was complete, the reaction solution was concentrated under reduced pressure. The crude product was separated and purified by column chromatography (petroleum ether/ethyl acetate, 8:1) to prepare the compound 16* (830 mg, 0.95 mmol, 86%). [α]$^{22}_D$=11.3 (c 1.0, CHCl$_3$); $^1$H NMR (600 MHz, CDCl$_3$) δ8.09-7.93 (m, 2H, Ar), 7.69-7.62 (m, 4H, Ar), 7.57 (tt, J=7.4, 1.3 Hz, 1H, Ar), 7.45-7.33 (m, 6H, Ar), 7.32-7.26 (m, 11H, Ar), 7.23-7.18 (m, 1H, Ar), 5.59 (dd, J=3.2, 1.7 Hz, 1H, H-2), 5.47-5.37 (m, 2H, H-1, H-3), 4.66 (d, J=11.7 Hz, 1H, ArCH$_2$), 4.58 (d, J=11.6 Hz, 1H, ArCH$_2$), 4.45 (d, J=9.8 Hz, 1H, H-5), 4.24 (d, J=11.7 Hz, 1H, ArCH$_2$), 4.20 (d, J=11.7 Hz, 1H, ArCH$_2$), 4.18 (t, J=9.7 Hz, 1H, H-4), 3.96-3.86 (m, 2H, H-6, H-7, H-7'), 2.71-2.32 (m, 6H, CH$_2$CH$_2$, SCH$_2$CH$_3$), 2.06 (s, 2H, Ac), 1.18 (t, J=7.4 Hz, 2H, SCH$_2$CH$_3$), 1.06 (s, 9H, TBDPS). $^{13}$C NMR (151 MHz, CDCl$_3$) δ206.2, 171.7, 165.4, 138.5, 138.4, 135.7, 135.5, 133.4, 133.3, 133.2, 129.9, 129.8, 129.7, 129.6, 128.4, 128.3, 128.3, 127.7, 127.6, 127.4, 127.1, 81.7 (C-1), 74.1, 73.4, 73.1, 72.8, 71.8, 70.6, 62.2, 37.8, 29.7, 27.9, 26.8, 24.9, 19.2, 14.4; HRMS (ESI) m/z calcd for C$_{51}$H$_{58}$O$_9$SSiNa [M+Na]$^+$ 897.3463, found 897.3469.

Compound 17*: The compound 16* (210 mg, 0.24 mmol) was dissolved in THF (2.4 mL). A 70% hydrogen fluoride/pyridine solution (6.3 μL, 2.4 mmol) was added at 0° C. The reaction solution restored to room temperature and was further stirred for 12 h. After a TLC plate monitored that the raw materials completely disappeared, the reaction solution was diluted with ethyl acetate and washed with a saturated ammonium chloride solution. The organic phase was dried over anhydrous Na$_2$SO$_4$, filtered and concentrated. The crude product was separated and purified by silica gel column chromatography (petroleum ether/ethyl acetate, 4:1) to prepare a compound intermediate with C7 hydroxyl exposed. The compound intermediate was dissolved in pyridine (2.4 mL), and acetic anhydride was added at 0° C. The reaction solution was stirred at room temperature for 12 h, then the reaction solution was diluted with DCM, washed with saturated NaHCO$_3$, and separated and purified by silica gel column chromatography (petroleum ether/ethyl acetate, 4:1) after reduced pressure distillation to prepare the compound 17* (66.8 mg, 0.098 mmol, 41%). [α]$^{22}_D$=38.29 (c 1.0, CHCl$_3$); $^1$H NMR (400 MHz, CDCl$_3$) δ8.14-7.85 (m, 2H, Ar), 7.68-7.57 (m, 1H, Ar), 7.48-7.21 (m, 12H, Ar), 5.64 (dd, J=3.1, 1.7 Hz, 1H, H-2), 5.45 (d, J=1.7 Hz, 1H, H-1), 5.41 (dd, J=8.8, 3.1 Hz, 1H, H-2), 4.90 (d, J=11.6 Hz, 1H, ArCH$_2$), 4.66 (d, J=11.3 Hz, 1H, ArCH$_2$), 4.61-4.51 (m, 2H, H-7, ArCH$_2$), 4.35 (d, J=11.3 Hz, 1H, ArCH$_2$), 4.33-4.22 (m, 3H, H-7', H-4, H-5), 4.19 (ddd, J=7.2, 5.8, 1.4 Hz, 1H, H-6), 2.80-2.56 (m, 4H, CH$_2$CH$_2$), 2.52-2.33 (m, 2H, SCH$_2$CH$_3$), 2.12 (s, 6H, CH$_3$), 1.31 (t, J=7.4 Hz, 3H, SCH$_2$CH$_3$). $^{13}$C NMR (101 MHz, CDCl$_3$) δ206.4, 171.9, 170.8, 165.6, 138.2, 138.1, 133.5, 130.0, 129.6, 128.7, 128.7, 128.7, 128.6, 128.6, 128.0, 127.9, 127.7, 127.6, 82.2 (C-1), 74.7, 73.9, 73.5, 73.0, 73.0, 72.0, 71.3, 62.6, 37.9, 29.9, 28.0, 25.3, 21.1, 14.8; HRMS (ESI) m/z calcd for C$_{37}$H$_{42}$O$_{10}$SNa [M+Na]$^+$ 701.2391, found 701.2385.

Compound 3*: The compound 17* (312 mg, 0.46 mmol) was dissolved in a THF/H$_2$O (1:1, v/v, 4.6 mL) solution, and bromosuccinimide (245 mg, 1.38 mmol) was added at 0° C. The reaction solution was stirred at room temperature for 4 h. After the reaction raw materials disappeared, the reaction solution was diluted with DCM and washed with saturated NaHCO$_3$. The reaction solution was dried over anhydrous Na$_2$SO$_4$, the organic phase was filtered and concentrated, and the crude product was purified by silica gel column chromatography to prepare a hemiacetal product intermediate (285 mg). The hemiacetal product intermediate was dissolved in dry DCM (4.6 mL), N-phenyltrifluoroacetyl chloride (345 μl, 2.3 mmol) and DBU (206 μL, 1.38 mmol) were added at 0° C., and the reaction solution was stirred at room temperature for 5 h. After TLC monitored that the reaction raw materials completely disappeared, the reaction solution was directly concentrated, and the crude product was purified by silica gel column chromatography (petroleum ether/ethyl acetate, 3:1) to prepare the compound 3* (338 mg, 0.42 mmol, 91%).

Example 2

Figure 3:
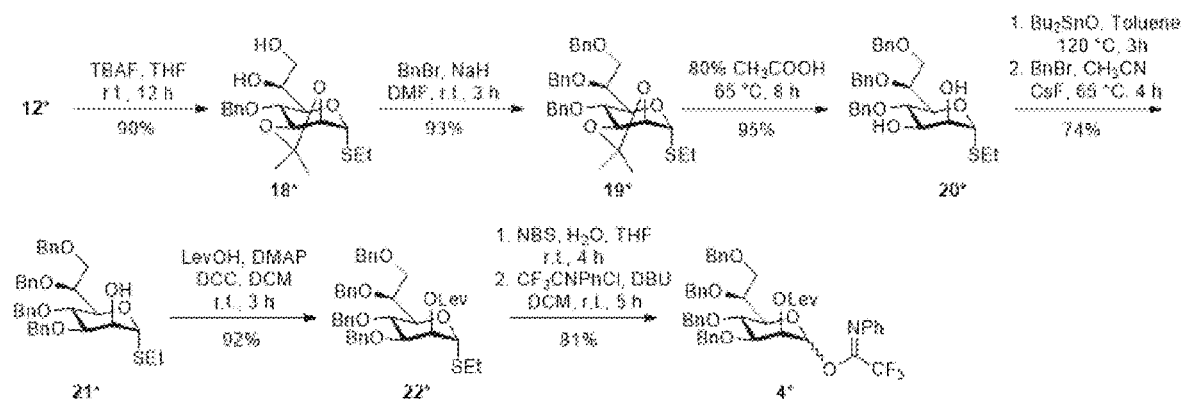
FIG. 3 shows the synthesis route of a saccharide block 4*.

A saccharide block 4* was synthesized as shown in FIG. 3:

A C7 TBDPS group was removed from the compound 12* using tetrabutylammonium fluoride to prepare a dihydroxy compound 18*, with a yield of 90%. The compound 18* underwent a benzylation reaction under benzyl bromide and sodium hydride to prepare a compound 19*, with a yield of 93%. O2,3-propylidene was removed from the compound 19* by 80% acetic acid treatment to prepare a compound 20*, with a yield of 95%. The C3 hydroxyl was selectively protected with benzyl under dibutyltin oxide to prepare a compound 21*, with a yield of 74%. Under an alkaline condition of DMAP and DCC, acetylpropynyl was introduced at the C2 of the compound 21* to prepare a compound 22*, with a yield of 92%. The terminal ethylthio was removed from the compound 22* under NBS, and then phenyltrifluoroacetylimino was introduced under DBU and phenyltrifluoroacetylimino chloride to prepare a compound 4*, with a two-step yield of 81%.

Compound 18*: The compound 12* (261 mg, 0.42 mmol) was dissolved in THF (1.4 mL), and TBAF (1 M THF solution, 0.42 mL, 0.42 mmol) was added at 0° C. The reaction solution was further stirred at room temperature for 12 h. After the reaction was complete, the reaction solution was diluted with ethyl acetate and washed with a saturated ammonium chloride solution. The organic phase was dried over anhydrous $Na_2SO_4$, filtered and concentrated. The crude product was separated and purified by silica gel column chromatography (petroleum ether/ethyl acetate, 4:1) to prepare the compound 18* (139 mg, 0.38 mmol, 90%). $[\alpha]^{22}_D$=83.2 (c 1.0, $CHCl_3$). $^1H$ NMR (400 MHz, $CDCl_3$) δ7.61-7.10 (m, 5H, Ar), 5.57 (s, 1H, H-1), 4.93 (d, J=11.2 Hz, 1H, $ArCH_2$), 4.66 (d, J=11.2 Hz, 1H, $ArCH_2$), 4.30 (dd, J=6.4, 6.4 Hz, 1H, H-3), 4.20 (d, J=5.6 Hz, 1H, H-2), 3.95-4.07 (m, 2H, H-5, H-6), 3.79 (dd, J=10.3, 7.3 Hz, 1H, H-7), 3.73 (dd, J=10.3, 5.7 Hz, 1H, H-7'), 3.70-3.62 (m, 1H, H-4), 2.71-2.44 (m, 2H, $SCH_2CH_3$), 2.24 (br, 1H, OH), 2.09 (br, 1H, OH), 1.54 (s, 3H, $CH_3$), 1.37 (s, 3H, $CH_3$), 1.30 (t, J=7.4 Hz, 3H, $SCH_2CH_3$). $^{13}C$ NMR (101 MHz, $CDCl_3$) δ138.0, 128.4, 128.1, 127.9, 109.5, 80.2 (C-1), 78.5, 77.3, 77.0, 76.7, 76.4, 75.7, 73.3, 69.8, 69.5, 64.8, 28.0, 26.5, 24.5, 14.4; HRMS (ESI) m/z calcd for $C_{19}H_{28}O_6SNa$ $[M+Na]^+$ 407.1499, found 407.1495.

Compound 19*: The compound 18* (950 mg, 2.47 mmol) was dissolved in anhydrous DMF (12.0 mL). After the solution was cooled to 0° C., sodium hydride (395 mg, 9.88 mmol, 60% dispersed in oil) was added. The reaction solution was stirred at 0° C. for half an hour, and then benzyl bromide (1.17 mL, 9.88 mmol) was added. The reaction solution was further stirred at room temperature for 3 h. After the reactants completely disappeared, the solution was cooled to 0° C., and water was added dropwise to quench the reaction. The mixture was extracted three times with DCM, and the organic phase was dried over anhydrous $Na_2SO_4$ and concentrated by reduced pressure distillation. The crude product was separated and purified by silica gel column chromatography (petroleum ether/ethyl acetate, 20:1) to prepare the compound 19* (1.1 g, 1.85 mmol, 75%). $[\alpha]^{22}_D$=65.3 (c 1.0, $CHCl_3$); $^1H$ NMR (400 MHz, $CDCl_3$) δ7.45-7.13 (m, 15H, Ar), 5.63 (s, 1H, H-1), 4.90 (d, J=11.4 Hz, 1H, $ArCH_2$), 4.82 (d, J=11.8 Hz, 1H, $ArCH_2$), 4.56 (s, 2H, $ArCH_2$), 4.51 (d, J=11.7 Hz, 1H, $ArCH_2$), 4.35 (t, J=6.3 Hz, 1H, H-3), 4.31 (d, J=11.6 Hz, 1H, $ArCH_2$), 4.23 (dd, J=5.8, 1.4 Hz, 1H, H-2), 4.19-4.08 (m, 2H, H-5, H-6), 3.90 (dd, J=10.0, 7.1 Hz, 1H, H-4), 3.78 (dd, J=9.5, 6.5 Hz, 1H, H-7), 3.70 (dd, J=9.5, 5.8 Hz, 1H, H-7'), 2.72-2.40 (m, 2H, $SCH_2CH_3$), 1.59 (s, 3H, $CH_3$), 1.41 (s, 3H, $CH_3$), 1.26 (t, J=7.4 Hz, 3H, $SCH_2CH_3$). $^{13}C$ NMR (101 MHz, $CDCl_3$) δ138.8, 138.5, 138.4, 138.2, 128.5, 128.5, 128.4, 128.4, 128.0, 127.9, 127.8, 127.7, 127.7, 127.7, 127.7, 109.6, 80.2 (C-1), 79.1, 77.5, 77.2, 76.8, 75.7, 75.6, 73.8, 73.6, 72.5, 72.3, 70.9, 69.5, 29.8, 28.1, 26.6, 24.3, 14.5, 14.3; HRMS (ESI) m/z calcd for $C_{33}H_{40}O_6SNa$ $[M+Na]^+$ 587.2438, found 587.2440.

Compound 20*: The compound 19* (609 mg, 1.08 mmol) was dissolved in an 80% acetic acid aqueous solution (15.0 mL), and the reaction solution was heated to 65° C. and stirred for 8 h. After a TLC plate showed that the raw materials completely disappeared, the reaction solution was concentrated under reduced pressure, diluted with DCM and washed with saturated $NaHCO_3$. The organic phase was dried over $Na_2SO_4$, filtered and concentrated. The crude product was separated and purified by silica gel column chromatography (petroleum ether/ethyl acetate, 3:1) to prepare the compound 20* (542 mg, 1.03 mmol, 95%). $[\alpha]^{22}_D$=89.9 (c 1.0, $CHCl_3$); $^1H$ NMR (400 MHz, $CDCl_3$) δ7.71-6.90 (m, 15H, Ar), 5.33 (d, J=1.5 Hz, 1H, H-1), 4.85 (d, J=11.6 Hz, 1H, $ArCH_2$), 4.81-4.73 (m, 1H, $ArCH_2$), 4.55 (d, J=11.6 Hz, 3H, $ArCH_2$), 4.45 (d, J=11.4 Hz, 1H, $ArCH_2$), 4.15 (s, 1H, H-5, H-6), 3.93 (dd, J=3.2, 1.5 Hz, 1H, H-2), 3.91-3.84 (m, 2H, H-3, H-4), 3.84-3.78 (m, 1H, H-7), 3.70 (dd, J=9.8, 5.6 Hz, 1H, H-7'), 2.64-2.45 (m, 4H, $SCH_2CH_3$, 2×OH), 1.24 (t, J=7.4 Hz, 3H, $SCH_2CH_3$). $^{13}C$ NMR (101 MHz, $CDCl_3$) δ138.5, 138.1, 138.0, 128.5, 128.4, 128.4, 128.2, 127.9, 127.7, 127.7, 127.7, 127.6, 84.1 (C-1), 77.3, 77.2, 77.0, 76.7, 75.8, 75.3, 74.1, 73.5, 73.1, 72.8, 72.6, 71.3, 70.7, 24.8, 14.6; HRMS (ESI) m/z calcd for $C_{30}H_{36}O_6SNa$ $[M+Na]^+$ 547.2125, found 547.2135.

Compound 21*: The compound 20* (575 mg, 1.10 mmol) was dissolved in toluene (5.5 mL), and dibutyltin oxide (409 mg, 1.65 mmol) was added to a reaction flask. The reaction solution was heated to 120° C., refluxed for 3 h, and then distilled to remove half of the reaction solvent by volume. After the reaction solution cooled to room temperature, cesium fluoride (250 mg, 1.65 mmol) and benzyl bromide (195 μL, 1.65 mmol) were respectively added to the reaction flask, and the reaction solution was stirred at 65° C. for 12 h. After the reaction materials completely disappeared, the reaction solution was filtered with diatomaceous earth, and the filtrate was concentrated under reduced pressure. The crude product was separated and purified by silica gel column chromatography (petroleum ether/ethyl acetate, 3:1) to prepare the compound 21* (490 mg, 0.81 mmol, 74%). $[\alpha]^{22}_D$=55.2 (c 1.0, $CHCl_3$); $^1H$ NMR (400 MHz, $CDCl_3$) δ7.37-7.18 (m, 20H, Ar), 5.37 (d, J=1.5 Hz, 1H, H-1), 4.88-4.74 (m, 2H, $ArCH_2$), 4.66 (d, J=11.4 Hz, 1H, $ArCH_2$), 4.61 (d, J=11.4 Hz, 1H, $ArCH_2$), 4.55-4.48 (m, 3H, $ArCH_2$), 4.33 (d, J=11.1 Hz, 1H, $ArCH_2$), 4.18-4.10 (m, 2H, H-5, H-6), 4.08 (d, J=2.2 Hz, 1H, H-2), 4.03 (dd, J=9.3, 9.3 Hz, 1H, H-4), 3.83 (dd, J=8.9, 3.2 Hz, 1H, H-3), 3.81-3.76 (dd, J=9.77, 6.24 Hz, 1H, H-7), 3.68 (dd, J=9.8, 5.6 Hz, 1H, H-7'), 2.68 (br, 1H, OH), 2.62-2.37 (m, 2H, $SCH_2CH_3$), 1.21 (t, J=7.4 Hz, 3H, $SCH_2CH_3$). $^{13}C$ NMR (101 MHz, $CDCl_3$) δ138.8, 138.6, 138.3, 137.8, 128.7, 128.5, 128.5, 128.5, 128.2, 128.2, 128.1, 127.8, 127.7, 127.7, 127.6, 83.8 (C-1), 81.1, 77.5, 77.2, 76.8, 75.3, 74.8, 74.1, 73.6, 73.1, 72.0, 71.8, 70.8, 69.9, 24.9, 14.8; HRMS (ESI) m/z calcd for $C_{37}H_{42}O_6SNa$ $[M+Na]^+$ 637.2594, found 637.2598.

Compound 22*: The compound 21* (377 mg, 0.61 mmol) was dissolved in DCM (12.3 mL). Levulinic acid (107 mg, 0.92 mmol), dicyclohexylcarboimine (190 mg, 0.92 mmol) and N,N-dimethylpyridine (113 mg, 0.92 mmol) were added, and the reaction solution was stirred at room temperature for 3 h. After the reaction was complete, the reaction solution was directly concentrated under reduced pressure, and the crude product was separated and purified by silica gel column chromatography (petroleum ether/ethyl acetate, 3:1) to prepare the compound 22* (401 mg, 0.56 mmol, 92%). $[\alpha]^{22}_D$=62.5 (c 1.0, CHCl$_3$); $^1$H NMR (400 MHz, CDCl$_3$) δ7.63-6.81 (m, 20H, Ar), 5.44 (dd, J=3.2, 1.7 Hz, 1H, H-2), 5.30 (d, J=1.5 Hz, 1H, H-1), 4.93-4.80 (m, 2H, ArCH$_2$), 4.65 (d, J=11.0 Hz, 1H, ArCH$_2$), 4.53-4.41 (m, 4H, ArCH$_2$), 4.32 (d, J=11.1 Hz, 1H, ArCH$_2$), 4.19-4.11 (m, 2H, H-5, H-6), 4.03 (dd, J=9.1, 9.1 Hz, 1H, H-4), 3.90 (dd, J=9.1, 3.2 Hz, 1H, H-3), 3.80 (dd, J=9.8, 6.5 Hz, 1H, H-7), 3.66 (dd, J=9.7, 5.6 Hz, 1H, H-7'), 2.76-2.63 (m, 4H, CH$_2$CH$_2$), 2.63-2.43 (m, 2H, SCH$_2$CH$_3$), 2.11 (s, 3H, CH$_3$), 1.20 (t, J=7.4 Hz, 3H, SCH$_2$CH$_3$). $^{13}$C NMR (101 MHz, CDCl$_3$) δ166.3, 138.4, 138.3, 135.9, 135.8, 133.5, 130.0, 129.7, 128.7, 128.6, 128.6, 128.1, 128.1, 128.0, 127.9, 127.8, 127.8, 82.3 (C-1), 75.7, 75.4, 75.3, 74.8, 74.6, 73.2, 71.9, 71.0, 69.6, 69.6, 69.6, 69.5, 66.4, 66.4, 25.5, 14.8; HRMS (ESI) m/z calcd for C$_{42}$H$_{48}$O$_8$SNa [M+Na]$^+$ 735.2962, found 735.2951.

Compound 4*: The compound 22* (71.2 mg, 0.10 mmol) was dissolved in THF/H$_2$O (1:1, v/v, 1.0 mL), and bromosuccinimide (53.3 mg, 0.3 mmol) was added. The reaction solution was stirred at room temperature for 4 h. After the reaction raw materials disappeared, the reaction solution was diluted with DCM, then washed with saturated NaHCO$_3$ and dried over anhydrous Na$_2$SO$_4$. The organic phase was filtered and concentrated, and the crude product was purified by column chromatography to prepare an acetal product intermediate (48.7 mg). The acetal product intermediate was dissolved in dry acetone (0.8 ml), and N-phenyltrifluoroacetyl chloride (79 μL, 0.53 mmol) and potassium carbonate (36.0 mg, 0.26 mmol) were added at 0° C. The reaction solution was stirred at room temperature for 5 h. After the reaction was complete, the reaction solution was directly concentrated. The crude product was purified by silica gel column chromatography (petroleum ether/ethyl acetate, 8:1) to prepare the compound 4* (68.8 mg, 0.081 mmol, 81%). $^1$H NMR (700 MHz, CDCl$_3$) δ7.37-7.11 (m, 22H, Ar), 7.03 (t, J=7.5 Hz, 1H, Ar), 6.67 (d, J=7.8 Hz, 2H, Ar), 6.15 (br, 1H, H-1), 5.40 (s, 1H, H-2), 4.81 (d, J=10.8 Hz, 1H, ArCH$_2$), 4.77 (d, J=11.6 Hz, 1H, ArCH$_2$), 4.64 (d, J=10.9 Hz, 1H, ArCH$_2$), 4.52-4.42 (m, 4H, ArCH$_2$), 4.30 (d, J=10.8 Hz, 1H, ArCH$_2$), 4.07 (dd, J=6.2, 6.2 Hz, 1H, H-6), 4.02 (dd, J=9.6, 9.6 Hz, 1H, H-4), 3.97 (d, J=9.6 Hz, 1H, H-3), 3.84 (d, J=9.7 Hz, 1H. H-5), 3.76 (dd, J=9.9, 6.8 Hz, 1H, H-7), 3.61 (dd, J=10.1, 5.4 Hz, 1H, H-7'), 2.72-2.45 (m, 4H, CH$_2$CH$_2$), 2.03 (s, 2H, CH$_3$). $^{13}$C NMR (176 MHz, CDCl$_3$) δ206.2, 171.9, 143.3, 138.6, 138.4, 138.1, 137.5, 129.6, 129.3, 128.9, 128.9, 128.7, 128.6, 128.5, 128.5, 128.5, 128.4, 128.4, 128.2, 128.1, 128.1, 127.9, 127.9, 127.8, 127.8, 127.8, 127.7, 127.6, 127.1, 126.5, 124.6, 120.6, 119.4, 118.5, 94.2, 80.8, 78.1, 75.1, 74.9, 74.0, 73.7, 73.4, 73.1, 72.2, 70.6, 67.5, 38.0, 29.9, 28.2; HRMS (ESI) m/z calcd for C$_{48}$H$_{48}$F$_3$NO$_9$Na [M+Na]$^+$ 862.3173, found 862.3162.

Example 3

Figure 4:
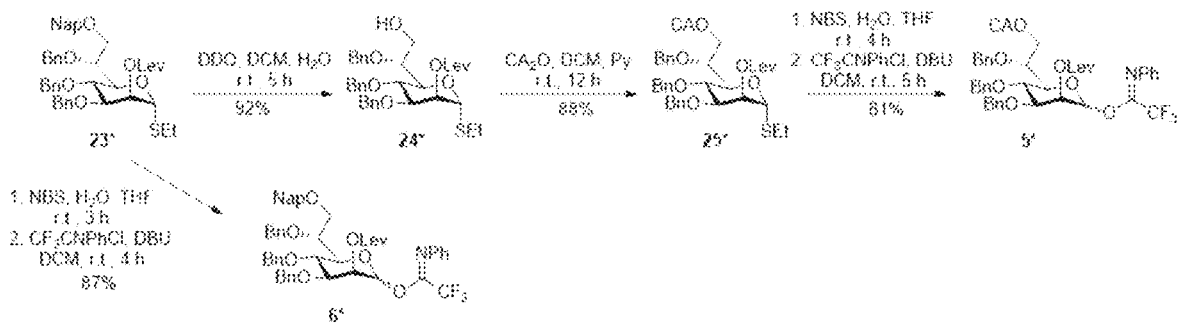
FIG. 4 shows the synthesis routes of saccharide blocks 5* and 6*.

Saccharide blocks 5* and 6* were synthesized as shown in FIG. 4:

Starting from a reported compound 23*, O7 2-naphthylmethylene was removed under DDQ to prepare a compound 24*, with a yield of 92%. C7 hydroxyl was protected by monochloroacetyl under monochloroacetic anhydride and pyridine to prepare a compound 25*, with a yield of 88%. The thioglucoside 25* underwent desulfurization and acylation reactions to prepare a phenyl trifluoroacetimidate donor 5*, with a two-step yield of 83%. The compound 23* also underwent desulfurization and acylation reactions to prepare a heptose donor 6*, with a two-step yield of 87%.

Compound 25*: The compound 23* (472 mg, 0.62 mmol) was dissolved in a mixed solvent of DCM/H$_2$O (9:1, v/v, 12.1 mL). DDQ (211 mg, 0.93 mmol) was added to the reaction solution at room temperature, and the reaction continued at room temperature for 5 h. After the reaction raw materials completely disappeared, the reaction solution was diluted with DCM and washed sequentially with a 10% Na$_2$S$_2$O$_3$ solution and a saturated NaHCO$_3$ solution. The organic phase was dried over Na$_2$SO$_4$, filtered and concentrated. The crude product was separated and purified by silica gel column chromatography (petroleum ether/ethyl acetate, 3:1) to prepare the compound 24* (355 mg, 92%). The compound 24* (340 mg, 0.55 mmol) was dissolved in DCM (5.5 mL), and chloroacetic anhydride (188 mg, 1.1 mmol) and pyridine (1.1 mL) were added at 0° C. The reaction solution was stirred at room temperature for 12 h. After TLC monitored that the reaction was complete, the reaction solution was diluted with DCM, washed with saturated NaHCO$_3$, filtered and concentrated. The crude product was purified by silica gel column chromatography (petroleum ether/ethyl acetate, 7:1) to prepare the compound 25* (338 mg, 0.055 mmol 88%). $[\alpha]^{22}_D$=73.3 (c 1.0, CHCl$_3$); $^1$H NMR (400 MHz, CDCl$_3$) δ7.66-6.82 (m, 18H), 5.41 (t, J=2.3 Hz, 1H), 5.24 (d, J=1.6 Hz, 1H), 4.90 (d, J=10.9 Hz, 1H), 4.76 (d, J=12.0 Hz, 1H), 4.72-4.46 (m, 5H), 4.36-4.25 (m, 3H), 4.00-3.87 (m, 5H), 3.83 (dd, J=9.5 Hz, 1H), 2.82-2.48 (m, 7H), 2.16 (s, 3H), 1.31-1.23 (m, 4H). $^{13}$C NMR (101 MHz, CDCl$_3$) δ 206.3, 172.0, 167.2, 138.2, 138.2, 137.7, 128.6, 128.5, 128.5, 128.4, 128.2, 128.1, 128.0, 127.8, 82.4 (C-1), 79.0, 76.5, 75.1, 74.2, 72.3, 72.0, 71.8, 70.5, 66.4, 40.9, 38.1, 29.9, 28.3, 25.6, 15.0; HRMS (ESI) m/z calcd for C$_{89}$H$_{90}$O$_{16}$ClSNa [M+Na]$^+$ 721.2209, found 721.2213.

Compound 5*: The compound 25* (95.0 mg, 0.14 mmol) was dissolved in a mixed solvent of THF/H$_2$O (v/v, 1:1, 2.8 mL), and bromosuccinimide (74.8 mg, 0.42 mmol) was added. The reaction solution was stirred at room temperature for 3 h. After TLC monitored that the reaction raw materials disappeared, the reaction solution was diluted with DCM. The organic phase was washed with 10% Na$_2$S$_2$O$_3$ and NaHCO$_3$ respectively, dried over anhydrous Na$_2$SO$_4$, filtered and concentrated. The crude product was purified by column chromatography to prepare an acetal product intermediate (85.0 mg). The acetal product intermediate was dissolved in dry DCM (1.4 mL), and N-phenyltrifluoroacetyl chloride (113 μl, 0.70 mmol) and DBU (62.8 μl, 0.42 mmol) were added at 0° C. The reaction solution was stirred at room temperature for 3 h. After TLC monitored that the reaction raw materials completely disappeared, the reaction solution was diluted with DCM and washed with a saturated NaHCO$_3$ solution. The organic phase was dried over anhydrous Na$_2$SO$_4$, filtered and directly concentrated. The crude product was purified by silica gel column chromatography (petroleum ether/ethyl acetate, 8:1) to prepare the compound 5* (93.0 mg, 0.11 mmol, 81%). $^1$H NMR (400 MHz, CDCl$_3$) δ7.41-7.18 (m, 16H, Ar), 7.10 (t, J=7.4 Hz, 1H, Ar), 6.79 (d, J=7.8 Hz, 2H, Ar), 6.19 (s, 1H, H-1), 5.46 (t, J=2.6 Hz, 1H, H-2), 4.92 (d, J=10.7 Hz, 1H, ArCH$_2$) 4.78-4.64 (m, ArCH$_2$), 4.61-4.55 (m, 2H, ArCH$_2$), 4.35 (h, J=7.9 Hz, 2H, H-7, H-7'), 4.09-3.84 (m, 6H), 2.92-2.49 (m, 4H, CH$_2$CH$_2$), 2.15 (s, 3H, Ac). $^{13}$C NMR (101 MHz, CDCl$_3$) δ206.0, 171.8, 167.2, 143.2, 138.1, 137.8, 137.5, 129.3, 128.9, 128.6, 128.5, 128.5, 128.4, 128.2, 128.1, 128.0, 127.9, 124.6, 119.5, 94.0 (C-1), 77.9, 76.5, 75.3, 74.4, 73.3, 72.7, 72.3, 40.9, 38.1, 29.9, 29.4, 28.9, 28.1.

Compound 6*: The compound 23* (101 mg, 0.13 mmol) was dissolved in a mixed solvent of THF/$H_2O$ (1:1, v/v, 2.6 mL), and bromosuccinimide (69.4 mg, 0.39 mmol) was added. The reaction solution was stirred at room temperature for 3 h. After TLC monitored that the reaction raw materials disappeared, the reaction solution was diluted with DCM. The organic phase was washed with 10% $Na_2S_2O_3$ and $NaHCO_3$ respectively, dried over anhydrous $Na_2SO_4$, filtered and concentrated. The crude product was purified by column chromatography to prepare an acetal product intermediate (83.5 mg). The acetal product intermediate was dissolved in dry DCM (2.6 mL), and N-phenyltrifluoroacetyl chloride (105 μl, 0.65 mmol) and DBU (58.3 μl, 0.39 mmol) were added at 0° C. The reaction solution was stirred at room temperature for 4 h. After TLC monitored that the reaction raw materials completely disappeared, the reaction solution was diluted with DCM and washed with a saturated $NaHCO_3$ solution. The organic phase was dried over anhydrous $Na_2SO_4$, filtered and directly concentrated. The crude product was purified by silica gel column chromatography (petroleum ether/ethyl acetate, 5:1) to prepare the compound 6* (100 mg, 0.024 mmol, 87%). $[\alpha]^{22}_D$=12.2 (c 1.0, $CHCl_3$). $^1H$ NMR (400 MHz, $CDCl_3$) δ7.89-7.71 (m, 4H, Ar), 7.53-7.39 (m, 5H, Ar), 7.39-7.30 (m, 9H, Ar), 7.28-7.22 (m, 4H, Ar), 7.21-7.16 (m, 2H, Ar), 7.13-7.06 (m, 1H, Ar), 6.78 (d, J=7.7 Hz, 2H, Ar), 6.23 (s, 1H, H-1), 5.47 (t, J=2.5 Hz, 1H, H-2), 4.88 (d, J=10.6 Hz, 1H, ArCH$_2$), 4.81 (d, J=11.8 Hz, 1H, ArCH$_2$), 4.75 (d, J=11.1 Hz, 1H, ArCH$_2$), 4.70 (d, J=11.2 Hz, 3H, ArCH$_2$), 4.63 (d, J=10.6 Hz, 1H, ArCH$_2$), 4.59 (d, J=11.0 Hz, 1H, ArCH$_2$), 4.17-3.99 (m, 4H), 3.90-3.71 (m, 2H), 2.79-2.50 (m, 4H, CH$_2$CH$_2$), 2.12 (s, 3H, CH$_3$). $^{13}$C NMR (101 MHz, $CDCl_3$) δ205.9, 171.7, 143.2, 138.6, 138.0, 137.5, 135.8, 133.3, 133.0, 129.4, 129.2, 128.7, 128.5, 128.4, 128.3, 128.1, 128.0, 128.0, 127.9, 127.7, 127.7, 127.6, 127.5, 126.4, 126.2, 126.1, 125.8, 125.6, 124.4, 120.4, 119.4, 118.4, 92.9 (C-1), 78.2, 77.8, 75.0, 74.6, 73.7, 73.4, 72.7, 72.1, 70.6, 67.5, 37.8, 29.7, 27.9.

Example 4

Figure 5:
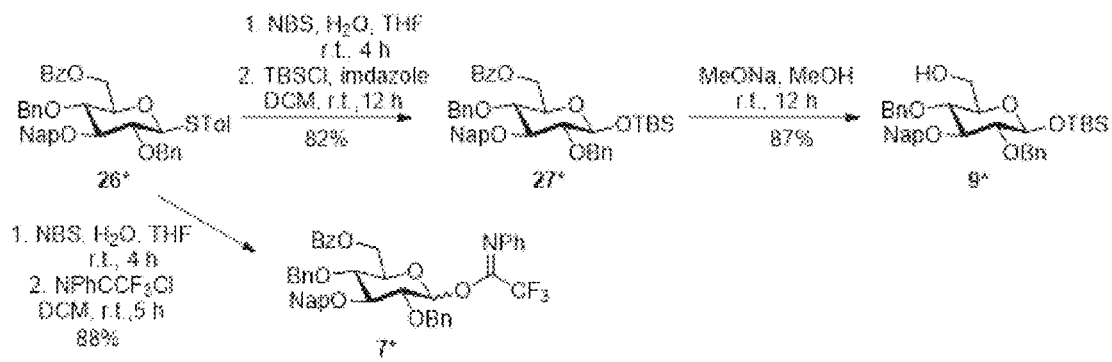
FIG. 5 shows the synthesis routes of saccharide blocks 7* and 9*.

Saccharide blocks 7* and 9* were synthesized as shown in FIG. 5:

Terminal phenylmethylthio was removed from the compound 26* under an NBS condition. TBS was introduced for protection at the C1 hydroxyl of a hemiacetal intermediate under TBSCl and imidazole to prepare a compound 27*, with a two-step yield of 82%. The C6 benzoyl was removed under sodium methoxide, exposing the C6 hydroxyl to prepare a glycosyl receptor 9*, with a yield of 87%. The compound 26* underwent desulfurization and acylation reactions to prepare a heptose donor 7*, with a two-step yield of 88%.

Compound 7*: The compound 26* (100 mg, 0.14 mmol) was dissolved in THF/$H_2O$ (1:1, v/v, 7.0 mL), and bromosuccinimide (7.5 mg, 0.042 mmol) was added. The reaction solution was stirred at room temperature for 4 h. After the reaction raw materials disappeared, the reaction solution was diluted with DCM, then washed with saturated $NaHCO_3$ and dried over anhydrous $Na_2SO_4$. The organic phase was filtered and concentrated, and the crude product was purified by column chromatography to prepare an acetal product intermediate (78.6 mg). The acetal product intermediate was dissolved in dry DCM (3.75 ml), and N-phenyltrifluoroacetyl chloride (97 μl, 0.365 mmol) and 1,8-diazabicyclo[5.4.0]undec-7-ene (DBU) (58.0 μl, 0.39 mmol) were added at 0° C. The reaction solution was stirred at room temperature for 5 h. After the reaction was complete, the reaction solution was directly concentrated. The crude product was purified by silica gel column chromatography (petroleum ether/ethyl acetate, 20:1) to prepare the compound 7* (96.0 mg, 0.12 mmol, 88%). $[\alpha]^{22}_D$=71.3 (c 1.0, $CHCl_3$); $^1H$ NMR (400 MHz, $CDCl_3$) δ8.14-8.00 (m, 5H), 7.94-7.73 (m, 12H), 7.68-7.07 (m, 37H), 6.87-6.67 (m, 5H), 6.55 (br, 1H, H-1), 5.80 (br, 1H, H-1), 5.27-4.80 (m, 13H, ArCH), 4.75-4.55 (m, 8H, ArCH, H-6, H-6), 4.26-4.12 (m, 2H), 3.94-3.63 (m, 8H). $^{13}$C NMR (101 MHz, $CDCl_3$) δ166.2, 166.1, 143.5, 143.4, 137.7, 137.6, 137.5, 137.4, 135.8, 135.6, 133.4, 133.3, 133.2, 133.2, 133.1, 129.8, 129.7, 129.1, 128.8, 128.7, 128.6, 128.6, 128.6, 128.5, 128.4, 128.3, 128.3, 128.3, 128.2, 128.2, 128.1, 128.1, 128.0, 128.0, 128.0, 127.8, 127.7, 127.7, 126.9, 126.7, 126.2, 126.2, 126.1, 126.1, 126.0, 126.0, 125.9, 125.3, 124.4, 124.2, 119.4, 119.3, 97.0 (C-1), 93.0 (C-1), 84.5, 81.6, 80.8, 79.5, 77.3, 76.1, 75.9, 75.51, 75.54, 75.3, 75.2, 73.9, 73.4, 71.7, 63.2, 63.0, 21.5; HRMS (ESI) m/z calcd for $C_{46}H_{40}F_3NO_7Na$ [M+Na]$^+$ 798.2649.

Compound 27*: The compound 26* (1.45 g, 2.04 mmol) was dissolved in THF/$H_2O$ (1:1, v/v, 21.0 mL), and bromosuccinimide (1.09 g, 6.12 mmol) was added. The reaction solution was stirred at room temperature for 4 h. After the reaction raw materials completely disappeared, the reaction solution was washed with saturated $NaHCO_3$ and 10% $Na_2S_2O_3$ (1:1, v/v), dried over anhydrous $Na_2SO_4$ and concentrated. The crude product was purified by column chromatography to prepare a hemiacetal product intermediate (1.1 g). The product intermediate was dissolved in dry DCM (12.0 ml), and the reaction solution was cooled to 0° C. Imidazole (495 mg, 7.3 mmol) and TBSCl (630 mg, 3.64 mmol) were added, and the reaction solution was stirred at room temperature for 12 h. After TLC monitored that the reaction was complete, the reaction solution was quenched with a saturated ammonium chloride solution, and the mixed solution was extracted three times with DCM. The organic phase was washed with water and dried over anhydrous $Na_2SO_4$. After reduced pressure concentration, the crude product was purified by silica gel column chromatography (petroleum ether/ethyl acetate, 50:1) to prepare the compound 27* (1.2 g, 1.67 mmol, two-step yield of 82%). $[\alpha]^{22}_D$=30.3 (c 1.0, $CHCl_3$). $^1H$ NMR (400 MHz, $CDCl_3$) δ8.09-7.95 (m, 2H, Ar), 7.87-7.67 (m, 4H, Ar), 7.60-7.53 (m, 1H, Ar), 7.52-7.15 (m, 15H, Ar), 5.11 (d, J=11.0 Hz, 1H, ArCH$_2$), 5.02 (d, J=11.0 Hz, 1H, ArCH$_2$), 4.96 (d, J=11.1 Hz, 1H, ArCH$_2$), 4.92 (d, J=10.9 Hz, 1H, ArCH$_2$), 4.78 (d, J=11.0 Hz, 1H, ArCH$_2$), 4.74 (d, J=7.5 Hz, 1H, H-1), 4.64 (d, J=10.9 Hz, 1H, ArCH$_2$), 4.63 (dd, J=11.7, 2.0 Hz, 1H, H-6), 4.42 (dd, J=11.7, 6.0 Hz, 1H, H-6'), 3.76 (t, J=9.0 Hz, 1H, H-3), 3.69 (ddd, J=9.9, 6.0, 2.1 Hz, 1H, H-5), 3.61 (dd, J=9.8, 8.7 Hz, 1H, H-4), 3.48 (dd, J=9.3, 7.5 Hz, 1H, H-2), 0.91 (s, 9H, OTBS), 0.14 (s, 3H, CH$_3$), 0.12 (s, 3H, CH$_3$). $^{13}$C NMR (101 MHz, $CDCl_3$) δ166.4, 138.5, 137.8, 136.0, 133.4, 133.2, 133.1, 130.0, 129.9, 128.6, 128.5, 128.4, 128.3, 128.2, 128.2, 128.1, 127.8, 127.8, 126.7, 126.2, 126.1, 126.0, 98.4 (C-1), 84.8, 84.2, 78.1, 76.0, 75.2, 75.1, 73.3, 64.0, 25.9, 18.1, −4.0, −4.9; HRMS (ESI) m/z calcd for $C_{44}H_{50}O_7SiNa$ [M+Na]$^+$ 741.3218, found 741.3215.

Compound 9*: The compound 27* (20.0 mg, 0.028 mmol) was dissolved in methanol, and sodium methoxide (10 mg) was added. The reaction solution was stirred at room temperature for 12 h. After the reaction was complete, the crude product was purified by silica gel column chromatography (petroleum ether/ethyl acetate, 15:1) to prepare the compound 9* (15.1 mg, 0.024 mmol, 87%). $[\alpha]^{22}_D$=12.8 (c 1.0, CHCl$_3$); $^1$H NMR (600 MHz, CDCl$_3$) δ7.84-7.78 (m, 1H, Ar), 7.78-7.75 (m, 1H, Ar), 7.75-7.71 (m, 1H, Ar), 7.70-7.68 (m, 1H, Ar), 7.50-7.43 (m, 2H, Ar), 7.42-7.38 (m, 1H, Ar), 7.36-7.32 (m, 2H, Ar), 7.32-7.21 (m, 7H, Ar), 5.07 (d, J=11.2 Hz, 1H, ArCH$_2$), 4.99 (d, J=11.0 Hz, 1H, ArCH$_2$), 4.95 (d, J=11.1 Hz, 1H, ArCH$_2$), 4.89 (d, J=11.0 Hz, 1H ArCH$_2$), 4.77 (d, J=11.0 Hz, 1H ArCH$_2$), 4.73 (d, J=7.5 Hz, 1H, H-1), 4.67 (d, J=11.0 Hz, 1H ArCH$_2$), 3.86 (dd, J=11.8, 2.9 Hz, 1H, H-6), 3.72 (d, J=9.3 Hz, 1H, H-3), 3.70 (dd, J=7.6, 4.3 Hz, 1H, H-6'), 3.59 (t, J=9.4 Hz, 1H, H-4), 3.41 (dd, J=9.3, 7.4 Hz, 1H, H-2), 3.43-3.37 (m, 1H, H-5), 0.96 (s, 9H, OTBS), 0.17 (s, 3H, CH$_3$), 0.17 (s, 3H CH$_3$). $^{13}$C NMR (151 MHz, CDCl$_3$) δ=138.5, 138.2, 136.2, 133.5, 133.1, 128.6, 128.5, 128.2, 128.1, 128.1, 128.1, 128.0, 127.8, 127.8, 126.6, 126.1, 126.1, 126.1, 125.9, 98.3 (C-1), 84.6, 84.2, 77.9, 75.8, 75.3, 75.1, 75.1, 62.4, 25.9, 18.2, −3.9, −3.9, −4.7; HRMS (ESI) m/z calcd for C$_{37}$H$_{46}$O$_6$SiNa [M+Na]$^+$ 637.2956, found 637.2951.

Example 5

Figure 6:
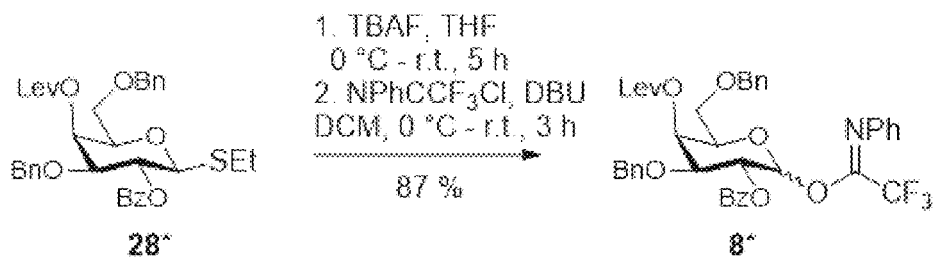
FIG. 6 shows the synthesis route of a saccharide block 8*.

A saccharide block 8* was synthesized as shown in FIG. 6:

A compound 28* (67.0 mg, 0.11 mmol) was dissolved in a mixed solvent of THF/H$_2$O (1:1, v/v, 2.0 mL), and bromosuccinimide (58.7 mg, 0.33 mmol) was added. The reaction solution was stirred at room temperature for 5 h. After the reaction raw materials disappeared, the reaction solution was diluted with DCM. The organic phase was washed with 10% Na$_2$S$_2$O$_3$ and NaHCO$_3$ solutions respectively, dried over anhydrous Na$_2$SO$_4$, filtered and concentrated. The crude product was purified by column chromatography to prepare an acetal product intermediate (55.7 mg). The acetal product intermediate was dissolved in dry DCM (2.0 mL), and N-phenyltrifluoroacetyl chloride (82.1 µl, 0.55 mmol) and DBU (49.0 µl, 0.33 mmol) were added at 0° C. The reaction solution was stirred at room temperature for 3 h. After TLC monitored that the reaction raw materials completely disappeared, the reaction solution was diluted with DCM and washed with a saturated NaHCO$_3$ solution. The organic phase was dried over anhydrous Na$_2$SO$_4$, filtered and directly concentrated. The crude product was purified by silica gel column chromatography (petroleum ether/ethyl acetate, 6:1) to prepare the compound 8* (70.2 mg, 0.096 mmol, 87%). $^1$H NMR (400 MHz, CDCl$_3$) δ7.96-7.84 (m, 2H, Ar), 7.63-6.92 (m, 16H, Ar), 6.62-6.53 (m, 2H, Ar), 5.80 (s, 1H, H-1), 5.62 (d, J=3.2 Hz, 1H, H-4), 5.57-5.48 (m, 1H, H-2), 4.58 (d, J=12.7 Hz, 1H, ArCH$_2$), 4.48 (s, 2H, ArCH$_2$), 4.34 (d, J=12.7 Hz, 1H, ArCH$_2$), 3.66-3.49 (m, 4H), 2.86-2.54 (m, 4H, CH$_2$CH$_2$), 2.12 (s, 1H, CH$_3$). $^{13}$C NMR (101 MHz, CDCl$_3$) δ206.3, 171.9, 165.0, 143.1, 137.6, 137.0, 133.3, 129.9, 129.5, 129.4, 128.7, 128.4, 128.4, 128.3, 128.2, 128.0, 127.9, 127.8, 124.4, 119.2, 95.1 (C-1), 76.0, 73.8, 73.6, 70.9, 70.2, 67.6, 66.0, 38.1, 29.8, 28.1.

Example 6

Figure 7A:
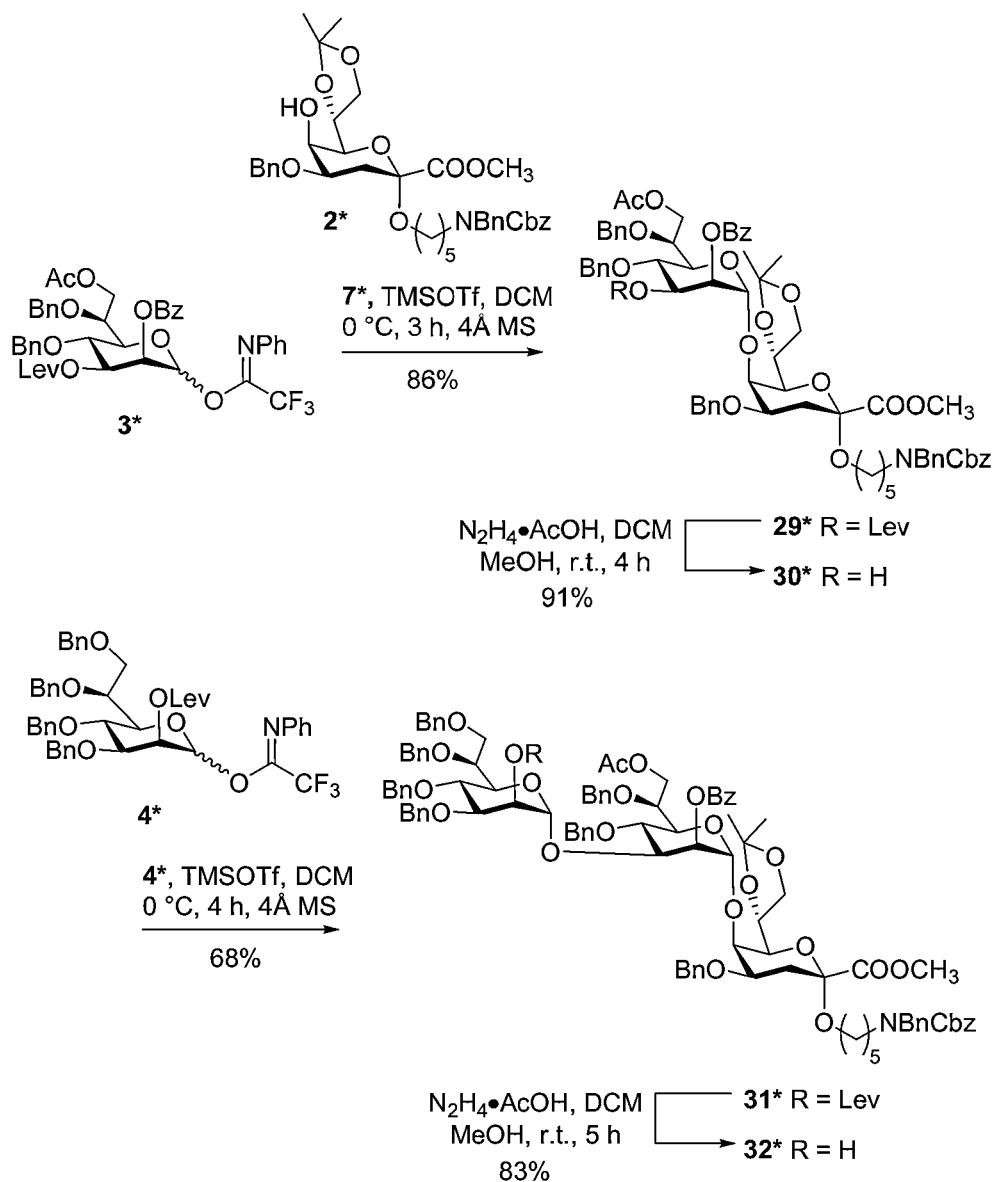
FIG. 7A-B shows the synthesis route of pentasaccharide 36*.
Figure 7B:
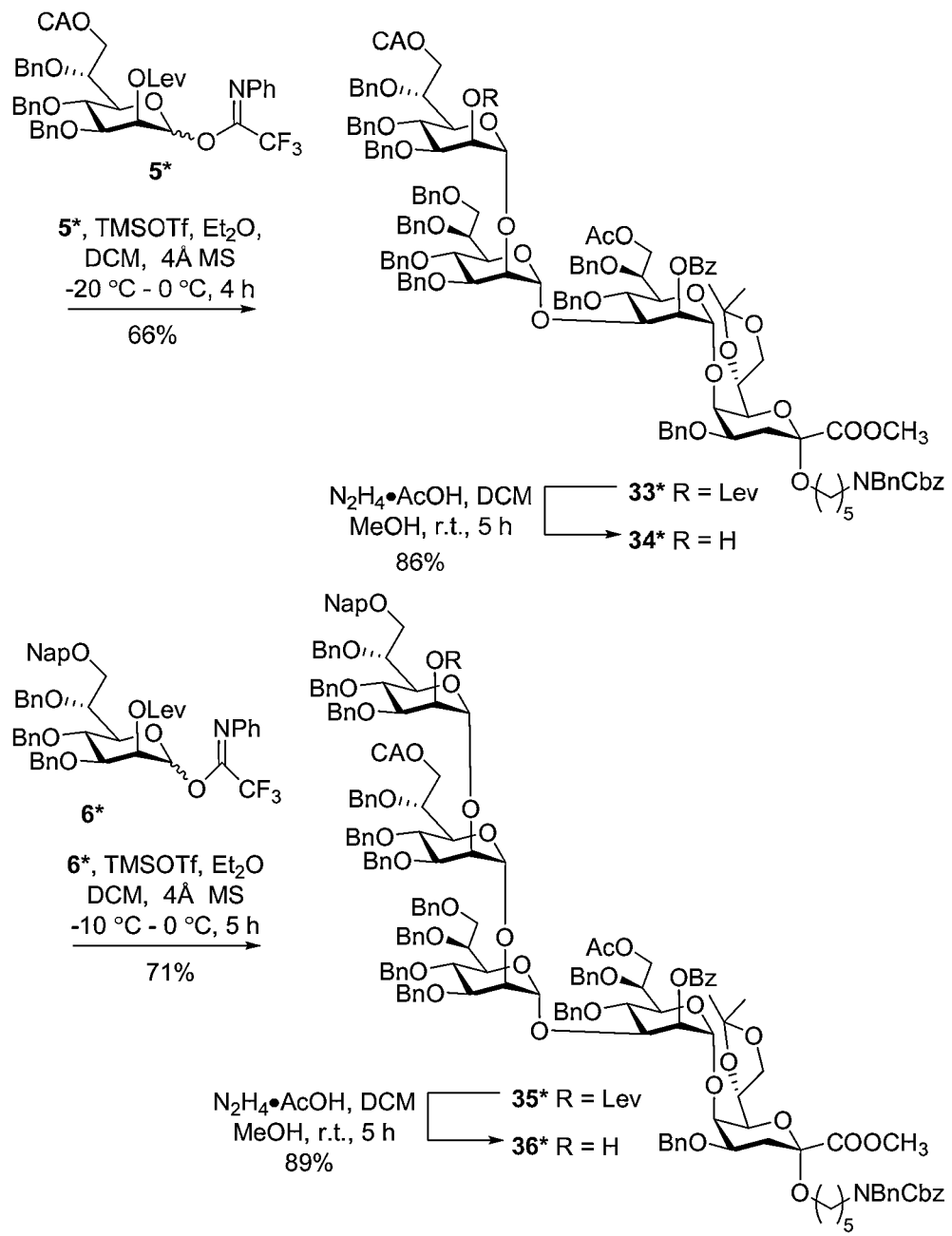

Pentasaccharide was synthesized as shown in FIG. 7:

An L,D-heptose donor 3* and a glycosyl receptor 2* underwent a glycosylation reaction under the catalysis of TMSOTf, successfully preparing structurally singular α-configuration disaccharide 29*, with a yield of 86%. The acetylpropionyl was selectively removed from the disaccharide 29* under hydrazine acetate, exposing the C3 hydroxyl to prepare a disaccharide receptor 30*, with a yield of 91%. A glycosyl donor 4* and the glycosyl receptor 30* further underwent a glycosylation reaction under the catalysis of TMSOTf to prepare a structurally singular α-configuration trisaccharide compound 31*, with a yield of 68%, wherein the coupling constants of C1 and H1 of two L,D-heptose glycosidic bonds in the trisaccharide are 175.5 Hz and 172.0 Hz respectively. The acetylpropionyl was selectively removed from the trisaccharide 31* using hydrazine acetate to prepare a glycosyl receptor 32*, with a yield of 83%. The D,D-heptose donor 5* and the trisaccharide receptor 32* underwent a glycosylation reaction under the catalysis of TMSOTf to prepare a structurally singular tetrasaccharide compound 33* (new glycosidic bond: $^2J_{H1/C1}$=174.0 Hz, $δ_{H1}$=4.66 ppm), with a yield of 66%. The acetylpropionyl protecting group was removed from the tetrasaccharide 33* under hydrazine acetate to prepare a tetrasaccharide receptor 34*, with a yield of 86%. The acetylpropionyl was selectively removed from the compound 35* under hydrazine acetate to prepare a compound 36*, with a yield of 89%.

Compound 29*: The glycosyl donor 3* (1.7 g, 2.11 mmol) and the glycosyl receptor 2* (1.12 g, 1.62 mmol) were azeotroped with toluene three times and dissolved in anhydrous DCM (10.5 mL). Molecular sieves 4 Å MS were added and the mixture was stirred for 30 min. The temperature of the reaction solution was reduced to 0° C. and TMSOTf (57.9 µl, 0.32 mmol) was added. The reaction solution was stirred at 0° C. for 4 h. After TLC detected that the glycosyl donor completely disappeared in the reaction, the reaction was terminated using pyridine. After the molecular sieves were filtered out, the filtrate was washed with NaHCO$_3$, and the organic phase was dried over anhydrous Na$_2$SO$_4$. The filtered and concentrated crude product was purified by silica gel column chromatography (petroleum ether/ethyl acetate, 4:1) to prepare the compound 29* (1.8 g, 1.30 mmol, 86%). $[\alpha]^{22}_C$=3.2 (c 1.0, CHCl$_3$); $^1$H NMR (400 MHz, CDCl$_3$) δ8.09-7.91 (m, 2H, Ar), 7.60-7.51 (m, 1H, Ar), 7.44-7.09 (m, 27H), 5.61 (dd, J=3.3, 1.8 Hz, 1H, H-2b), 5.56 (dd, J=9.7, 3.3 Hz, 1H, H-3b), 5.30 (d, J=2.2 Hz, 1H, H-1b), 5.18 (d, J=12.6 Hz, 2H, ArCH$_2$), 4.84 (d, J=11.7 Hz, 1H, ArCH$_2$), 4.65 (d, J=11.2 Hz, 2H, ArCH$_2$), 4.54-4.35 (m, 7H), 4.31 (ddd, J=9.2, 6.2, 4.9 Hz, 1H, H-6b), 4.27-4.19 (m, 2H, H-4b, H-8a), 4.14 (d, J=2.6 Hz, 1H, H-5a), 3.97 (dd, J=12.1, 2.9 Hz, 1H, H-8a'), 3.89 (s, 1H, H-6a), 3.79 (s, 4H, OCH$_3$, H-4a), 3.45-3.13 (m, 5H, H-3a, OCH$_2$, NCH$_2$), 2.76-2.37 (m, 4H, CH$_2$CH$_2$), 2.37-2.30 (m, 1H, H-2a(e)), 2.08 (s, 3H, CH$_3$), 2.06 (t, J=12.1 Hz, 1H, H-2a(a)), 1.98 (s, 3H, Ac), 1.57-1.46 (m, 4H, CH$_2$CH$_2$), 1.33 (s, 3H, CH$_3$), 1.29-1.18 (m, 5H, CH$_3$, CH$_2$). $^{13}$C NMR (101 MHz, CDCl$_3$) δ206.4, 206.3, 171.7, 170.6, 168.6, 165.5, 138.9, 138.5, 138.1, 137.9, 137.0, 133.3, 130.0, 129.9, 128.7, 128.6, 128.5, 128.4, 128.4, 128.3, 128.1, 128.0, 127.7, 127.7, 127.7, 127.6, 127.4, 109.8, 99.0, 97.7 (C-1b), 75.0, 74.7, 74.5, 73.2, 72.9, 72.7, 72.4, 72.2, 72.1, 70.6, 70.3, 68.1, 67.3, 66.6, 63.7, 52.6, 52.6, 50.7, 50.4, 47.2, 46.3, 38.0, 32.0, 29.8, 29.8, 29.4, 28.2, 27.0, 24.8, 23.6; HRMS (ESI) m/z calcd for C$_{74}$H$_{85}$O$_{20}$NNa [M+Na]$^+$ 1330.5557, found 1330.5549.

Compound 30*: The compound 29* (102 mg, 0.078 mmol) was dissolved in a mixed solvent of DCM/MeOH (15:1, v/v, 3.9 mL), and hydrazine acetate (15.2 mg, 0.15 mmol) was added at room temperature. The reaction solution was stirred at room temperature for 4 h. After the reaction was complete, the reaction solution was diluted with DCM, and the organic phase was washed with NaHCO$_3$, dried over anhydrous Na$_2$SO$_4$, filtered and concentrated. The crude product was separated and purified by silica gel column chromatography (petroleum ether/ethyl acetate, 4:1) to prepare the compound 30* (85.9 mg, 0.71 mmol, 91%). $[\alpha]^{22}_D$=6.82 (c 1.0, CHCl$_3$); $^1$H NMR (400 MHz, CDCl$_3$) δ8.03-7.89 (m, 2H, Ar), 7.59-7.50 (m, 1H, Ar), 7.40-7.16 (m, 27H, Ar), 5.48 (dd, J=3.4, 1.7 Hz, 1H, H-2b), 5.34 (d, J=1.7 Hz, 1H, H-1b), 5.18 (d, J=12.5 Hz, 2H, ArCH$_2$), 4.84 (d, J=11.4 Hz, 2H, ArCH$_2$), 4.68 (d, J=11.5 Hz, 1H, ArCH$_2$), 4.53-4.44 (m, 5H, ArCH$_2$), 4.44-4.27 (m, 4H, H-7b, H-3b, H-6b, H-5b), 4.24 (dd, J=8.5, 6.2 Hz, 1H, H-8a), 4.14 (d, J=2.7 Hz, 1H, H-5a), 4.06 (t, J=9.6 Hz, 1H, H-4b), 3.96 (dd, J=12.3, 2.3 Hz, 1H, H-7b'), 3.88 (s, 1H, H-6a), 3.82-3.72 (m, 5H, OCH3, H-8a', H-4a), 3.43-3.16 (m, 5H, H-3a, OCH$_2$, NCH$_2$), 2.32 (dd, J=12.4, 4.1 Hz, 1H), 2.04 (d, J=5.9 Hz, 1H), 1.97 (s, 4H), 1.51 (s, 6H), 1.32 (s, 3H), 1.30-1.21 (m, 6H). $^{13}$C NMR (101 MHz, CDCl$_3$) δ170.6, 168.7, 166.2, 139.0, 138.8, 138.1, 138.0, 133.3, 130.0, 129.9, 128.7, 128.6, 128.6, 128.5, 128.5, 128.4, 128.3, 128.1, 128.0, 127.9, 127.8, 127.7, 127.7, 127.6, 127.4, 109.9, 99.0, 97.3 (C-1b), 76.0, 75.3, 74.9, 74.6, 73.0, 72.9, 72.4, 72.3, 72.0, 70.9, 70.4, 68.2, 67.3, 67.0, 63.7, 52.6, 47.3, 32.1, 29.8, 29.4, 27.0, 24.9, 23.6, 21.2; HRMS (ESI) m/z calcd for C$_{69}$H$_{79}$O$_{18}$NNa [M+Na]$^+$ 1232.5189, found 1232.5186.

Compound 31*: The heptose donor 4* (71.0 mg, 0.084 mmol) and the glycosyl receptor 30* (75 mg, 0.067 mmol) were azeotroped with toluene three times and dissolved in anhydrous DCM (4.2 mL). Molecular sieves 4 Å MS were added, and the mixture was stirred for 30 min. The temperature of the reaction solution was reduced to 0° C. and TMSOTf (2.3 μL, 12.6 μmol) was added. The reaction solution was stirred at 0° C. for 4 h. After TLC detected that the reaction raw materials completely disappeared, the reaction was terminated using pyridine. After the molecular sieves were filtered out, the filtrate was washed with NaHCO$_3$, dried over anhydrous Na$_2$SO$_4$, filtered and concentrated. The crude product was purified by silica gel column chromatography (petroleum ether/ethyl acetate, 3:1) to prepare the compound 31* (86 mg, 0.047 mmol, 68%). $[\alpha]^{22}_D$=5.4 (c 1.0, CHCl$_3$); $^1$H NMR (400 MHz, CDCl$_3$) δ8.05-7.92 (m, 2H, Ar), 7.58-7.50 (m, 1H, Ar), 7.45-6.84 (m, 47H, Ar), 5.52 (dd, J=3.1, 1.8 Hz, 1H, H-2b), 5.38 (d, J=1.8 Hz, 1H, H-1b), 5.40-5.33 (m, 1H, H-2c), 5.26 (d, J=1.8 Hz, 1H, H-1c), 5.18 (d, J=13.2 Hz, 2H, ArCH$_2$), 4.85-4.77 (m, 3H, ArCH$_2$), 4.76-4.67 (m, 2H, ArCH$_2$), 4.57 (s, 2H), 4.51 (d, J=5.0 Hz, 2H, ArCH$_2$), 4.47-4.13 (m, 13H), 4.07-3.97 (m, 2H), 3.94-3.87 (m, 4H), 3.83 (dd, J=12.6, 2.1 Hz, 1H, H-4b), 3.77 (dd, J=8.5, 5.0 Hz, 1H, H-4c), 3.75-3.67 (m, 4H, OCH$_3$, H-8a'), 3.62 (dt, J=8.6, 2.0 Hz, 1H), 3.44-3.18 (m, 5H, H-3a, NCH$_2$, OCH$_2$), 2.67-2.52 (m, 4H, CH$_2$CH$_2$), 2.40 (d, J=12.3 Hz, 1H, H-2a(e)), 2.11-2.04 (m, 4H, H-2a(a), OCH$_3$), 1.94 (s, 3H, Ac), 1.56-1.46 (m, 4H, CH$_2$CH$_2$), 1.31 (s, 3H, CH$_3$), 1.23-1.20 (s, 5H, CH$_3$, CH$_2$). $^{13}$C NMR (101 MHz, CDCl$_3$) δ206.3, 171.7, 170.5, 168.3, 165.6, 139.1, 139.0, 139.0, 138.7, 138.5, 138.1, 137.9, 137.8, 137.0, 133.2, 130.2, 130.0, 128.7, 128.6, 128.5, 128.4, 128.4, 128.4, 128.4, 128.3, 128.3, 128.3, 128.1, 128.0, 127.9, 127.8, 127.7, 127.7, 127.6, 127.6, 127.5, 127.5, 127.4, 109.9, 100.2 (C-1c), 99.0, 96.7 (C-1b), 78.0, 75.3, 75.1, 75.0, 74.9, 74.8, 74.2, 73.9, 73.2, 73.1, 72.7, 72.5, 72.3, 71.8, 71.4, 71.2, 70.5, 69.2, 68.0, 67.3, 52.5, 38.1, 31.9, 29.9, 29.5, 28.2, 27.0, 24.8, 23.6, 21.2; HRMS (ESI) m/z calcd for C$_{109}$H$_{121}$O$_{26}$NNa [M+Na]$^+$ 1882.8069, found 1882.8057.

Compound 32*: The compound 31* (67 mg, 0.036 mmol) was dissolved in a mixed solvent of DCM/MeOH (10:1, v/v, 1.8 mL), and hydrazine acetate (6.6 mg, 0.072 mmol) was added at room temperature. The reaction solution was stirred at room temperature for 5 h. After TLC showed that the reaction was complete, the reaction solution was diluted with DCM, and the organic phase was washed with NaHCO$_3$, dried over anhydrous Na$_2$SO$_4$, filtered and concentrated. The crude product was separated and purified by silica gel column chromatography (petroleum ether/ethyl acetate, 3:1) to prepare the compound 32* (52.7 mg, 0.030 mmol, 83%). $[\alpha]^{22}_D$=10.7 (c 1.0, CHCl$_3$); $^1$H NMR (400 MHz, CDCl$_3$) δ8.07-7.93 (m, 2H, Ar), 7.54 (t, J=7.6 Hz, 1H, Ar), 7.44-7.04 (m, 47H, Ar), 5.52 (t, J=2.3 Hz, 1H, H-2b), 5.37 (d, J=1.8 Hz, 1H, H-1b), 5.25 (s, 1H, H-1c), 5.18 (d, J=12.7 Hz, 1H, ArCH$_2$), 4.86-4.75 (m, 2H, ArCH$_2$), 4.72-4.63 (m, 3H, ArCH$_2$), 4.57-4.48 (m, 4H, ArCH$_2$), 4.47-4.26 (m, 10H), 4.21-4.12 (m, 3H), 4.06-3.79 (m, 7H), 3.79-3.66 (m, 6H), 3.65-3.57 (m, 1H), 3.49-3.14 (m, 5H, H-3a, NCH$_2$, OCH$_2$), 2.37 (t, J=9.2 Hz, 1H, H-2a(e)), 2.15 (s, 1H, OH), 2.03 (t, J=12.1 Hz, 1H, H-2a(a)), 1.95 (s, 3H, Ac), 1.61-1.42 (m, 4H, CH$_2$CH$_2$), 1.30 (s, 3H, CH$_3$), 1.28-1.16 (m, 5H, CH$_3$, CH$_2$). $^{13}$C NMR (101 MHz, CDCl$_3$) δ170.4, 168.2, 165.4, 139.0, 138.9, 138.7, 138.5, 137.9, 133.0, 130.2, 129.9, 128.5, 128.4, 128.4, 128.3, 128.2, 128.2, 128.2, 128.1, 128.0, 128.0, 127.9, 127.8, 127.8, 127.6, 127.5, 127.4, 127.4, 127.4, 127.3, 127.2, 109.8, 102.1 (C-1c), 98.9, 96.7 (C-1b), 79.9, 75.1, 74.8, 74.0, 73.6, 72.9, 72.8, 72.5, 71.9, 70.3, 68.8, 67.9, 67.2, 63.5, 52.4, 29.3, 26.8, 24.6, 23.5, 21.0; HRMS (ESI) m/z calcd for C$_{104}$H$_{115}$O$_{24}$NNa [M+Na]$^+$ 1784.7701, found 1784.7689.

Compound 33*: The glycosyl donor 5* (43.8 mg, 0.053 mmol) and the glycosyl receptor 32* (78.1 mg, 0.044 mmol) were co-evaporated with toluene three times, and anhydrous DCM (2.0 mL) and 4 Å molecular sieves were added. The mixture was stirred at room temperature for 30 min, and then the temperature of the reaction solution was reduced to −20° C. TMSOTf (1.43 μL, 7.9 μmol) was added to the reaction flask, and the reaction solution was slowly heated to 0° C. and stirred for a total of 4 h. After TLC monitored that the glycosyl donor completely disappeared, the reaction was terminated by adding pyridine. After the molecular sieves were filtered out from the reaction solution, the reaction solution was washed with NaHCO$_3$, and the organic phase was dried over Na$_2$SO$_4$, filtered and concentrated. The crude product was separated and purified by a silica gel chromatography column (petroleum ether/ethyl acetate, 6:1) to prepare the compound 33* (71.2 mg, 0.038 mmol, 66%). $[\alpha]^{22}_C$=15.6 (c 1.0, CHCl$_3$); $^1$H NMR (400 MHz, CDCl$_3$) δ8.04 (d, J=7.7 Hz, 2H, Ar), 7.56 (t, J=7.4 Hz, 1H, Ar), 7.46-6.89 (m, 62H, Ar), 5.51 (d, J=2.7 Hz, 1H, H-2b), 5.43 (d, J=4.6 Hz, 2H, H-1d, H-2d, H-1c), 5.38 (s, 1H, H-1b), 5.18 (d, J=10.6 Hz, 2H, ArCH$_2$), 4.84-4.69 (m, 5H, ArCH$_2$), 4.66 (d, J=1.7 Hz, 1H, H-1d), 4.62-4.42 (m, 9H), 4.41-4.20 (m, 9H), 4.16-4.06 (m, 5H), 4.03-3.83 (m, 5H), 3.80-3.74 (m, 2H), 3.74-3.64 (m, 4H), 3.80-3.52 (m, 2H), 3.38 (s, 3H, OCH$_3$), 3.36-3.16 (m, 5H, OCH$_2$, NCH$_2$), 2.76-2.59 (m, 4H, CH$_2$CH$_2$), 2.13 (s, 4H, CH$_3$, H-2a(e)), 1.93 (s, 3H, Ac), 1.86 (t, J=12.1 Hz, 1H, H-2a(a)), 1.55-1.41 (m, 4H, CH$_2$CH$_2$), 1.32-1.15 (m, 8H, CH$_2$, OCH$_3$, OCH$_3$); HRMS (ESI) m/z calcd for C$_{139}$H$_{152}$O$_{33}$ClNNa [M+Na]$^+$ 2397.99, found 2397.85.

Compound 34*: The compound 33* (58.0 mg, 0.024 mmol) was dissolved in a mixed solvent of DCM/MeOH (10:1, v/v, 1.2 mL), and hydrazine acetate (4.4 mg, 0.048 mmol) was added at room temperature. The reaction solution was stirred at room temperature for 5 h. After TLC showed that the reaction was complete, the reaction solution was diluted with DCM, and the organic phase was washed with NaHCO$_3$, dried over anhydrous Na$_2$SO$_4$, filtered and concentrated. The crude product was separated and purified by silica gel column chromatography (petroleum ether/ethyl acetate, 3:1) to prepare the compound 34* (47.0 mg, 0.021 mmol, 86%). $[\alpha]^{22}_D$=13.2 (c 1.0, CHCl$_3$); $^1$H NMR (400 MHz, CDCl$_3$) δ7.97-7.91 (m, 2H, Ar), 7.48 (t, J=7.4 Hz, 1H, Ar), 7.35-6.80 (m, 62H, Ar), 5.43 (dd, J=3.2, 1.7 Hz, 1H, H-2b), 5.40 (s, 1H, H-1c), 5.31 (d, J=1.7 Hz, 1H, H-1b), 5.10 (d, J=10.8 Hz, 2H, ArCH$_2$), 4.82-4.71 (m, 2H, ArCH$_2$), 4.72-4.59 (m, 4H, H-1d), 4.52-4.36 (m, 10H), 4.35-4.14 (m, 9H), 4.11-3.97 (m, 8H), 3.95-3.85 (m, 4H), 3.82-3.56 (m, 11H), 3.54-3.49 (m, 2H), 3.36 (s, 3H, OCH$_3$), 3.30-3.02 (m, 5H, OCH$_2$, NCH$_2$), 2.08-2.02 (m, 1H, H-2a(e)), 1.97 (s, 3H, Ac), 1.78 (t, J=12.3 Hz, 1H, H-2a(a)), 1.48-1.32 (m, 4H, CH$_2$CH$_2$), 1.30-1.01 (m, 8H, CH$_2$, OCH$_3$, OCH$_3$). $^{13}$C NMR (101 MHz, CDCl$_3$) δ170.5, 168.1, 167.0, 165.7, 139.5, 139.2, 139.0, 138.7, 138.3, 138.3, 138.1, 138.0, 137.7, 133.2, 130.3, 130.0, 128.7, 128.6, 128.6, 128.5, 128.5, 128.5, 128.4, 128.4, 128.3, 128.3, 128.1, 128.0, 128.0, 127.9, 127.6, 127.4, 127.3, 109.9, 99.0, 96.8, 80.8, 75.7, 75.4, 75.1, 74.9, 74.2, 73.8, 73.1, 72.7, 72.4, 72.2, 72.2, 71.8, 71.5, 71.2, 70.9, 70.4, 68.4, 68.0, 67.3, 66.0, 63.6, 62.1, 52.4, 40.8, 31.9, 31.8, 29.4, 27.0, 24.8, 23.6, 21.2, 19.4, 14.1; HRMS (ESI) m/z calcd for C$_{134}$H$_{146}$O$_{31}$ClNNa [M+Na]$^+$ 2322.9460, found 2322.9447.

Compound 35*: The glycosyl donor 6* (42.0 mg, 0.053 mmol) and the glycosyl receptor 34* (41.4 mg, 0.018 mmol) were co-evaporated with toluene three times, and anhydrous DCM (3.9 mL) and 4 Å molecular sieves were added. The mixture was stirred at room temperature for 30 min, and then the temperature of the reaction solution was reduced to −10° C. TMSOTf (2.1 μL, 11.7 μmol) was added to the reaction flask, and the reaction solution was slowly heated to 0° C. and stirred for a total of 5 h. After TLC monitored that the glycosyl donor completely disappeared, the reaction was terminated by adding pyridine. After the molecular sieves were filtered out from the reaction solution, the reaction solution was washed with NaHCO$_3$, and the organic phase was dried over anhydrous Na$_2$SO$_4$, filtered and concentrated. The crude product was separated and purified by a silica gel chromatography column (petroleum ether/ethyl acetate, 3:1) to prepare the compound 35* (39.2 mg, 0.013 mmol, 71%). $[\alpha]^{22}_D$=34.4 (c 1.0, CHCl$_3$); $^1$H NMR (400 MHz, CDCl$_3$) δ8.07 (d, J=7.8 Hz, 2H, Ar), 7.87-7.54 (m, 6H, Ar), 7.50-6.95 (m, 79H), 5.63-5.55 (m, 2H, H-1c, H-2b), 5.51 (s, 1H, H-2d), 5.41 (s, 1H, H-1b), 5.21 (d, J=9.9 Hz, 2H, ArCH$_2$), 5.09-4.94 (m, 2H, H-1d, H-1e), 4.93-4.68 (m, 7H), 4.67-4.25 (m, 15H), 4.39-4.26 (m, 7H), 4.24-4.06 (m, 5H), 4.03-3.70 (m, 15H), 3.69-3.52 (m, 5H), 3.41 (s, 3H, OCH$_3$), 3.26 (d, J=26.1 Hz, 5H, CH$_2$CH$_2$), 2.75-2.51 (m, 4H, CH$_2$CH$_2$), 2.18-2.06 (m, 4H, CH$_3$, H-2a(e)), 1.96 (s, 3H, Ac), 1.88 (t, J=12.2 Hz, 1H, H-2a(a)), 1.59-1.48 (m, 4H, CH$_2$CH$_2$), 1.40-1.10 (m, 8H, CH$_2$, OCH$_3$, OCH$_3$). $^{13}$C NMR (101 MHz, CDCl$_3$) δ206.1, 171.7, 170.5, 168.1, 166.7, 165.6, 139.4, 139.2, 139.1, 139.0, 138.9, 138.5, 138.5, 138.4, 138.3, 138.3, 138.2, 138.0, 137.6, 136.1, 133.4, 133.1, 133.0, 130.3, 130.0, 128.8, 128.7, 128.6, 128.5, 128.5, 128.4, 128.4, 128.3, 128.3, 128.3, 128.2, 128.2, 128.1, 128.1, 128.0, 128.0, 127.9, 127.8, 127.8, 127.7, 127.7, 127.6, 127.6, 127.5, 127.4, 127.4, 127.3, 127.3, 127.2, 126.1, 126.1, 125.8, 125.6, 109.9, 101.4 (H-1c), 101.3 (H-1d), 99.0 (H-1e), 96.8 (H-1b), 80.5, 78.7, 78.5, 75.6, 75.4, 75.3, 75.0, 75.0, 74.8, 74.3, 74.2, 73.6, 73.4, 73.2, 73.1, 72.9, 72.7, 72.4, 72.3, 72.2, 71.9, 71.7, 71.4, 71.1, 70.6, 70.4, 68.7, 68.0, 67.5, 67.3, 66.0, 63.6, 52.4, 50.6, 50.4, 47.2, 46.3, 40.8, 38.1, 32.1, 31.8, 29.8, 29.6, 29.4, 29.2, 28.2, 27.7, 27.0, 24.9, 24.7, 23.6, 22.8, 21.2, 14.3; Maldi-TOf m/z calcd for C$_{178}$H$_{190}$O$_{39}$ClNNa [M+Na]$^+$ 3023.2496, found 3023.277.

Compound 36*: The compound 35* (101 mg, 0.034 mmol) was dissolved in a mixed solvent of DCM/MeOH (10:1, v/v, 2.0 mL), and hydrazine acetate (6.3 mg, 0.068 mmol) was added at room temperature. The reaction solution was stirred at room temperature for 5 h. After TLC showed that the reaction raw materials completely disappeared, the reaction solution was diluted with DCM, and the organic phase was washed with NaHCO$_3$, dried over anhydrous Na$_2$SO$_4$, filtered and concentrated. The crude product was separated and purified by silica gel column chromatography (petroleum ether/ethyl acetate, 3:1) to prepare the compound 36* (87.9 mg, 0.03 mmol, 89%). $[\alpha]^{22}_D$=24.1 (c 1.0, CHCl$_3$); $^1$H NMR (400 MHz, CDCl$_3$) δ8.09-8.02 (m, 2H, Ar), 7.81-7.49 (m, 6H, Ar), 7.48-6.92 (m, 79H), 5.62 (s, 1H, H-1c), 5.56 (d, J=2.6 Hz, 1H, H-2b), 5.39 (d, J=1.7 Hz, 1H, H-1b), 5.19 (d, J=10.5 Hz, 1H, ArCH$_2$), 5.11-5.05 (m, 1H, H-1d, H-1e), 4.88-4.67 (m, 7H), 4.65-4.40 (m, 18H), 4.40-4.24 (m, 9H), 4.24-4.02 (m, 11H), 4.00-3.81 (m, 14H), 3.80-3.70 (m, 5H), 3.69-3.54 (m, 6H), 3.51 (t, J=6.6 Hz, 1H), 3.37 (s, 3H, OCH$_3$), 3.31-3.18 (m, 5H), 2.14-2.06 (m, 1H, H-2a(e)), 1.95 (s, 3H, Ac), 1.86 (t, J=12.1 Hz, 1H, H-2a(a)), 1.59-1.47 (m, 4H, CH$_2$CH$_2$), 1.39-1.14 (m, 8H, CH$_2$, OCH$_3$, OCH$_3$). $^{13}$C NMR (101 MHz, CDCl$_3$) δ170.6, 168.1, 166.9, 165.6, 139.3, 139.2, 139.1, 138.8, 138.5, 138.5, 138.3, 138.3, 138.1, 138.1, 137.6, 136.0, 133.4, 133.2, 133.0, 130.2, 130.0, 128.7, 128.6, 128.6, 128.5, 128.4, 128.4, 128.3, 128.3, 128.3, 128.2, 128.1, 128.1, 128.0, 128.0, 128.0, 128.0, 127.8, 127.7, 127.6, 127.6, 127.5, 127.4, 127.3, 127.3, 127.3, 127.2, 126.2, 126.1, 125.8, 125.7, 109.9, 101.5, 101.1, 99.0, 96.8, 80.5, 78.4; Maldi-TOf m/z calcd for C$_{173}$H$_{184}$O$_{37}$ClNNa [M+Na]$^+$ 2925.2128, found 2925.262.

Example 7

Figure 8:
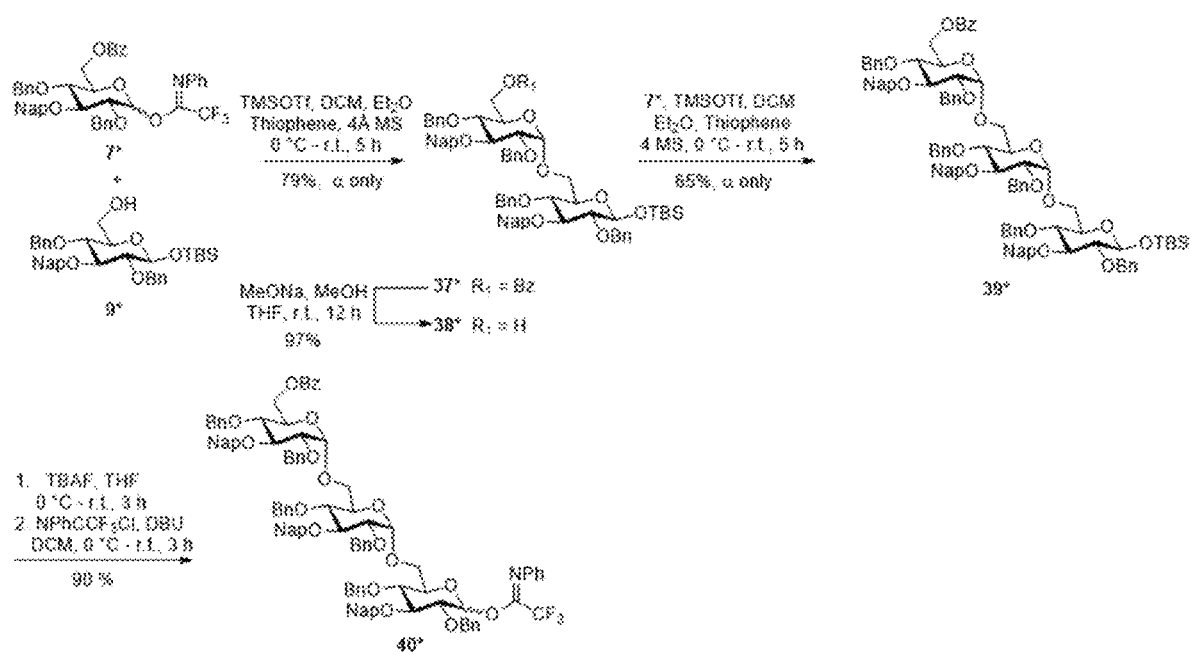
FIG. 8 shows the synthesis route of trisaccharide 40*.

Trisaccharide was synthesized as shown in FIG. 8:

A glycosyl donor 7* and a glycosyl receptor 9* underwent a glycosylation reaction under a synergistic glycosylation strategy to prepare singular α-configuration disaccharide 37* (new glycosidic bond: $^3J_{H1/H2}$=3.5 Hz, δ$_{H1}$=5.01 ppm), with a yield of 79%. The disaccharide 37* was treated with sodium methoxide to remove benzoyl to prepare a disaccharide receptor 38*, with a yield of 65%. The glycosyl donor 7* reacted with the receptor 38* under a synergistic glycosylation condition to prepare singular α-configuration trisaccharide 39* (new glycosidic bond: $^3J_{H1/H2}$=3.5 Hz, δ$_{H1}$=5.09 ppm), with a yield of 65%. The terminal TBS group was removed from the trisaccharide 39* in a buffer of TBAF and acetic acid, and phenyltrifluoroacetimidate was introduced into the hemiacetal intermediate under catalysis of DBU to obtain a trisaccharide donor 40*, with a two-step yield of 90%.

Compound 37*: The glycosyl donor 7* (1.47 g, 1.88 mmol) and the glycosyl receptor 9* (775 mg, 1.26 mmol) were dissolved in DCM/Et$_2$O (1:2, 94 mL). Thiophene and 4 Å molecular sieves were added and the mixture was stirred for half an hour. The temperature was reduced to 0° C., and TMSOTf (32 μL, 0.18 mmol) was added for conducting a catalytic glycosylation reaction. After the reaction was complete, the crude product was purified by a silica gel column (petroleum ether/ethyl acetate, 8:1) to prepare the compound 37* (1.2 g, 1.0 mmol, 79%). $[\alpha]^{22}_D$=44.8 (c 1.0, CHCl$_3$). $^1$H NMR (600 MHz, CDCl$_3$) δ8.08-7.13 (m, 39H, Ar), 5.16 (d, J=10.9 Hz, 1H, ArCH$_2$), 5.05 (d, J=11.2 Hz, 1H, ArCH$_2$), 5.01 (d, J=3.5 Hz, 1H, H-1a), 5.00-4.82 (m, 6H, ArCH$_2$), 4.73 (d, J=11.9 Hz, 1H, ArCH$_2$), 4.69 (d, J=7.5 Hz, 1H, H-1b), 4.65 (dd, J=11.0, 6.3 Hz, 3H, ArCH$_2$), 4.53 (dd, J=11.9, 2.2 Hz, 1H, H-6a), 4.49 (dd, J=11.9, 4.4 Hz, 1H, H-6a'), 4.13 (t, J=9.2 Hz, 1H, H-3a), 4.04 (ddd, J=10.1, 4.5, 2.2 Hz, 1H, H-5a), 3.88 (dd, J=11.5, 5.1 Hz, 1H, H-6b), 3.74-3.67 (m, 3H, H-3b, H-6b, H-4b), 3.65 (dd, J=10.0, 8.9 Hz, 1H, H-4a), 3.64 (dd, J=9.6, 3.5 Hz, 1H, H-2a), 3.55 (ddd, J=7.9, 3.6, 2.7 Hz, 1H, H-5b), 3.36-3.23 (m, 1H, H-2b), 0.93 (s, 9H, OTBS), 0.17 (s, 3H, $CH_3$), 0.16 (s, 3H, $CH_3$). $^{13}C$ NMR (151 MHz, $CDCl_3$) δ166.4, 138.6, 138.6, 138.4, 138.2, 136.4, 136.2, 133.5, 133.5, 133.2, 133.1, 133.1, 130.2, 129.8, 129.1, 128.8, 128.7, 128.6, 128.5, 128.5, 128.5, 128.5, 128.3, 128.2, 128.1, 128.1, 128.1, 127.9, 127.9, 127.8, 127.8, 127.7, 127.0, 126.5, 126.4, 126.1, 126.1, 125.9, 125.9, 98.3 (C-1b), 97.4 (C-1a), 84.8, 84.2, 81.8, 80.6, 78.0, 77.8, 76.0, 75.8, 75.2, 75.1, 74.9, 72.5, 69.1, 66.6, 63.6, 25.8, 18.1, −3.8, −4.9; HRMS (ESI) m/z calcd for $C_{75}H_{80}O_{12}SiNa$ $[M+Na]^+$ 1223.5311, found 1223.5302.

Compound 38*: The compound 37* (58.0 mg, 0.048 mmol) was treated with sodium methoxide (33 μL, 5 M) to remove an ester group. After the reaction was complete, the crude product was purified and separated by a silica gel column (petroleum ether/ethyl acetate, 5:1) to prepare the compound 38* (51.4 mg, 0.046 mmol, 97%). $[α]^{22}_D$=52.2 (c 1.0, $CHCl_3$); $^1H$ NMR (400 MHz, $CDCl_3$) δ7.69-7.03 (m, 34H, Ar), 4.97 (d, J=11.1 Hz, 1H, $ArCH_2$), 4.87 (d, J=10.5 Hz, 1H), 4.86 (d, J=3.0 Hz, 1H, H-1a), 4.83-4.67 (m, 6H, $ArCH_2$), 4.58-4.39 (m, 5H, $ArCH_2$), 3.92 (t, J=9.2 Hz, 1H, H-3a), 3.69 (dd, J=11.7, 4.7 Hz, 1H, H-6a), 3.64-3.47 (m, 6H), 3.44-3.37 (m, 2H, H-2a, H-4a), 3.35 (ddd, J=9.7, 4.7, 1.5 Hz, 1H, H-5b), 3.11 (dd, J=9.1, 7.5 Hz, 1H, H-2b), 1.50 (s, 1H, OH), 0.77 (s, 9H, OTBS), 0.01 (s, 3H, $CH_3$), −0.00 (s, 3H, $CH_3$). $^{13}C$ NMR (101 MHz, $CDCl_3$) δ138.6, 138.6, 138.5, 138.4, 136.3, 136.3, 133.4, 133.0, 133.0, 128.6, 128.5, 128.5, 128.2, 128.1, 128.0, 128.0, 127.9, 127.9, 127.8, 127.8, 127.8, 127.7, 127.7, 126.8, 126.5, 126.3, 126.1, 126.0, 125.9, 125.9, 98.3 (C-1b), 97.5 (C-1a), 84.7, 84.1, 81.5, 80.5, 77.7, 77.3, 75.7, 75.1, 75.1, 75.0, 72.4, 70.9, 66.3, 62.0, 25.8, 18.1, −3.8, −5.0; HRMS (ESI) m/z calcd for $C_{68}H_{76}O_{11}SiNa$ $[M+Na]^+$ 1119.5049, found 1119.5035.

Compound 39*: The glycosyl donor 7* (670 mg, 0.86 mmol) and the glycosyl receptor 38* (770 mg, 0.64 mmol) were dissolved in $DCM/Et_2O$ (1:2, 43 mL). Thiophene and 4 Å molecular sieves were added and the mixture was stirred for half an hour. The temperature was reduced to 0° C., and TMSOTf (16.2 μL, 0.09 mmol) was added for conducting a catalytic glycosylation reaction. After the reaction was complete, the crude product was purified by a silica gel column (petroleum ether/ethyl acetate, 8:1) to prepare the compound 39* (699 mg, 0.42 mmol, 65%). $[α]^{22}_D$=59.4 (c 1.0, $CHCl_3$); $^1H$ NMR (600 MHz, $CDCl_3$) δ8.02-7.97 (m, 2H, Ar), 7.84-7.65 (m, 10H, Ar), 7.57-7.52 (m, 1H, Ar), 7.51-7.35 (m, 14H, Ar), 7.33-7.19 (m, 22H, Ar), 5.16 (d, J=10.9 Hz, 1H, $ArCH_2$), 5.12 (d, J=11.1 Hz, 1H, $ArCH_2$), 5.09 (d, J=3.5 Hz, 1H, H-1a), 5.02 (d, J=11.1 Hz, 1H, $ArCH_2$), 5.02 (d, J=3.0 Hz, 2H, H-1b), 5.01-4.87 (m, 7H, $ArCH_2$), 4.79-4.75 (m, 2H, $ArCH_2$), 4.74-4.65 (m, 4H, $ArCH_2$), 4.64 (d, J=7.5 Hz, 1H, H-1c), 4.63-4.55 (m, 2H, $ArCH_2$), 4.52 (dd, J=12.0, 2.1 Hz, 1H, H-6a), 4.44 (dd, J=12.0, 4.4 Hz, 1H, H-6a'), 4.12 (t, J=9.2 Hz, 1H, H-3a), 4.08 (t, J=9.2 Hz, 1H, H-3b), 4.02 (ddd, J=10.2, 4.4, 2.1 Hz, 1H, H-5a), 3.91-3.85 (m, 3H, H-5b, H-6b, H-6c), 3.80-3.71 (m, 4H, H-4b, H-4c, H-6b', H-6c'), 3.67 (dd, J=9.2 Hz, 1H, H-3c), 3.64 (dd, J=10.1, 8.9 Hz, 1H, H-4a, H-2b), 3.61 (dd, J=9.6, 3.5 Hz, 1H, H-2b), 3.48 (dd, J=9.6, 3.5 Hz, 1H, H-2a), 3.48-3.42 (m, 1H, H-5c), 3.26 (dd, J=9.2, 7.5 Hz, 1H, H-2c), 0.93 (s, 9H, OTBS), 0.16 (s, 3H, $CH_3$), 0.16 (s, 3H, $CH_3$). $^{13}C$ NMR (151 MHz, $CDCl_3$) δ166.2, 138.7, 138.6, 138.5, 138.4, 138.0, 136.4, 136.3, 136.0, 133.3, 133.3, 133.0, 133.0, 132.9, 132.9, 130.0, 129.6, 128.4, 128.4, 128.4, 128.3, 128.3, 128.1, 128.0, 127.9, 127.9, 127.9, 127.8, 127.8, 127.7, 127.6, 127.6, 127.6, 127.5, 127.5, 127.4, 126.8, 126.7, 126.3, 126.2, 126.0, 125.9, 125.9, 125.8, 125.7, 125.7, 98.2 (C-1c), 97.3 (C-1b), 96.8 (C-1a), 84.5, 84.1, 81.8, 81.6, 80.6, 80.3, 77.7, 77.6, 75.8, 75.5, 75.1, 75.0, 74.9, 74.9, 72.2, 72.1, 70.7, 68.9, 66.1, 65.7, 63.5, 25.7, 17.9, −3.9, −5.1; HRMS (ESI) m/z calcd for $C_{106}H_{110}O_{17}SiNa$ $[M+Na]^+$ 1705.7404, found 1705.7399.

Compound 40*: The compound 39* (47.0 mg, 0.028 mmol) was dissolved in THF (1.5 mL) and acetic acid (16.0 μL, 0.28 mmol) was added at 0° C. Then a solution (0.28 mL, 0.28 mmol, 1 M) of tetrabutylammonium fluoride (TBAF) in THF was added. The reaction solution was stirred at room temperature for 3 h. After TLC monitored that the reaction was complete, the reaction solution was diluted with ethyl acetate and washed three times with water. The mixed organic phase was dried over anhydrous $Na_2SO_4$ and concentrated under reduced pressure. The crude product was separated and purified by a silica gel chromatography column to prepare a hemiacetal product intermediate (40.3 mg). The hemiacetal product intermediate was dissolved in dry DCM (0.5 mL), and the reaction solution was cooled to 0° C. N-phenyltrifluoroacetyl chloride (18.6 μL, 0.13 mmol) and DBU (11.2 μL, 0.075 mmol) were added, and the reaction solution was stirred at room temperature for 3 h. After the reaction was complete, the reaction solution was directly concentrated under reduced pressure, and the crude product was separated and purified by a silica gel chromatography column (petroleum ether/ethyl acetate, 3:1) to prepare the 40* (41.2 mg, 0.025 mmol, 90%). $^1H$ NMR (400 MHz, $CDCl_3$) δ8.06-7.97 (m, 2H, Ar), 7.90-7.66 (m, 12H, Ar), 7.60-7.15 (m, 40H), 7.08-7.01 (m, 1H, Ar), 6.88 (d, J=7.7 Hz, 1H, Ar), 5.20-5.08 (m, 3H, H-1a), 5.05-4.87 (m, 7H, H-1b), 4.82-4.59 (m, 8H), 4.57-4.49 (m, 1H), 4.47-4.40 (m, 1H), 4.13 (t, J=9.2 Hz, 1H), 4.09-3.97 (m, 2H), 3.94-3.72 (m, 7H), 3.72-3.59 (m, 2H), 3.53-3.39 (m, 2H). $^{13}C$ NMR (151 MHz, $CDCl_3$) δ166.2, 138.6, 138.5, 138.5, 138.4, 138.1, 138.0, 138.0, 137.8, 136.4, 136.4, 136.1, 136.0, 133.4, 133.3, 133.0, 133.0, 132.9, 130.0, 129.7, 129.4, 128.7, 128.5, 128.5, 128.5, 128.4, 128.4, 128.4, 128.4, 128.3, 128.1, 128.1, 128.0, 128.0, 128.0, 127.9, 127.9, 127.9, 127.8, 127.8, 127.8, 127.8, 127.7, 127.7, 127.7, 127.6, 127.6, 127.6, 127.5, 127.5, 127.4, 127.3, 127.3, 127.3, 127.2, 126.8, 126.8, 126.7, 126.6, 126.4, 126.3, 126.3, 126.2, 126.2, 126.1, 126.1, 126.0, 125.9, 125.9, 125.9, 125.8, 125.8, 125.8, 125.7, 120.4, 119.3, 97.4 (C-1b), 96.9 (C-1c), 81.8, 80.5, 80.3, 75.8, 75.8, 75.7, 75.7, 75.6, 75.6, 75.2, 75.1, 75.0, 72.3, 72.3, 72.2, 72.1, 71.0, 70.9, 70.8, 69.0, 69.0, 65.9, 65.6, 65.6, 65.3, 63.5, 63.4.

Example 8

Figure 9:
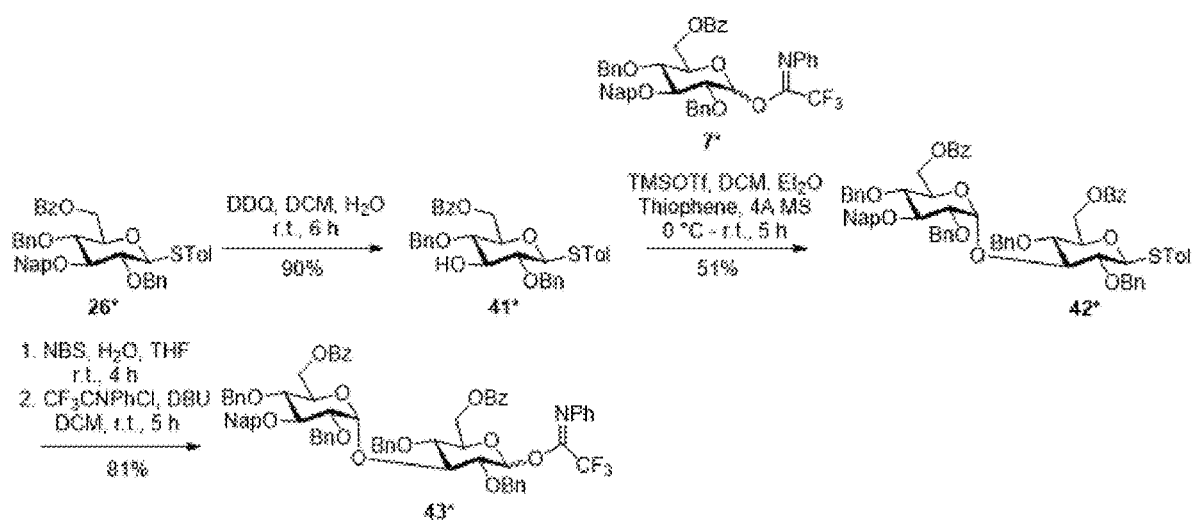
FIG. 9 shows the synthesis route of disaccharide 43*.
Figure 10A:
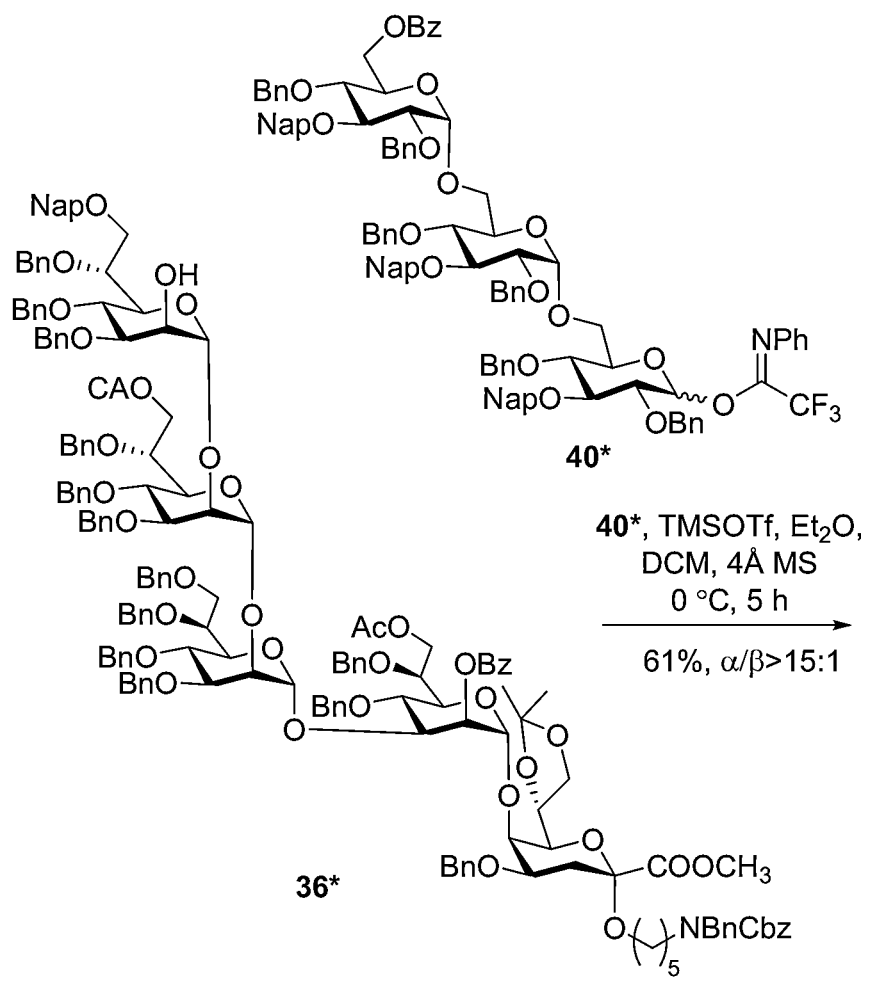
FIG. 10A-E shows the synthesis route of undecasaccharide 1.
Figure 10B:
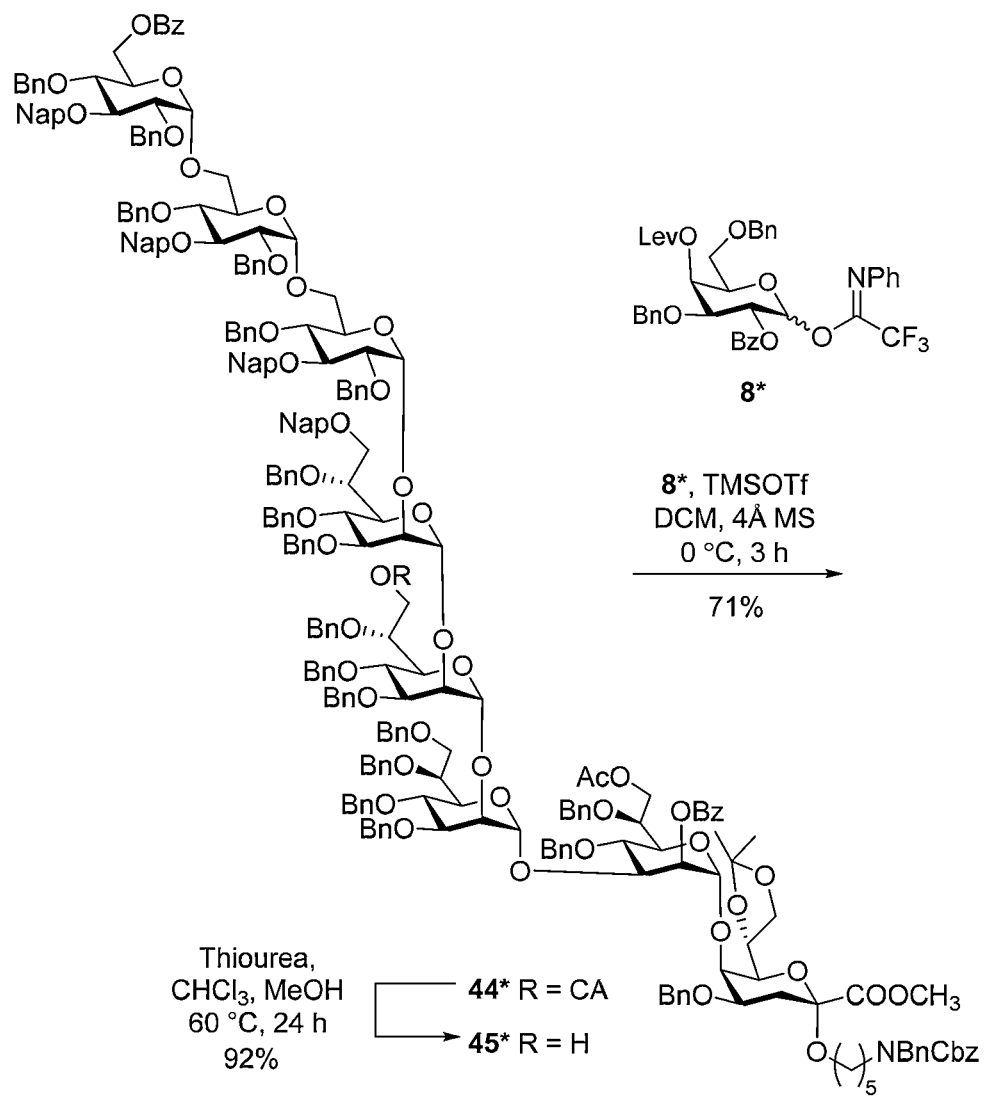
Figure 10C:
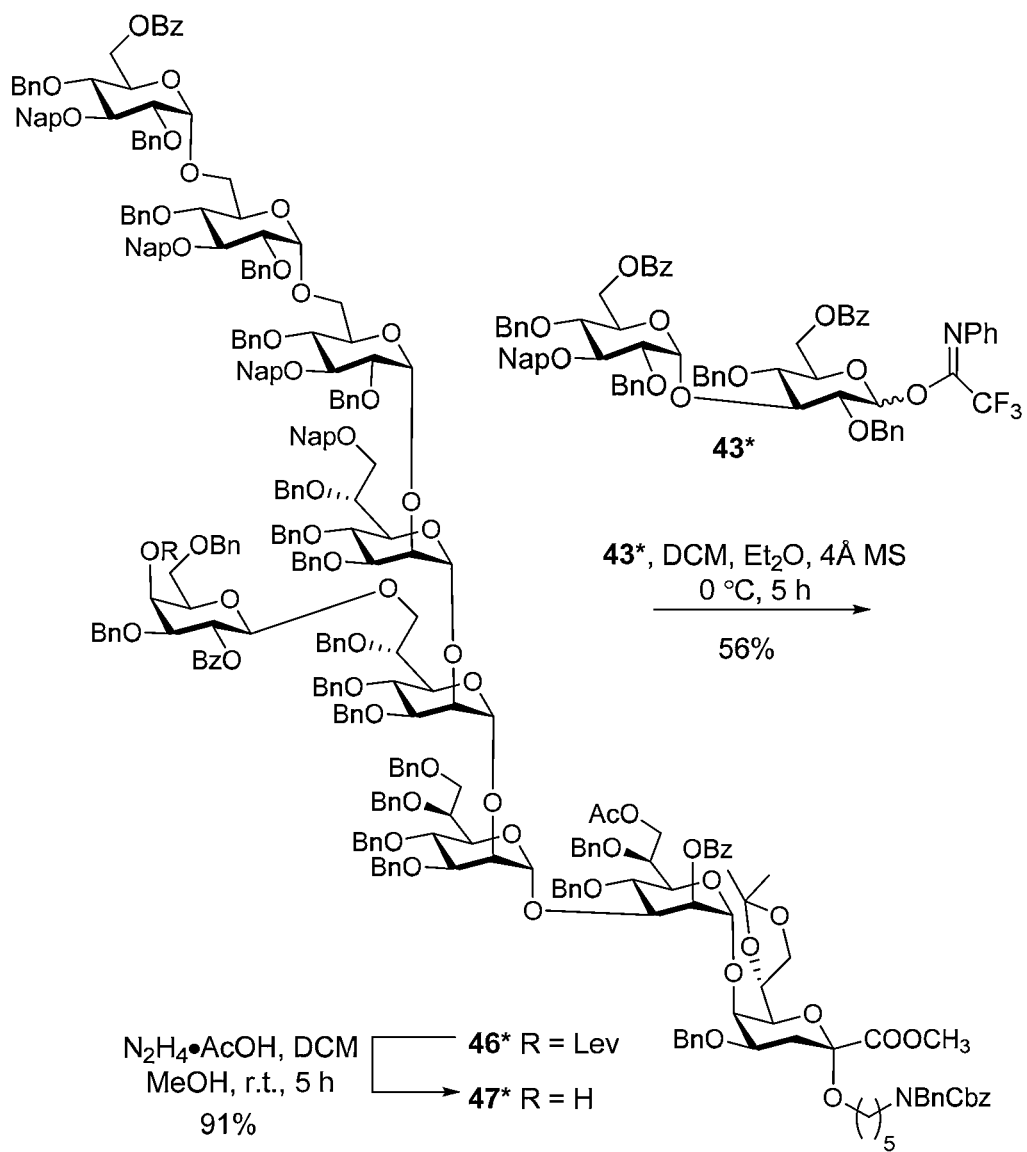
Figure 10D:
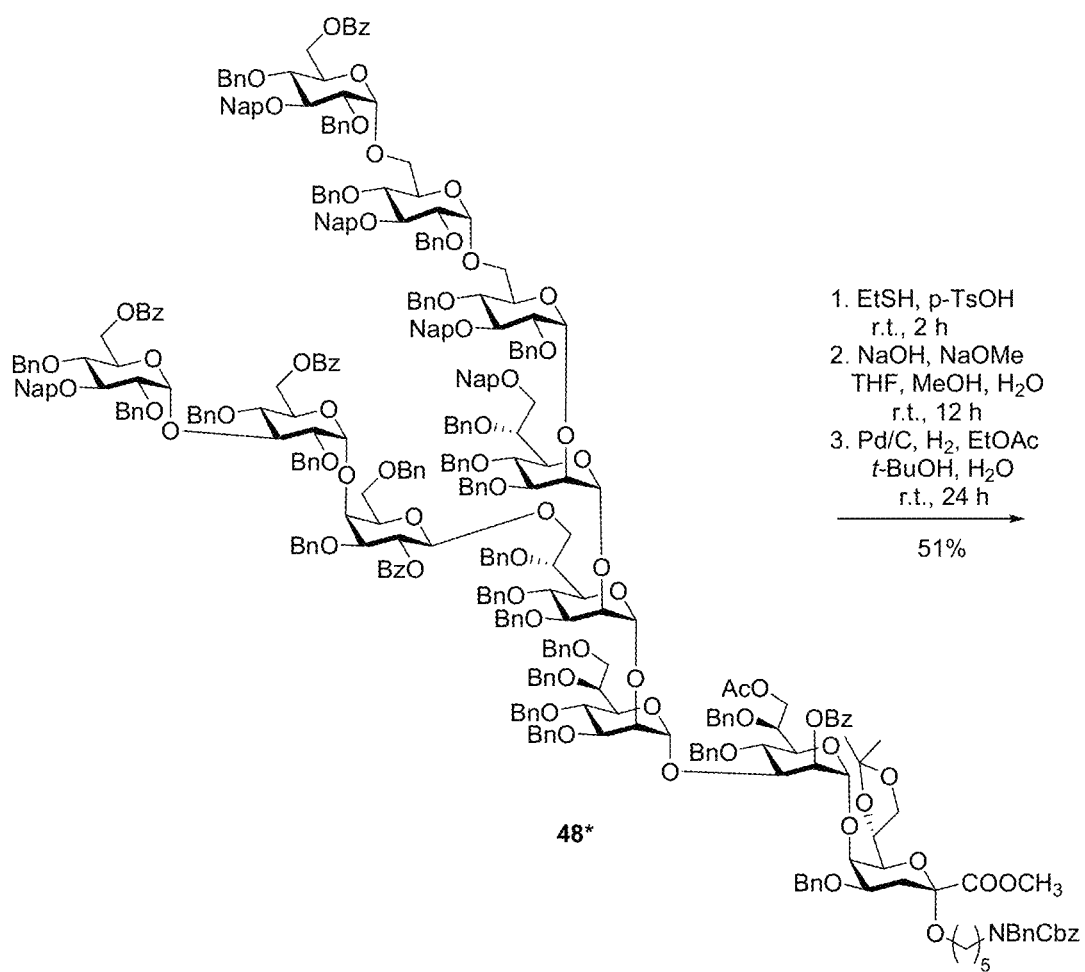
Figure 10E:
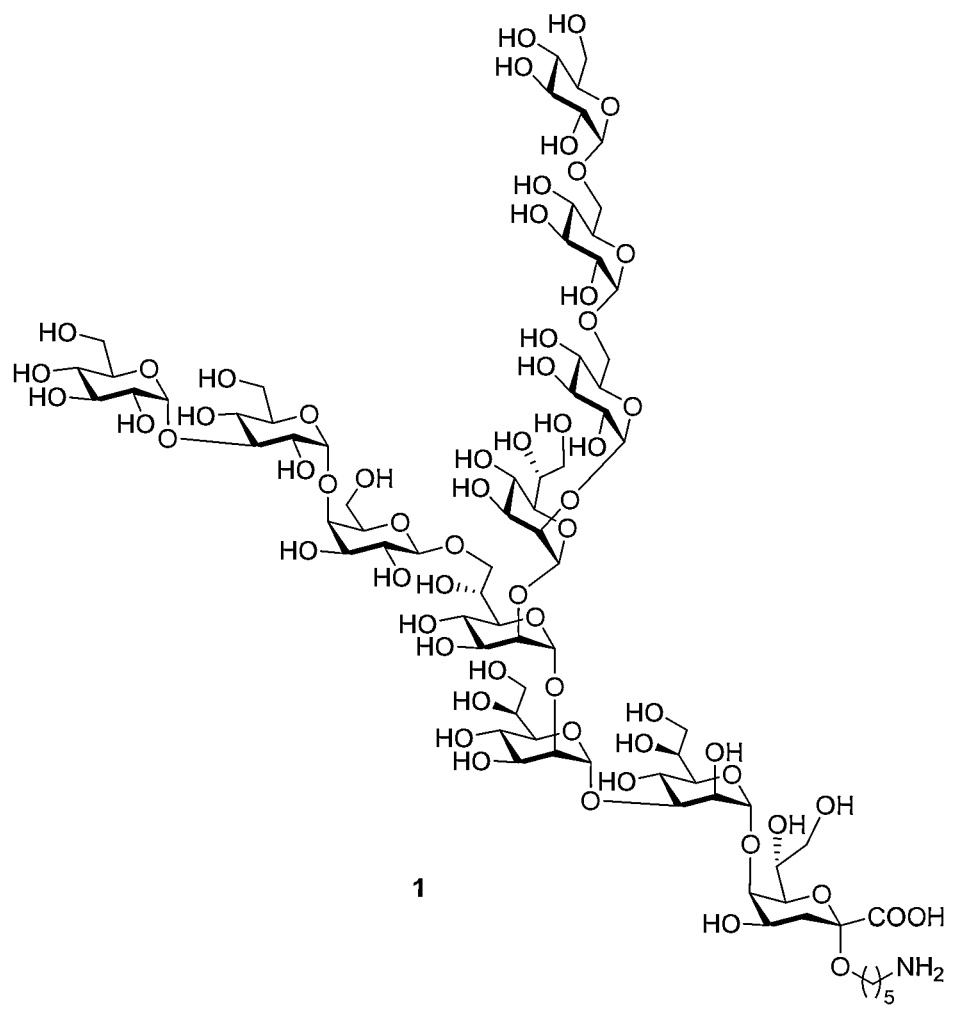

Disaccharide was synthesized as shown in FIG. 9:

Starting from a glucose intermediate 26*, O3 2-naphthylidene was removed under a DDQ condition to prepare a glucose receptor 41*, with a yield of 90%. A glucose donor 7* and the receptor 41* underwent a glycosylation reaction under a synergistic glycosylation condition to prepare singular α-configuration disaccharide 42* (new glycosidic bond: $^3J_{H1/H2}$=3.61 Hz, δ=5.65 ppm), with a yield of 51%. The disaccharide 42* was converted into a phenyl trifluoroacetimidate donor 43* through a two-step reaction, with a yield of 81%.

Compound 41*: The compound 26* (210 mg, 0.32 mmol) was dissolved in a mixed solvent of $DCM/H_2O$ (9:1, v/v, 6.4 mL), and DDQ (145 mg, 0.64 mmol) was added at room temperature. After the reaction temperature restored to room temperature, the reaction continued for 6 h. After the reaction was complete, the reaction solution was diluted with DCM and washed with a 10% $Na_2S_2O_3$ solution and a saturated $NaHCO_3$ solution sequentially. The organic phase was dried over $Na_2SO_4$, filtered and concentrated. The crude product was separated and purified by silica gel column chromatography (petroleum ether/ethyl acetate, 8:1) to prepare the compound 41* (164 mg, 0.29 mmol, 90%). $^1$H NMR (400 MHz, $CDCl_3$) δ8.06-7.95 (m, 2H, Ar), 7.60 (td, J=7.3, 1.4 Hz, 1H, Ar), 7.52-7.21 (m, 10H, Ar), 6.93 (d, J=7.9 Hz, 2H, Ar), 5.02 (d, J=11.0 Hz, 1H, $ArCH_2$), 4.84 (d, J=11.1 Hz, 1H, $ArCH_2$), 4.67 (d, J=10.9 Hz, 3H, H-7, $ArCH_2$), 4.59 (d, J=9.7 Hz, 1H, H-1), 4.45 (dd, J=11.9, 5.6 Hz, 1H, H-7'), 3.81 (t, J=8.8 Hz, 1H, H-3), 3.64 (ddd, J=9.9, 5.6, 2.1 Hz, 1H, H-5), 3.50 (t, J=9.3 Hz, 1H, H-4), 3.35 (t, J=9.2 Hz, 1H, H-2), 2.51 (s, 1H, OH), 2.27 (s, 3H, $CH_3$). $^{13}$C NMR (101 MHz, $CDCl_3$) δ166.2, 138.1, 137.9, 137.8, 133.1, 132.8, 130.0, 129.8, 129.6, 129.3, 128.7, 128.6, 128.4, 128.2, 128.1, 128.0, 87.1 (C-1), 80.6, 78.8, 76.8, 75.2, 74.8, 63.8, 21.1; HRMS (ESI) m/z calcd for $C_{34}H_{34}O_6SNa$ [M+Na]$^+$ 593.1968, found 593.1963.

Compound 42*: The glycosyl donor 7* (320 mg, 0.88 mmol) and the glycosyl receptor 41* (455 mg, 0.81 mmol) were dissolved in $DCM/Et_2O$ (1:2, 8.8 mL). Thiophene (1.5 mL, 8.8 mmol) and 4 Å molecular sieves were added and the mixture was stirred for half an hour. The temperature was reduced to 0° C., and TMSOTf (32 μL, 0.18 mmol) was added for conducting a catalytic glycosylation reaction. After the reaction was complete, the crude product was purified by a silica gel column (petroleum ether/ethyl acetate, 8:1) to prepare the compound 42* (1.2 g, 0.41 mmol, 51%). $^1$H NMR (400 MHz, $CDCl_3$) δ8.11-8.03 (m, 2H, Ar), 8.02-7.94 (m, 2H, Ar), 7.84-7.57 (m, 5H, Ar), 7.55-7.38 (m, 11H, Ar), 7.36 (t, J=7.8 Hz, 2H, Ar), 7.32-7.03 (m, 18H, Ar), 6.93 (d, J=8.0 Hz, 2H, Ar), 5.65 (d, J=3.6 Hz, 1H, H-1b), 5.18-5.04 (m, 2H, $ArCH_2$), 5.06-4.87 (m, 3H, $ArCH_2$), 4.81-4.71 (m, 2H, $ArCH_2$), 4.71-4.62 (m, 2H), 4.60 (d, J=9.7 Hz, 1H, H-1a), 4.60-4.57 (m, 1H), 4.52 (d, J=11.4 Hz, 1H, $ArCH_2$), 4.43 (ddd, J=10.3, 4.3, 2.0 Hz, 1H, H-5a), 4.34 (dd, J=12.0, 5.1 Hz, 1H), 4.28 (dd, J=12.2, 2.0 Hz, 1H), 4.19 (t, J=9.4 Hz, 1H), 4.15-4.05 (m, 2H), 2.29 (s, 3H, $CH_3$). $^{13}$C NMR (101 MHz, $CDCl_3$) δ166.1, 166.0, 138.0, 137.9, 137.6, 137.4, 137.4, 135.8, 133.3, 133.1, 133.0, 132.9, 132.9, 130.0, 130.0, 129.8, 129.7, 129.7, 129.3, 128.6, 128.4, 128.4, 128.4, 128.3, 128.3, 128.2, 128.1, 128.1, 127.9, 127.9, 127.8, 127.7, 127.7, 127.1, 126.6, 126.1, 125.9, 97.1 (C-1b), 88.0 (C-1a), 82.4, 79.8, 79.7, 79.0, 78.3, 75.8, 75.4, 75.2, 74.1, 73.7, 69.2, 63.4, 63.2, 21.1.

Compound 43*: The compound 42* (31.0 mg, 0.028 mmol) was dissolved in a mixed solvent of $THF/H_2O$ (1:1, v/v, 1.4 mL), and bromosuccinimide (14.9 mg, 0.084 mmol) was added. The reaction solution was stirred at room temperature for 4 h. After the reaction raw materials completely disappeared, the reaction solution was diluted with DCM. The organic phase was washed with 10% $Na_2S_2O_3$ and $NaHCO_3$ solutions respectively, dried over anhydrous $Na_2SO_4$, filtered and concentrated. The crude product was purified by column chromatography to prepare an acetal product intermediate (25.2 mg). The acetal product intermediate was dissolved in dry DCM (1.4 mL), N-phenyltrifluoroacetyl chloride (20.9 μl, 0.14 mmol) and DBU (12.6 μL, 0.023 mmol) were added at 0° C., and the reaction solution was stirred at room temperature for 5 h. After TLC monitored that the reaction raw materials completely disappeared, the reaction solution was diluted with DCM and washed with a saturated $NaHCO_3$ solution. The organic phase was dried over anhydrous $Na_2SO_4$, filtered and directly concentrated. The crude product was purified by silica gel column chromatography (petroleum ether/ethyl acetate, 6:1) to prepare the compound 43* (26.5 mg, 2.5 mmol, 81%). [α]$^{22}_D$=84.5 (c 1.0, $CHCl_3$); $^1$H NMR (400 MHz, $CDCl_3$) δ8.04-7.90 (m, 4H, Ar), 7.77-7.56 (m, 4H, Ar), 7.56-7.28 (m, 11H, Ar), 7.27-6.92 (m, 21H, Ar), 6.72-6.52 (m, 2H, Ar), 5.49 (dd, J=19.1, 3.6 Hz, 1H, H-1b), 5.11-4.96 (m, 2H), 4.95-4.78 (m, 2H), 4.76-4.66 (m, 2H), 4.66-4.43 (m, 6H), 4.42-4.23 (m, 2H), 4.22-4.03 (m, 3H). $^{13}$C NMR (101 MHz, $CDCl_3$) δ166.4, 166.3, 166.2, 166.2, 143.5, 138.2, 138.1, 137.9, 137.9, 137.6, 137.5, 137.2, 137.1, 136.0, 136.0, 133.5, 133.3, 133.2, 133.1, 130.2, 130.1, 129.9, 129.9, 129.8, 128.9, 128.8, 128.7, 128.6, 128.6, 128.5, 128.5, 128.4, 128.3, 128.3, 128.1, 128.1, 128.0, 128.0, 127.9, 127.9, 127.9, 127.8, 127.5, 127.3, 126.8, 126.7, 126.2, 126.1, 126.1, 126.0, 124.5, 119.6, 119.4, 97.7 (C-1b), 82.5, 82.3, 80.2, 80.1, 79.8, 79.2, 78.3, 78.3, 78.2, 78.2, 77.9, 76.0, 75.5, 75.3, 74.9, 74.3, 74.2, 73.6, 73.4, 71.4, 69.5, 69.3, 63.5, 63.2, 63.0.

Example 9

Undecasaccharide was synthesized as shown in FIG. 10:

A trisaccharide donor 40* and a pentasaccharide receptor 36* underwent a glycosylation reaction using ether and dichloromethane as a mixed solvent under catalysis of TMSOTf to prepare octasaccharide 44* (new glycosidic bond: $^2J_{H1/C1}$=168.6 Hz, $δ_{H1}$=4.96 ppm), with a yield of 61%. The solvent effect of the ether was used to obtain an α-configuration product with high stereoselectivity. Monochloroacetyl (CA) was selectively removed from the octasaccharide under a thiourea condition to prepare an octasaccharide receptor 45*, with a yield of 92%. The galactosyl phenyl trifluoroacetimidate donor 8* and the octasaccharide receptor 45* underwent a glycosylation reaction under the catalysis of TMSOTf. With the participation of the neighboring group of C2 benzoyl, a singular β-configuration nonasaccharide compound 46* (new glycosidic bond: $^2J_{H1/C1}$=161.4 Hz, $δ_{H1}$=4.49 ppm) was generated, with a yield of 63%. The acetylpropionyl was selectively removed from the nonasaccharide 46* under hydrazine acetate to prepare the compound 47*, with a yield of 91%. The nonasaccharide receptor 47* and the disaccharide donor 43* underwent a glycosylation reaction under the catalysis of TMSOTf, and the solvent effect of the ether was used to prepare an α-configuration linked undecasaccharide 48*, with a yield of 56%. Propylidene was selectively removed from the undecasaccharide 48* by an ethanethiol and p-toluenesulfonic acid method, acyl was removed from the sugar moiety using sodium methoxide and sodium hydroxide, and finally an aromatic protecting group was removed from the sugar moiety using palladium on carbon/hydrogen gas, to prepare the compound 1, with a yield of 51%.

Compound 44*: The glycosyl donor 46* (56.5 mg, 0.033 mmol) and the glycosyl receptor 40* (32.0 mg, 0.011 mmol) were co-evaporated with toluene three times, and a mixed solvent of anhydrous $DCM/Et_2O$ (3:1, v/v, 1.1 mL) and 4 Å molecular sieves were added. The mixture was stirred at room temperature for 30 min, and then the temperature of the reaction solution was reduced to 0° C. TMSOTf (0.05 M, 60 μL, 3.0 μmol) was added to the reaction flask, and the reaction solution was slowly heated to 0° C. After TLC monitored that the glycosyl donor completely disappeared, the reaction was terminated by adding pyridine. After the molecular sieves were filtered out from the reaction solution, the reaction solution was washed with $NaHCO_3$, and the organic phase was dried over anhydrous Na$_2$SO$_4$, filtered and concentrated. The crude product was separated and purified by a silica gel chromatography column (petroleum ether/ethyl acetate, 4:1) to prepare the compound 44* (29.9 mg, 6.6 μmol, 61%). [α]$^{22}_D$=−49.6 (c 1.0, CHCl$_3$); $^1$H NMR (600 MHz, CDCl$_3$) δ8.03 (d, J=7.8 Hz, 2H, Ar), 7.95 (d, J=7.7 Hz, 2H, Ar), 7.80-7.63 (m, 12H, Ar), 7.62-7.52 (m, 5H, Ar), 7.50-6.90 (m, 126H), 5.57 (s, 1H, H-1c), 5.53 (s, 1H, H-2b), 5.51 (d, J=3.5 Hz, 1H, H-1h), 5.36 (s, 1H, H-1b), 5.20-5.14 (m, 3H), 5.12 (s, 1H, H-1d), 5.09-4.84 (m, 13H, H-1e, H-1f, H-1g, ArCH$_2$), 4.84-4.73 (m, 5H), 4.72-4.64 (m, 10H), 4.63-4.53 (m, 9H), 4.52-4.46 (m, 8H), 4.45-4.20 (m, 23H), 4.19-4.10 (m, 6H), 4.10-4.00 (m, 7H), 4.00-3.79 (m, 19H), 3.79-3.63 (m, 10H), 3.63-3.43 (m, 9H), 3.40 (dd, J=9.7, 3.5 Hz, 1H), 3.35-3.29 (m, 5H), 3.29-3.15 (m, 5H), 2.07-2.00 (m, 1H, H-2a(e)), 1.93 (s, 3H, Ac), 1.81 (t, J=12.3 Hz, 1H, H-2a(a)), 1.55-1.42 (m, 4H, CH$_2$CH$_2$), 1.26-1.06 (m, 8H, CH$_2$, OCH$_3$, OCH$_3$). $^{13}$C NMR (101 MHz, CDCl$_3$) δ170.4, 168.0, 166.7, 166.1, 165.5, 139.1, 138.9, 138.7, 138.6, 138.4, 138.2, 138.0, 137.8, 137.8, 137.5, 136.4, 136.4, 136.0, 133.3, 133.2, 133.0, 133.0, 132.9, 132.8, 130.1, 129.9, 129.9, 129.6, 128.8, 128.5, 128.5, 128.4, 128.4, 128.4, 128.3, 128.3, 128.3, 128.2, 128.2, 128.2, 128.2, 128.1, 128.1, 128.0, 127.9, 127.8, 127.8, 127.7, 127.7, 127.6, 127.6, 127.5, 127.5, 127.4, 127.4, 127.3, 127.2, 127.2, 127.2, 127.1, 126.9, 126.6, 126.4, 126.3, 126.1, 125.9, 125.9, 125.8, 125.8, 125.6, 125.6, 125.5, 109.8, 101.5 (C-1c, C-1e), 100.3 (C-1d), 98.9, 97.7 (C-1g), 97.2 (C-1f), 96.9 (C-1h), 96.7 (C-1b), 82.0, 81.6, 80.4, 75.8, 75.5, 75.5, 75.1, 75.0, 74.7, 74.3, 74.1, 73.2, 73.0, 72.8, 72.6, 72.4, 72.1, 71.7, 71.1, 70.3, 68.9, 67.8, 67.4, 67.2, 65.9, 65.5, 65.3, 63.5, 52.3, 40.6, 31.6, 29.7, 29.3, 26.8, 24.6, 23.5, 22.7, 21.1; Maldi-TOf m/z calcd for C$_{273}$H$_{278}$O$_{53}$ClNNa [M+Na]$^+$ 4475.8670, found 4475.581.

Compound 45*: The compound 44* (23.0 mg, 0.005 mmol) was dissolved in CHCl$_3$ and MeOH (1:1, v/v, 1.5 mL), and thiourea (N$_2$H$_4$CS) (3.0 mg, 0.04 mmol) was added at room temperature. The reaction solution was stirred at 60° C. for 24 h. After TLC showed that the reaction raw materials completely disappeared, the reaction solution was diluted with DCM and washed with saturated NaHCO$_3$. The aqueous phase was extracted twice with DCM. The organic phase was dried over anhydrous Na$_2$SO$_4$, filtered and concentrated. The crude product was separated and purified by a silica gel chromatography column (petroleum ether/ethyl acetate, 3:1) to prepare the compound 45* (20.1 mg, 4.6 μmol, 92%). [α]$^{22}_D$=105.0 (c 1.0, CHCl$_3$); $^1$H NMR (600 MHz, CDCl$_3$) δ8.07-8.00 (m, 2H, Ar), 7.99-7.94 (m, 2H, Ar), 7.83-7.57 (m, 17H, Ar), 7.52-6.92 (m, 126H, Ar), 5.58-5.48 (m, 3H, H-1c, H-2b, H-1h), 5.38 (d, J=1.7 Hz, 1H, H-1b), 5.25-5.16 (m, 4H, H-1d, H-1e, ArCH$_2$), 5.14-4.95 (m, 10H, H-1f, H-1g), 4.96-4.81 (m, 8H), 4.81-4.57 (m, 19H), 4.57-4.48 (m, 9H), 4.48-4.29 (m, 22H), 4.27-4.12 (m, 9H), 4.10-3.78 (m, 32H), 3.72 (dd, J=19.6, 10.7 Hz, 5H), 3.67-3.46 (m, 14H), 3.46-3.36 (m, 4H), 3.32-3.16 (m, 5H), 2.24 (d, J=11.1 Hz, 1H, H-1a(e)), 2.12-2.03 (m, 1H, H-1a (a)), 1.96 (s, 3H, Ac), 1.54 (s, 4H), 1.38-1.09 (m, 8H, CH$_2$, OCH$_3$, OCH$_3$). $^{13}$C NMR (151 MHz, CDCl$_3$) δ170.4, 168.3, 166.1, 165.5, 156.7, 156.2, 139.1, 139.0, 138.8, 138.7, 138.7, 138.6, 138.6, 138.5, 138.4, 138.4, 138.2, 138.1, 138.0, 138.0, 138.0, 137.7, 136.8, 136.4, 136.3, 136.0, 135.9, 133.3, 133.2, 133.0, 132.9, 132.9, 132.8, 130.1, 129.9, 129.9, 129.6, 128.8, 128.8, 128.5, 128.5, 128.4, 128.4, 128.3, 128.3, 128.3, 128.2, 128.2, 128.1, 128.1, 128.0, 127.7, 127.8, 127.8, 127.8, 127.7, 127.6, 127.6, 127.5, 127.4, 127.3, 127.3, 127.2, 127.2, 127.2, 126.9, 126.6, 126.5, 126.4, 126.3, 126.3, 126.1, 126.0, 125.9, 125.9, 125.9, 125.9, 125.8, 125.8, 125.7, 125.7, 125.6, 125.5, 125.3, 109.7, 101.3 (C-1c, C-1e), 100.8 (C-1d), 99.1, 97.7 (C-1g), 97.2 (HC-1f), 96.7 (C-1h), 96.5 (C-1b), 82.0, 81.7, 81.6, 81.1, 80.5, 80.3, 80.2, 79.8, 78.7, 78.2, 75.8, 75.8, 75.5, 75.4, 75.2, 75.1, 75.0, 74.9, 74.7, 74.5, 74.2, 73.8, 73.2, 72.8, 72.8, 72.5, 72.3, 72.2, 72.0, 71.8, 71.7, 71.6, 71.4, 71.0, 70.8, 70.2, 68.9, 67.9, 67.4, 67.2, 65.6, 65.3, 63.5, 63.4, 62.6, 52.4, 50.5, 50.2, 47.1, 46.2, 31.6, 29.7, 29.3, 28.0, 27.6, 26.8, 24.6, 23.5, 22.7, 21.1, 14; Maldi-TOf m/z calcd for C$_{271}$H$_{277}$O$_{53}$NNa [M+Na]$^+$ 4399.8954, found 4399.843.

Compound 46*: The galactose donor 8* (6.2 mg, 8.4 μmol) and the octasaccharide receptor 45* (18.4 mg, 4.2 μmol) were co-evaporated three times with toluene, and dry DCM (0.8 mL) and activated 4 Å molecular sieves were added. The reaction solution was stirred at room temperature for 30 min and cooled to 0° C. TMSOTf (25.0 L, 0.05 M in DCM, 1.3 μmol) was added. The reaction solution was further stirred at 0° C. for 3 h, and the reaction was terminated with pyridine. The reaction solution was filtered, diluted with DCM and washed with saturated NaHCO$_3$. The organic phase was dried over anhydrous Na$_2$SO$_4$ and concentrated under reduced pressure. The crude product was purified and separated by silica gel column chromatography (petroleum ether/ethyl acetate, 5:1) to prepare the compound 46* (14.6 mg, 2.9 μmol, 71%). [α]$^{22}_D$=32.1 (c 0.5, CHCl$_3$); $^1$H NMR (600 MHz, CDCl$_3$) δ8.07-7.91 (m, 4H, Ar), 7.80-7.64 (m, 13H, Ar), 7.60-6.69 (m, 141H, Ar), 5.58 (d, J=3.3 Hz, 1H, H-4i), 5.55-5.53 (m, 1H, H-2b), 5.46 (d, J=3.4 Hz, 1H, H-1h), 5.41-5.30 (m, 3H, H-2i, H-1b, H-1c), 5.17 (d, J=15.1 Hz, 1H, H-1d, ArCH$_2$), 5.12-5.04 (m, 2H, ArCH$_2$), 5.02-4.73 (m, 12H, H-1e, H-1f, H-1g), 4.73-4.44 (m, 24H, H-1i), 4.42-4.18 (m, 24H), 4.17-3.80 (m, 30H), 3.79-3.49 (m, 18H), 3.49-3.11 (m, 15H), 2.55-2.39 (m, 5H, CH$_2$CH$_2$), 2.13-1.98 (m, 4H), 1.94 (s, 3H, Ac), 1.69-1.50 (m, 4H, CH$_2$CH$_2$), 1.26 (d, J=5.7 Hz, 8H, 8H, CH$_2$, OCH$_3$, OCH$_3$). $^{13}$C NMR (151 MHz, CDCl$_3$) δ206.3, 172.0, 170.4, 168.2, 166.1, 165.6, 165.2, 156.7, 156.2, 139.1, 138.9, 138.7, 138.7, 138.6, 138.5, 138.4, 138.3, 138.2, 138.1, 138.0, 137.7, 137.4, 137.3, 136.3, 136.3, 136.0, 135.9, 133.3, 133.1, 133.0, 132.9, 132.9, 132.7, 132.7, 130.0, 129.9, 129.9, 129.8, 129.6, 128.5, 128.5, 128.4, 128.3, 128.3, 128.2, 128.2, 128.1, 128.1, 128.0, 128.0, 127.9, 127.9, 127.8, 127.8, 127.7, 127.6, 127.6, 127.5, 127.5, 127.4, 127.4, 127.3, 127.3, 127.3, 127.2, 127.2, 127.1, 127.1, 126.9, 126.9, 126.8, 126.8, 126.7, 126.4, 126.3, 126.3, 126.1, 126.0, 125.9, 125.9, 125.8, 125.7, 125.5, 125.4, 109.8, 101.7 (C-1c, C-1d, C-1i), 101.1 (C-1e), 99.0, 97.6 (C-1g), 97.2 (C-1f), 96.6 (C-1b), 96.4 (C-1h), 81.9, 81.7, 81.6, 81.1, 80.3, 80.1, 79.1, 76.4, 75.8, 75.5, 75.2, 75.2, 75.1, 75.0, 75.0, 74.9, 74.7, 74.6, 74.3, 74.1, 73.6, 73.2, 73.1, 72.8, 72.6, 72.5, 72.3, 72.0, 72.0, 71.8, 71.6, 71.5, 71.5, 71.1, 71.0, 70.6, 70.3, 68.9, 67.8, 67.4, 67.2, 66.9, 65.9, 65.6, 65.4, 63.5, 63.4, 52.4, 50.5, 50.2, 47.1, 46.2, 38.0, 31.7, 29.7, 29.4, 29.3, 28.0, 27.9, 27.6, 26.8, 26.7, 24.6, 23.5; Maldi-TOf m/z calcd for C$_{303}$H$_{309}$O$_{60}$NNa [M+Na]$^+$ 4944.1051, found 4944.566.

Compound 47*: The compound 46* (12.5 mg, 2.5 μmol) was dissolved in a DCM/MeOH (10:1, v/v, 0.8 mL) mixed solvent, and hydrazine acetate (3.0 mg, 7.5 μmol) was added at room temperature. The reaction solution was stirred at room temperature for 5 h. After TLC showed that the reaction raw materials completely disappeared, the reaction solution was diluted with DCM, and the organic phase was washed with NaHCO$_3$, dried over anhydrous Na$_2$SO$_4$, filtered and concentrated. The crude product was separated and purified by silica gel column chromatography (petroleum ether/ethyl acetate, 5:1) to prepare the compound 47* (11.0 mg, 2.3 µmol, 91%). $[\alpha]^{22}_D$=45.3 (c 0.5, CHCl$_3$); $^1$H NMR (600 MHz, CDCl$_3$) δ8.07-7.92 (m, 2H, Ar), 7.87-7.67 (m, 13H, Ar), 7.63-6.77 (m, 141H, Ar), 5.55 (s, 1H, H-2b), 5.52-5.46 (m, 2H, H-2i, H-1h), 5.42 (s, 1H, H-1b), 5.37 (s, 1H, H-1c), 5.24-5.16 (m, 3H, H-1d, ArCH$_2$), 5.11 (d, J=10.9 Hz, 1H, ArCH$_2$), 5.07-4.88 (m, 11H, H-1e, H-1f, H-1g), 4.85-4.79 (m, 3H), 4.75-4.55 (m, 21H), 4.55-4.49 (m, 6H), 4.48-4.21 (m, 29H, H-1h), 4.19-4.03 (m, 14H), 4.02-3.71 (m, 30H), 3.70-3.48 (m, 13H), 3.47-3.12 (m, 12H), 2.43-2.26 (m, 1H, H-2a(e)), 2.03 (d, J=11.9 Hz, 1H, H-2a(a)), 1.96 (s, 1H, Ac), 1.34-1.17 (m, 8H, CH$_2$, OCH$_3$, OCH$_3$). $^{13}$C NMR (151 MHz, CDCl$_3$) δ170.6, 168.4, 166.3, 165.7, 165.3, 156.3, 139.3, 139.1, 138.8, 138.8, 138.7, 138.5, 138.5, 138.4, 138.3, 138.2, 138.1, 138.1, 137.6, 137.3, 137.0, 136.5, 136.4, 136.1, 136.1, 133.4, 133.3, 133.1, 133.1, 133.0, 132.9, 132.8, 130.2, 130.1, 130.0, 129.8, 129.8, 129.7, 128.7, 128.6, 128.5, 128.5, 128.4, 128.4, 128.3, 128.2, 128.2, 128.1, 128.1, 128.0, 128.0, 127.9, 127.9, 127.7, 127.7, 127.6, 127.6, 127.6, 127.5, 127.5, 127.4, 127.3, 127.2, 127.2, 127.0, 126.9, 126.9, 126.8, 126.7, 126.6, 126.4, 126.4, 126.2, 126.1, 126.0, 125.9, 125.8, 125.7, 125.6, 109.9, 101.8 (C-1c, C-1d, C-1i), 101.2 (C-1e), 99.2, 97.8 (C-1g), 97.4 (C-1f), 96.7 (C-1b, C-1h), 82.0, 81.8, 81.8, 81.3, 80.4, 80.3, 78.5, 77.6, 75.9, 75.6, 75.4, 75.3, 75.2, 75.1, 74.9, 74.7, 74.3, 73.7, 73.4, 73.2, 72.9, 72.7, 72.7, 72.6, 72.3, 72.1, 71.9, 71.7, 71.7, 71.2, 71.1, 70.9, 70.7, 70.4, 69.0, 68.0, 67.9, 67.6, 67.3, 65.9, 65.5, 65.3, 63.6, 63.5, 52.6, 50.7, 50.3, 47.3, 46.3, 32.1, 31.8, 29.9, 29.5, 28.2, 27.7, 27.0, 24.7, 23.6, 22.8, 21.2, 14.3; Maldi-TOf m/z calcd for C$_{298}$H$_{303}$O$_{58}$NNa [M+Na]$^+$ 4846.0683, found 4846.260.

Compound 48*: The glycosyl donor 43* (31.8 mg, 26 µmol) and the nonasaccharide receptor 47* (21.0 mg, 4.4 µmol) were co-evaporated three times with toluene, and dry DCM/Et$_2$O (1:3, v/v, 1.2 mL) and activated 4 Å molecular sieves were added. The reaction solution was stirred at room temperature for 30 min and cooled to 0° C. TMSOTf (78 µL, 0.05 M in DCM, 3.9 µmol) was added. The reaction solution was further stirred at 0° C. for 5 h, and the reaction was terminated with pyridine. The reaction solution was filtered, diluted with DCM and washed with saturated NaHCO$_3$. The organic phase was dried over anhydrous Na$_2$SO$_4$ and concentrated under reduced pressure. The crude product was purified and separated by silica gel column chromatography (petroleum ether/ethyl acetate, 4:1) to prepare the compound 48* (14.4 mg, 2.4 µmol, 56%). $^1$H NMR (600 MHz, CDCl$_3$) δ8.08-7.94 (m, 10H, Ar), 7.88-7.63 (m, 18H, Ar), 7.59-7.35 (m, 40H, Ar), 7.30-6.78 (m, 127H, Ar), 5.68-5.60 (m, 2H, H-1h, H-2b), 5.59-5.50 (m, 2H, H-2i, H-1d), 5.49 (d, J=3.4 Hz, 1H, H-1k), 5.41-5.26 (m, 3H, H-1b, H-1c, H-1j), 5.20 (d, J=20.6 Hz, 3H, ArCH$_2$), 5.14-4.86 (m, 22H, H-1e, H-1f, H-1g), 4.83-4.48 (m, 31H), 4.48-4.36 (m, 26H), 4.24-4.05 (m, 12H), 4.03-3.68 (m, 33H), 3.67-3.09 (m, 21H), 2.28-2.22 (m, 1H, H-2a(e)), 1.92 (t, J=5.9 Hz, 4H, Ac, H-2a(a)), 1.63-1.46 (m, 8H), 1.36-1.14 (m, 9H). $^{13}$C NMR (151 MHz, CDCl$_3$) δ170.5, 168.2, 166.3, 166.1, 165.6, 165.0, 156.8, 156.3, 139.1, 138.8, 138.8, 138.7, 138.6, 138.5, 138.3, 138.1, 137.9, 137.4, 136.5, 136.4, 136.2, 136.1, 136.0, 133.4, 133.3, 133.1, 133.1, 133.0, 133.0, 132.9, 132.9, 132.6, 131.1, 130.4, 130.3, 130.2, 130.0, 129.9, 129.8, 129.7, 128.9, 128.7, 128.6, 128.5, 128.4, 128.3, 128.3, 128.2, 128.2, 128.2, 128.1, 128.0, 128.0, 127.9, 127.9, 127.8, 127.8, 127.7, 127.7, 127.6, 127.5, 127.5, 127.4, 127.3, 127.3, 127.3, 127.2, 127.2, 127.0, 126.9, 126.8, 126.8, 126.7, 126.5, 126.4, 126.4, 126.2, 126.2, 126.1, 126.0, 125.9, 125.8, 125.7, 125.6, 125.2, 109.9, 102.2 (C-1i), 101.6 (C-1c, C-1d, C-1e), 99.0, 98.2 (C-1f), 97.8 (C-1g), 97.4 (C-1j), 97.2 (C-1h), 96 (C-1k).7, 96.5 (C-1b), 82.2, 82.0, 81.8, 81.7, 81.1, 80.6, 80.4, 80.2, 80.0, 78.1, 77.9, 77.6, 75.9, 75.8, 75.6, 75.3, 75.2, 75.2, 75.1, 74.8, 74.1, 73.6, 73.2, 72.9, 72.6, 72.5, 72.3, 72.1, 72.0, 71.9, 71.8, 71.7, 71.3, 71.1, 70.9, 70.6, 70.3, 69.2, 69.1, 68.4, 68.0, 67.5, 67.3, 65.8, 65.5, 63.5, 52.5, 50.7, 50.3, 47.2, 46.3, 43.0, 42.4, 41.0, 38.9, 36.8, 36.1, 32.3, 32.1, 31.7, 29.9, 29.9, 29.8, 29.8, 29.7, 29.6, 29.5, 29.5, 29.4, 29.1, 28.6, 28.2, 27.7, 27.4, 27.0, 24.7, 24.0, 23.6, 22.8, 21.2, 20.9, 20.7, 17.6, 17.4, 16.1, 14.8, 14.3, 11.1, 8.1; Maldi-TOf m/z calcd for C$_{363}$H$_{363}$O$_{70}$NNa [M+Na]$^+$ 5878.4768, found 5878.833.

Compound 1: The compound 48* (10.0 mg, 2.6 µmol) was dissolved in DCM (1.2 mL), and ethanethiol (1.5 mL, 0.14 mmol) and p-toluene sulfonic acid monohydrate (5.0 mg) were added at room temperature. The reaction solution was stirred at room temperature for 2 h. After TLC showed that the raw materials completely reacted, the reaction solution was diluted with DCM and washed with NaHCO$_3$, and the organic phase was dried over anhydrous Na$_2$SO$_4$ and filtered. The crude product was purified and separated by silica gel column chromatography (petroleum ether/ethyl acetate, 2:1) to prepare a compound intermediate (8.9 mg). The intermediate was dissolved in THF/MeOH (1.0 mL), and a 15% NaOH (10.0 µL) aqueous solution was added at room temperature. After the reaction solution was stirred for 1 h, sodium methoxide (10 mg, 0.18 mmol) was added. The reaction solution was further stirred at room temperature for 12 h. After the reaction raw materials completely disappeared, IR120 (H$^+$) resin was added for neutralization to a pH of 7. After filtration and concentration, the crude product was purified and separated by rapid silica gel column chromatography to prepare a semi-deprotected product. The semi-deprotected product was dissolved in THF/t-Butanol/H$_2$O (1:2:1, v/v/v, 1.5 mL), and 20% Pd/C (20 mg) was added. The mixture reacted at 4 atmospheres of H$_2$ gas for 24 h, and the reaction solution was filtered and concentrated. The crude product was purified by HPLC, and only a small amount of deprotected undecasaccharide 1 (2.73 mg, 51%) was prepared. Maldi-TOf m/z calcd for C$_{77}$H$_{132}$O$_{62}$N [M−H]$^−$ 2062.7207, found 2062.713.

Figure 11:
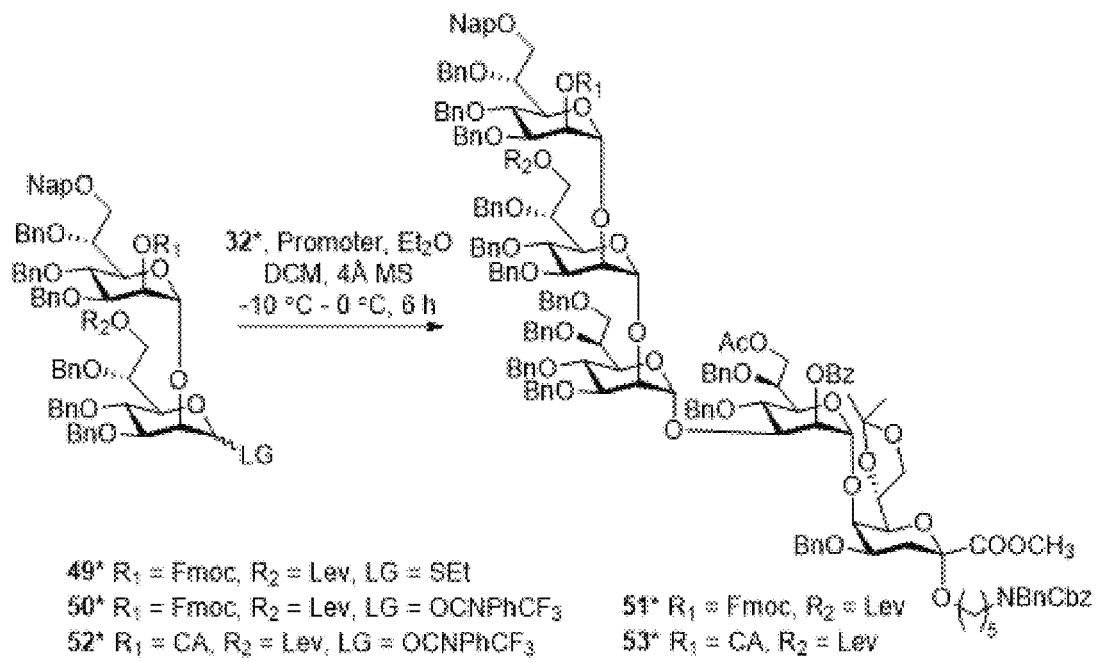
FIG. 11 shows a route for synthesizing pentasaccharide through a [2+3] assembly strategy in Comparative Example 1.

Comparative Example 1 Synthesis of Pentasaccharide Using a [2+3] Assembly Strategy This is as shown in FIG. 11.

Using [2+3] to synthesize pentasaccharide, a disaccharide donor 49* (1.2 equivalents) with a terminal ethylthio and a receptor 32* (1.0 equivalent) underwent a glycosylation reaction under co-catalysis of NIS-TMSOTf or NIS-AgOTf, but the target pentasaccharide 51* was not prepared.

A more active trifluoroimidate donor 50* (1.2 equivalents) and the same receptor 32* (1.0 equivalent) underwent a reaction under catalysis of TMSOTf, and only a trace amount of pentasaccharide was prepared.

A trifluoroimidate disaccharide donor 52* (1.2 equivalents) protected by C2' CA and C7 Lev underwent a coupling reaction with the receptor 32* (1.0 equivalent) under a TMSOTf condition, and only a trace amount of pentasaccharide was detected by mass spectrometry.

The above reaction results are shown in Table 1.

TABLE 1

| No. | Donor | Receptor | Catalyst | Result |
| --- | --- | --- | --- | --- |
| 1 | 49* | 32* | NIS-TMSOTf | NP[a] |
| 2 | 49* | 32* | NIS-AgOTf | NP[a] |
| 3 | 50* | 32* | TMSOTf | Trace [b] |
| 4 | 52* | 32* | TMSOTf | Trace [b] |

NP[a]: No compounds were detected.
Trace [b]: A small amount of product was detected by mass spectrometry.

From the above reactions, we can see that the [2+3] assembly strategy is unable to effectively prepare a pentasaccharide target.

Figure 12:
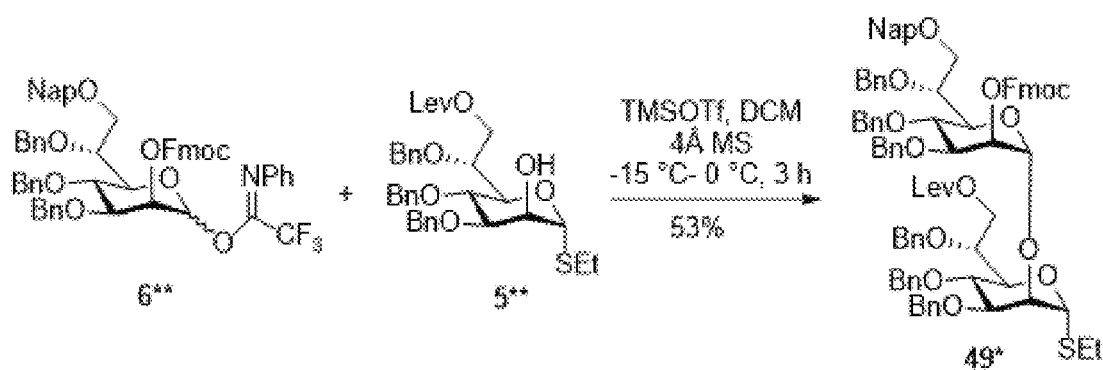
FIG. 12 shows the synthesis route of disaccharide 43* in Comparative Example 1.

The disaccharide donor 49* was prepared by the following method (as shown in FIG. 12):

A glycosyl donor 6 and a receptor 5 underwent a glycosylation reaction under the catalysis of TMSOTf to prepare singular α-configuration disaccharide 49*, with a yield of 53%.

Figure 13:
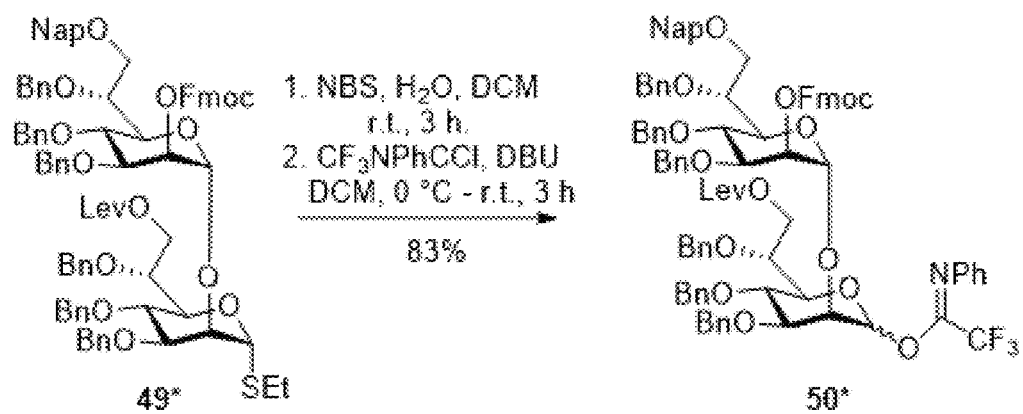
FIG. 13 shows the synthesis route of disaccharide 50* in Comparative Example 1.
Figure 14:
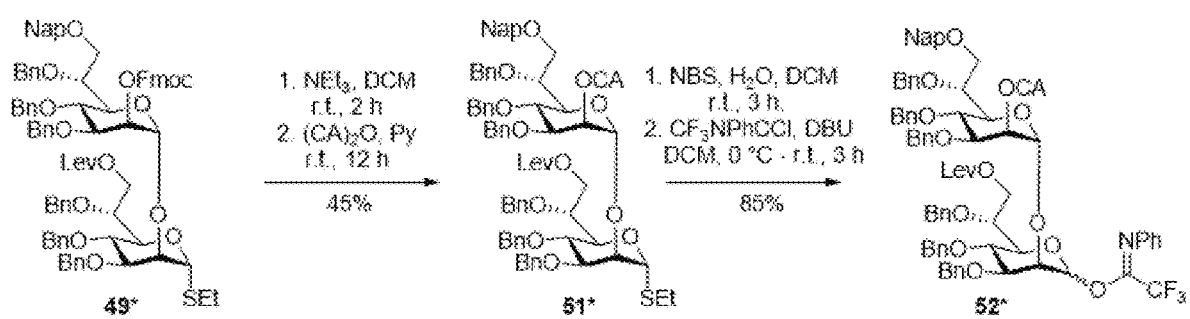
FIG. 14 shows the synthesis route of disaccharide 52* in Comparative Example 1.

The trifluoroimidate donor 50* was prepared by the following method (FIG. 13):

Terminal ethylthio was removed from the thioglucoside 49* in an NBS condition, and the exposed terminal hydroxyl reacted with chloroacetylphenyl trifluoroimidate under the catalysis of DBU to prepare a disaccharide donor 50*, with a two-step yield of 83%.

The trifluoroimidate disaccharide donor 52* was prepared by the following method:

A Fmoc group was removed from the thioglucoside 49* under a triethylamine condition, and then the 2″-hydroxyl was protected with chloroacetyl under chloroacetic anhydride and pyridine to prepare the compound 51* in two steps with a yield of 45%. Terminal ethylthio was removed from the thioglucoside 51* in an NBS condition, and the exposed terminal hydroxyl reacted with chloroacetylphenyl trifluoroimidate under the catalysis of DBU to prepare the disaccharide donor 52*, with a two-step yield of 85%.

Figure 15A:
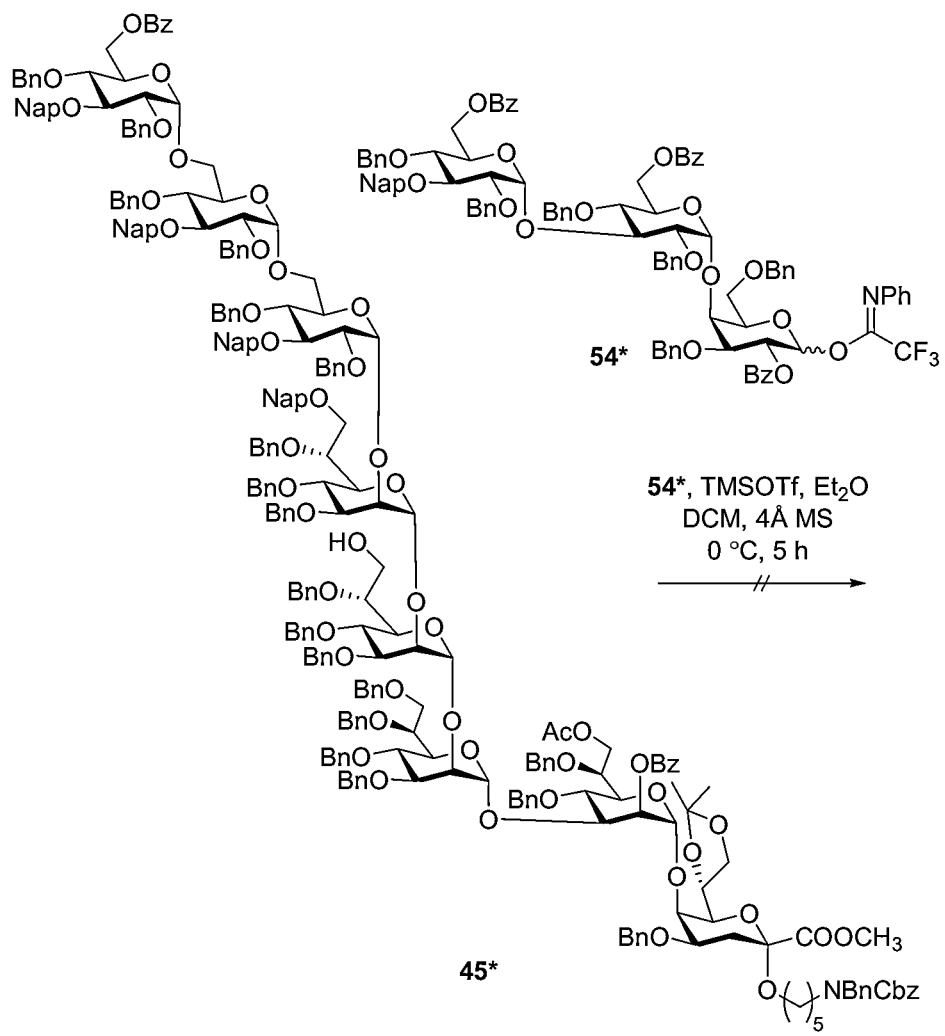
FIG. 15A-B shows a route for synthesizing undecasaccharide through a [8+3] assembly strategy in Comparative Example 2.
Figure 15B:
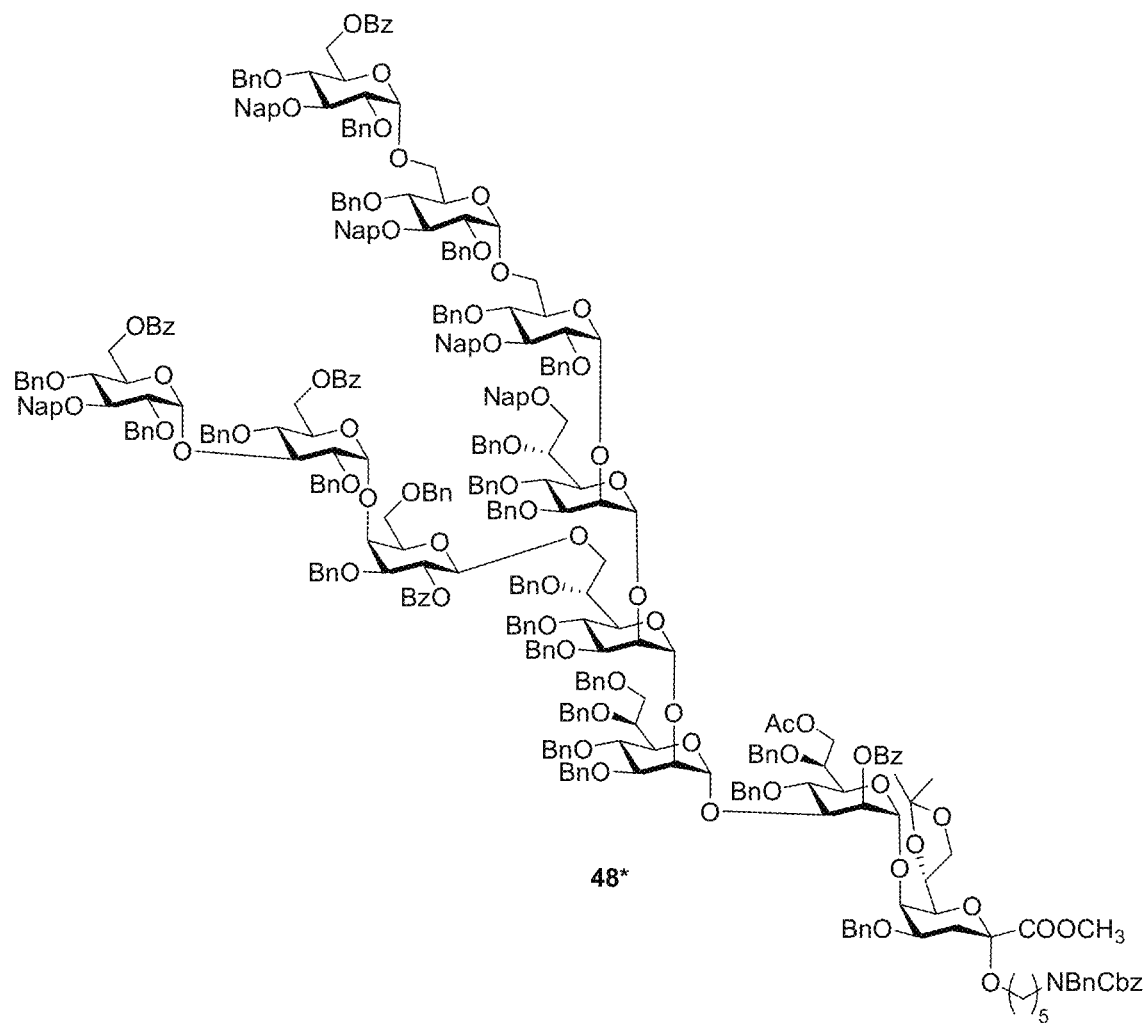

Comparative Example 2 Synthesis of Undecasaccharide Using a [3+8] Assembly STRATEGY This is as shown in FIG. 15.

Pentasaccharide was synthesized using [3+8], and a trisaccharide donor 54* and an octasaccharide receptor 45* underwent a glycosylation reaction under the catalysis of TMSOTf. After 7 h of reaction, the target product could not be detected by thin layer chromatography or mass spectrometry.

It can be seen that the [3+8] assembly strategy cannot effectively undergo a glycosylation reaction to prepare undecasaccharide. The disclosure synthesizes the undecasaccharide 48* using a [2+(1+8)] strategy.

Figure 16:
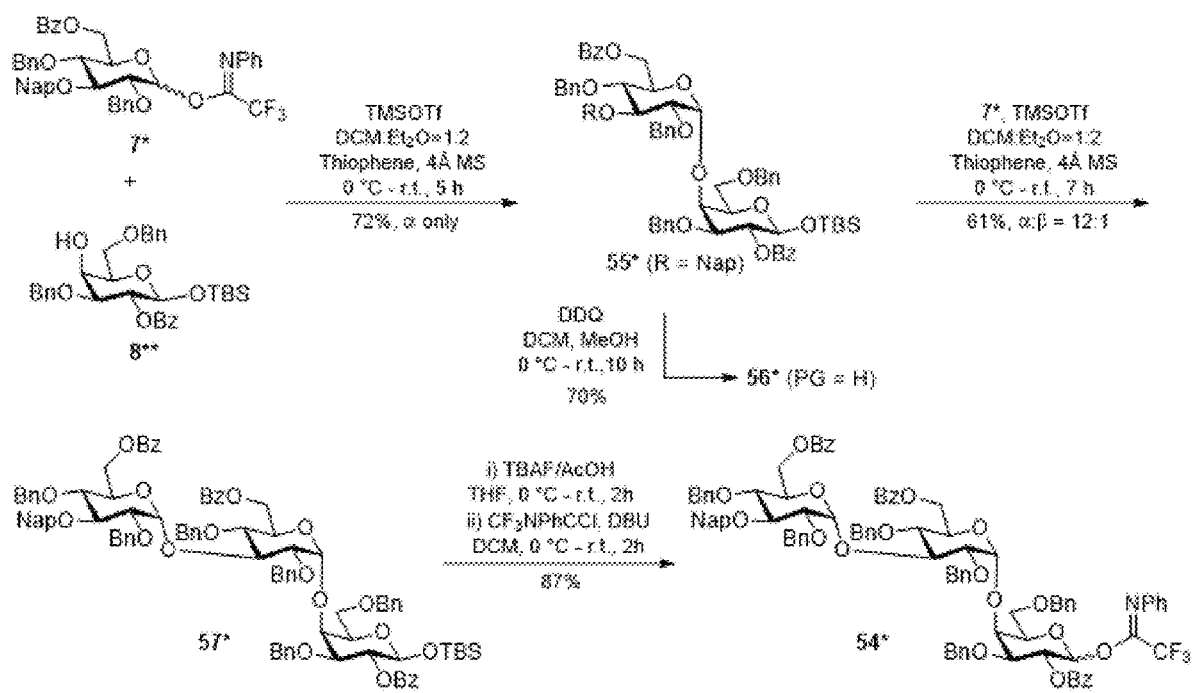
FIG. 16 shows the synthesis route of trisaccharide 54* in Comparative Example 1.

The trisaccharide donor 54* was prepared by the following method (FIG. 16):

A glycosyl donor 7* and a glycosyl receptor 8** underwent a glycosylation reaction under the catalysis of TMSOTf using Et$_2$O and DCM as cosolvents to prepare singular α-configuration disaccharide 55*. A Nap protecting group was removed from the 55 using DDQ to prepare a disaccharide receptor 56*. The disaccharide receptor 56* and a donor 7* further underwent a glycosylation reaction under the catalysis of TMSOTf to prepare trisaccharide 57*, with a yield of 61%. A terminal TBS protecting group was removed under tetrabutylammonium fluoride, and the exposed hydroxyl reacted with chloroacetylphenyl trifluoroimidate to prepare the trisaccharide donor 54*, with a two-step yield of 87%.

What is claimed is:

1. A method for chemically synthesizing a *Helicobacter pylori* lipopolysaccharide core oligosaccharide antigen, wherein an *H. pylori* undecasaccharide antigen shown in formula 1 is synthesized through nine monosaccharide block compounds shown in formula 2 to formula 9 and formula 24;

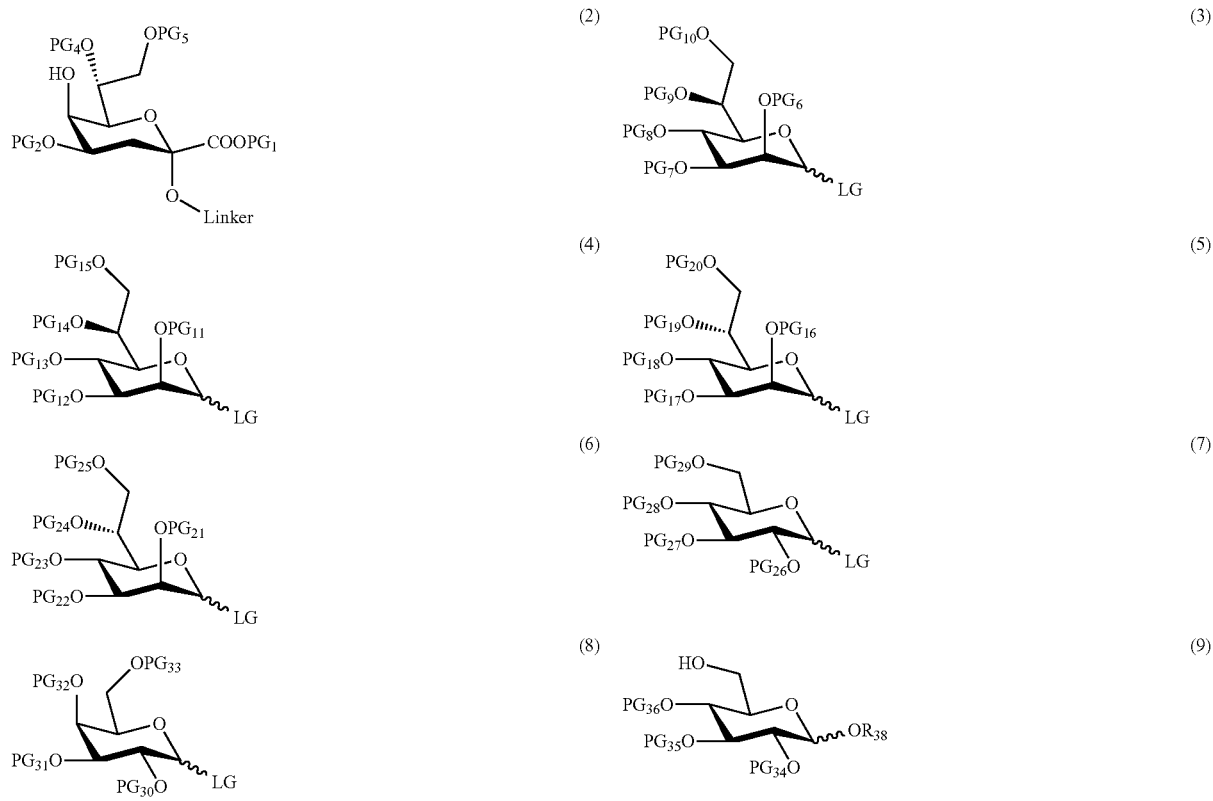

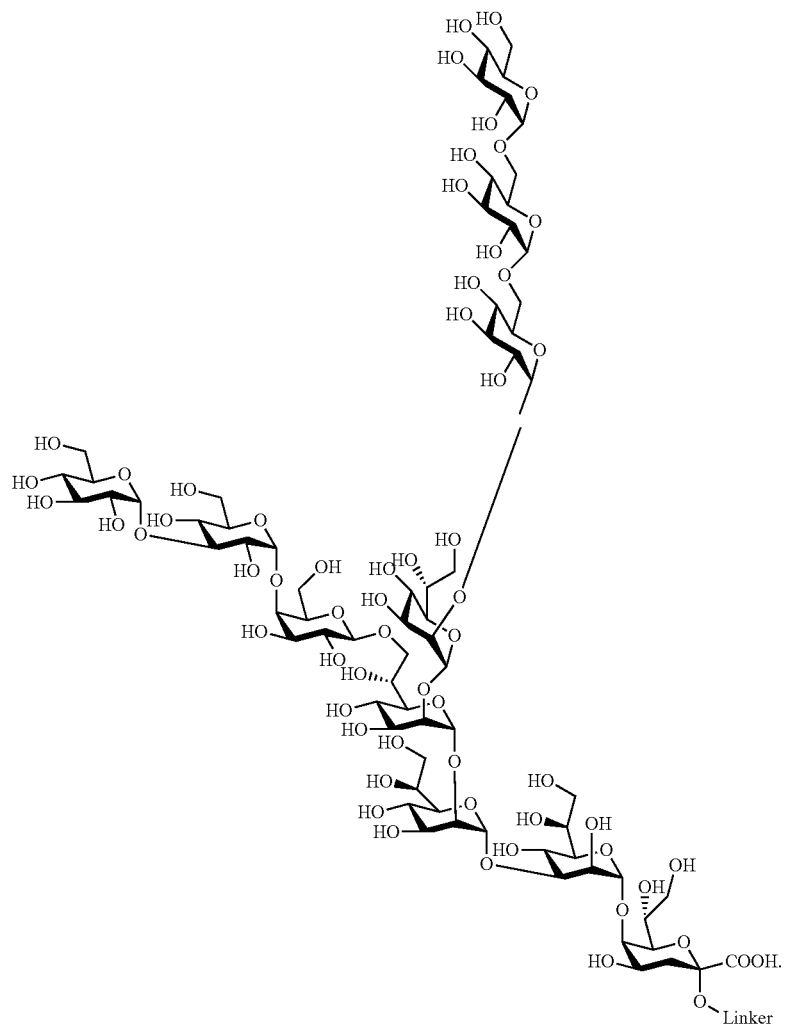
(1)
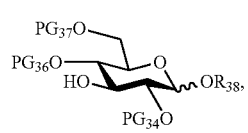
(24)

wherein $PG_2$, $PG_6$, $PG_8$, $PG_9$, $PG_{12}$, $PG_{13}$, $PG_{14}$, $PG_{15}$, $PG_{17}$, $PG_{18}$, $PG_{19}$, $PG_{22}$, $PG_{23}$, $PG_{25}$, $PG_{26}$, $PG_{28}$, $PG_{29}$, $PG_{30}$, $PG_{34}$, $PG_{35}$, $PG_{36}$, and $PG_{37}$ are independently hydrogen, benzyl, 2-naphthylmethyl tert-butyldimethylsilyl, tert-butyldiphenylsilyl or triethylsilyl;

$PG_1$ is any of hydrogen, methyl, ethyl, tert-butyl, or benzyl;

$PG_4$ and $PG_5$ form propylidene;

$PG_7$, $PG_{11}$, $PG_{16}$, $PG_{21}$, $PG_{27}$, $PG_{32}$, $PG_{33}$, and $R_{38}$ are selected from the group consisting of acetyl, chloroacetyl, benzoyl, pivaloyl, acetylpropionyl, 9-pentamethoxycarbonyl, 2-naphthylmethyl, and 2-p-methoxybenzyl;

$PG_{10}$ is one of acetyl, chloroacetyl, benzoyl, pivaloyl, acetylpropionyl, or 9-pentamethoxycarbonyl;

$PG_{20}$ is monochloroacetyl; $PG_{24}$ is benzyl; $PG_{31}$ is benzyl;

a Linker is $-(CH_2)_n-N-Y_1Y_2$ or $-(CH_2)_n-S-Y_1$, wherein n=1-10, and $Y_1$ and $Y_2$ are independently hydrogen, benzyl, 2-naphthylmethyl, or benzylmethoxycarbonyl; and LG is a leaving group, and is selected from any of halogen, trichloroacetimidate, N-phenyltrifluoroacetimidate glycoside, methylthio, ethylthio, phenylthio, p-tolylthio, and dibenzyl phosphate;

the method comprising the following steps:

(a) performing a glycosylation reaction between a saccharide block donor formula 3 and a saccharide block receptor formula 2 to prepare a disaccharide compound 11 by the following synthesis route:

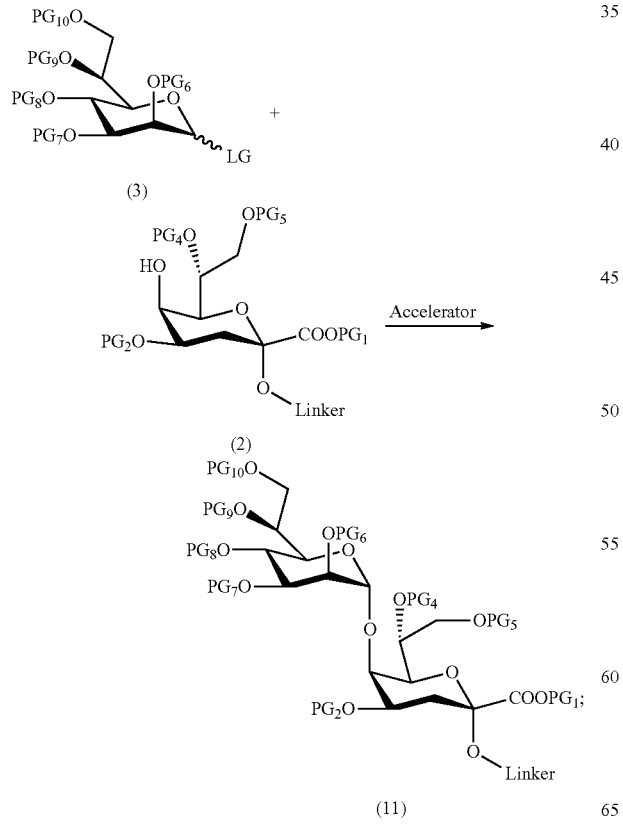

(b) removing the $PG_7$ protecting group of the disaccharide 11 selectively to prepare disaccharide 12; and performing a glycosylation reaction between the disaccharide 12 and a saccharide block donor formula 4 in the presence of an accelerator to prepare a trisaccharide compound 13 by the following synthesis route:

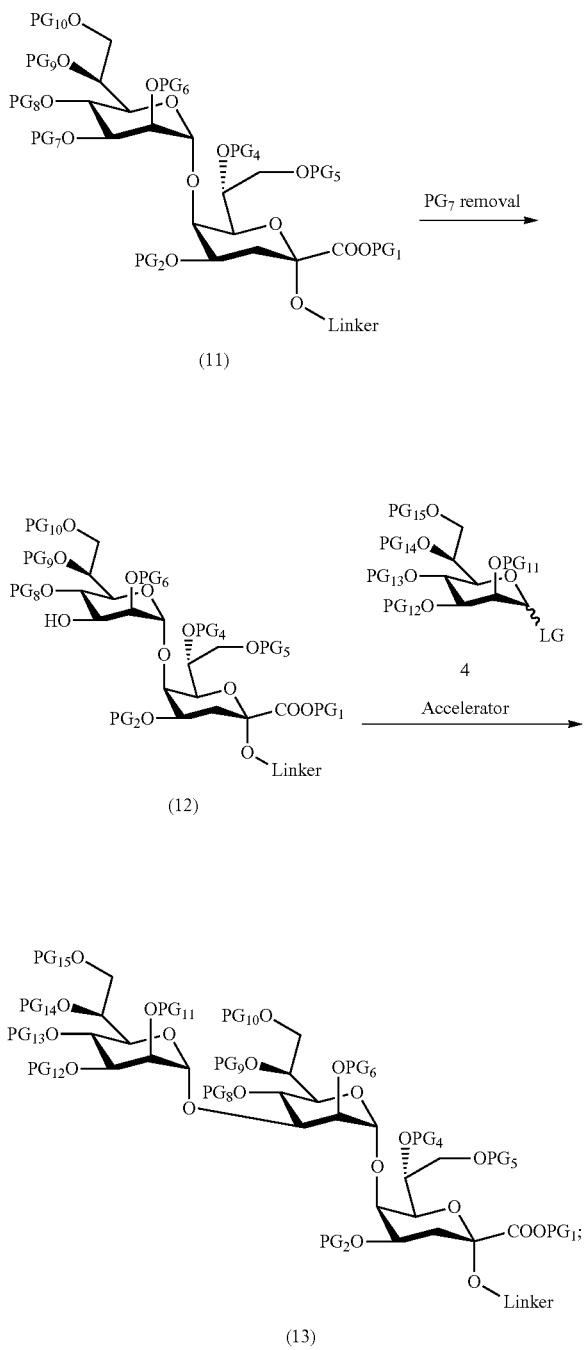

(c) removing the $PG_{11}$ protecting group of the trisaccharide compound 13 selectively to prepare trisaccharide 14; and performing a glycosylation reaction between the trisaccharide 14 and a saccharide block donor formula 5 in the presence of an accelerator to prepare a tetrasaccharide compound 15 by the following synthesis route:

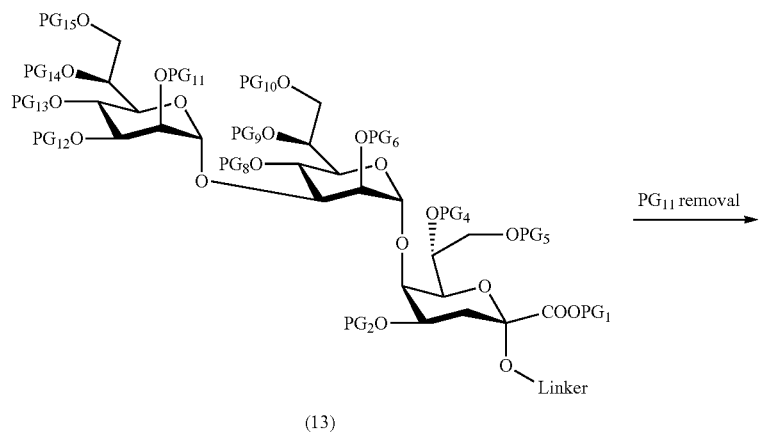
(13)
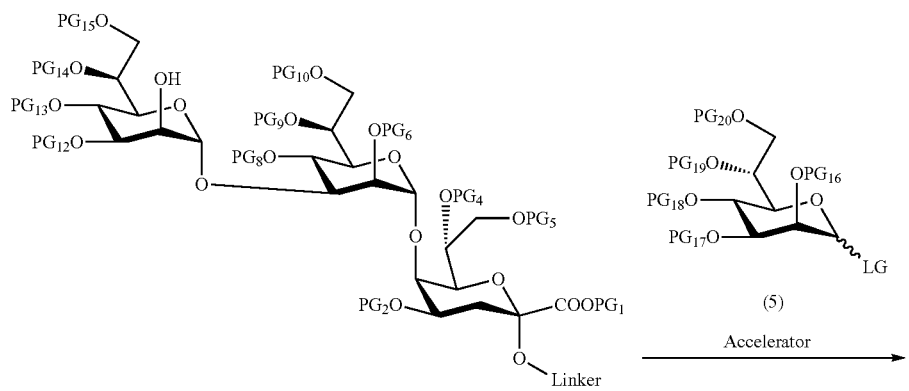
(14) (5)
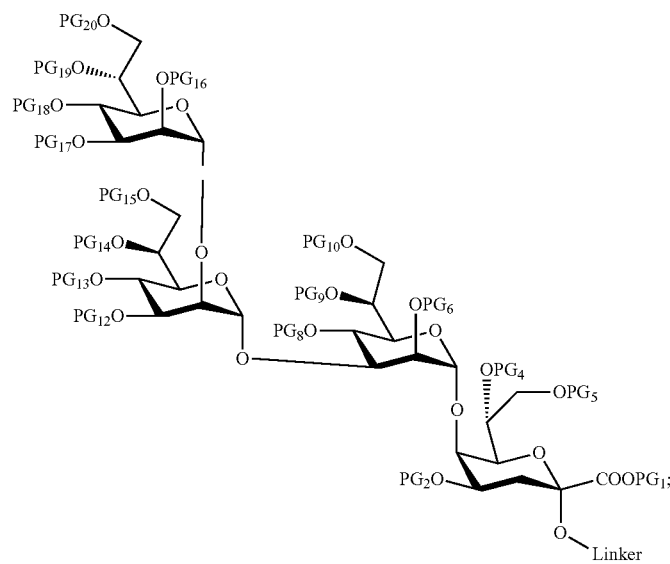
(15)

(d) removing the $PG_{16}$ protecting group of the tetrasaccharide 15 selectively to prepare tetrasaccharide 16; and performing a glycosylation reaction between the tetrasaccharide 16 and a saccharide block donor formula 6 in the presence of an accelerator to prepare a pentasaccharide compound 17 by the following synthesis route:
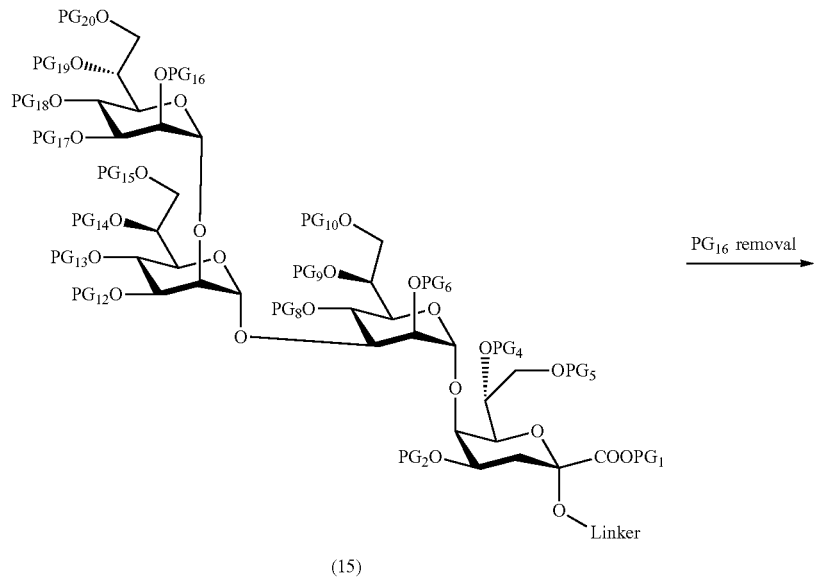
(15)
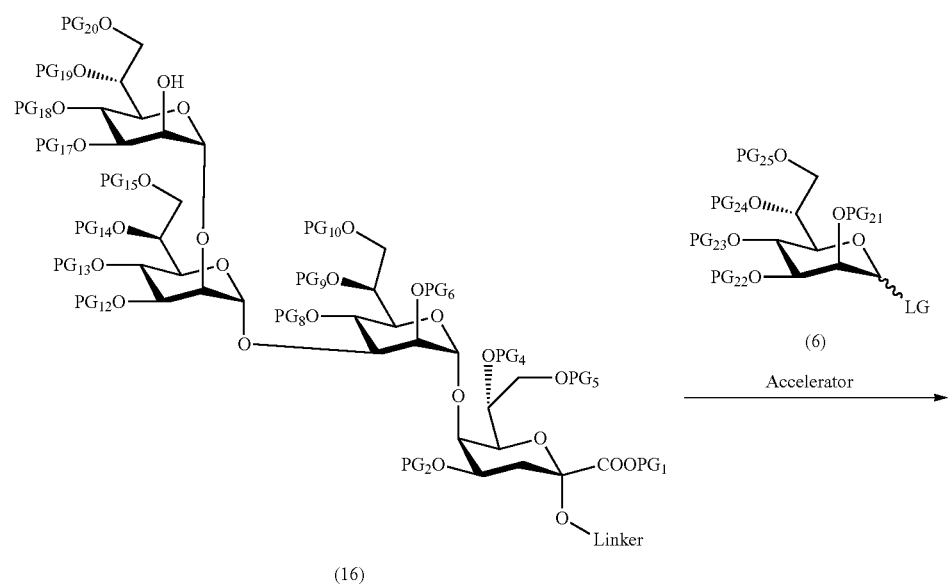
(16)            (6)
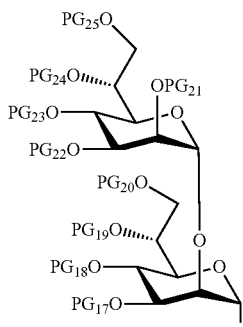

-continued

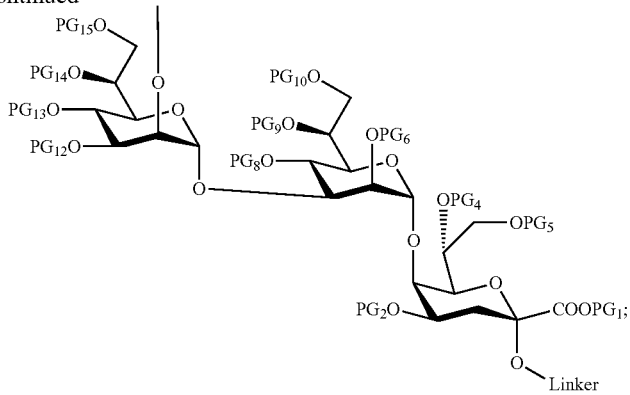

(17)

(e) performing a glycosylation reaction between a saccharide block donor formula 7 and a saccharide block receptor formula 9 under the catalysis of an accelerator to prepare disaccharide 18; and removing $PG_{29}$ of the disaccharide 18 selectively to prepare disaccharide 19 and further performing a glycosylation reaction between the disaccharide 19 and a saccharide block donor formula 7 under the catalysis of an accelerator to prepare a trisaccharide module 20; and after $R_{38}$ is removed, performing a reaction of the terminal hydroxyl with trichloroacetonitrile or phenyltrifluoroacetyl chloride under an alkaline catalyst to prepare a trisaccharide donor 21 by the following synthesis route:

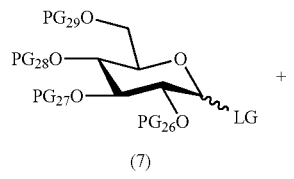

(7)

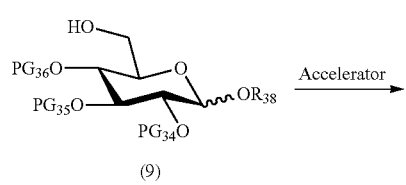

(9)

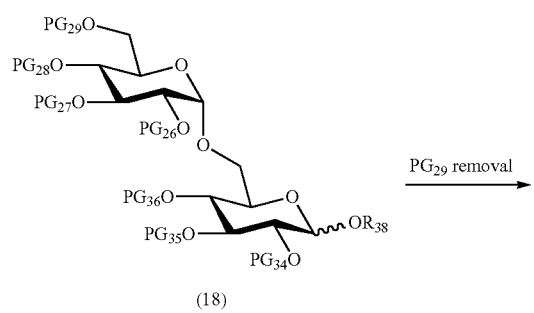

(18)

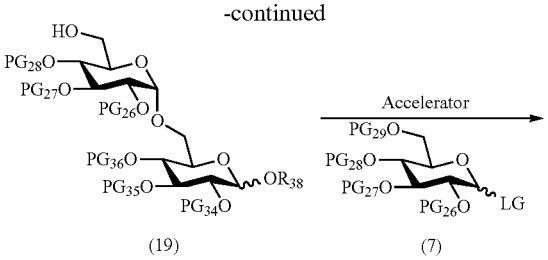

(19)         (7)

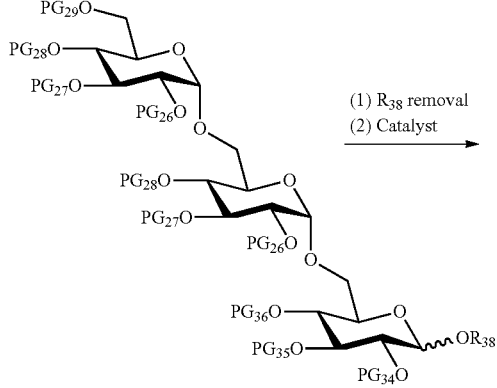

(20)

(21)

(f) removing the $PG_{21}$ protecting group of the pentasaccharide compound 17 selectively to prepare pentasaccharide 22; and performing a glycosylation reaction between the pentasaccharide 22 and a trisaccharide donor 21 in the presence of an accelerator to prepare an octasaccharide compound 23 by the following synthesis route:
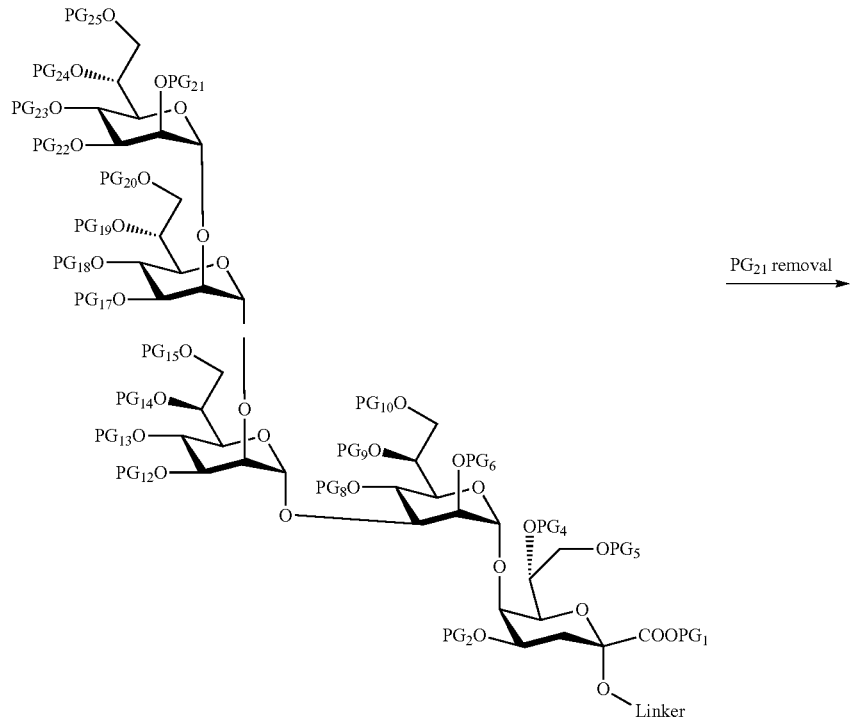
(17)
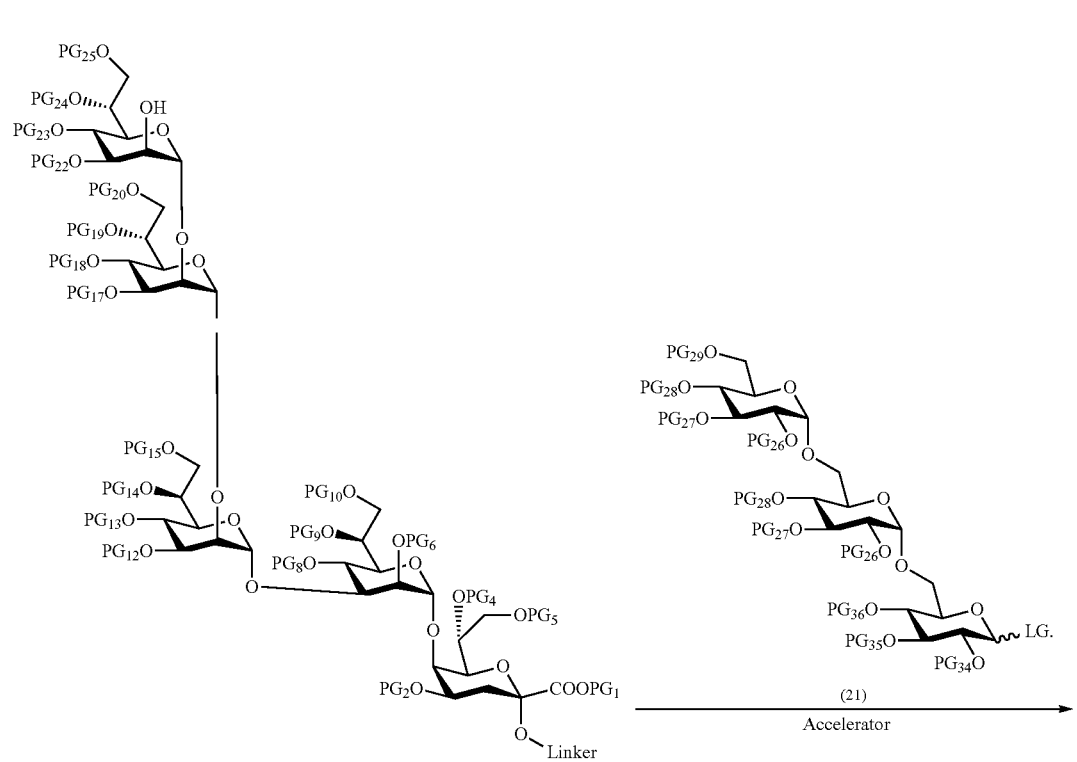
(22) (21)

-continued

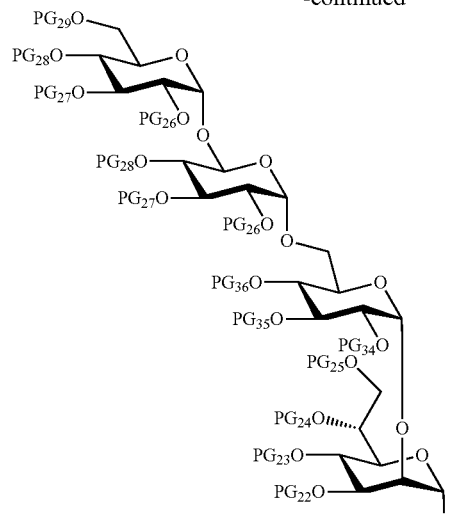

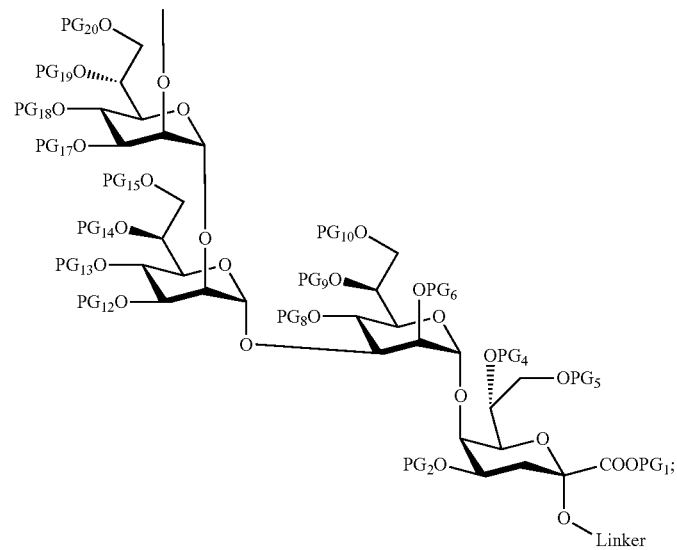

(23)

(g) performing a glycosylation reaction between a glycosyl donor formula 7 and a receptor formula 24 under the catalysis of an accelerator to prepare disaccharide 25; and removing $R_{38}$ of the disaccharide 25 selectively, and performing a reaction of the terminal hydroxyl with trichloroacetonitrile or phenyltrifluoroacetyl chloride under an alkaline catalyst to prepare a disaccharide receptor 26 by the following synthesis route:

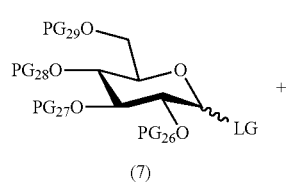

(7)

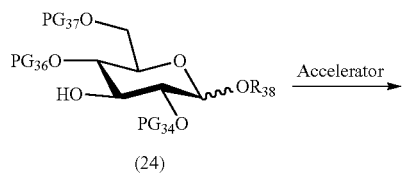

(24)

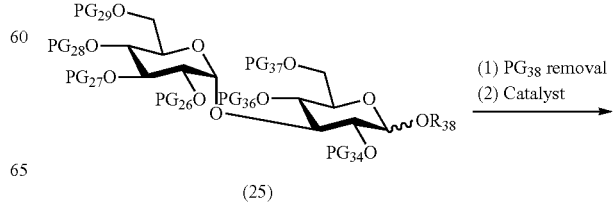

(25)

-continued

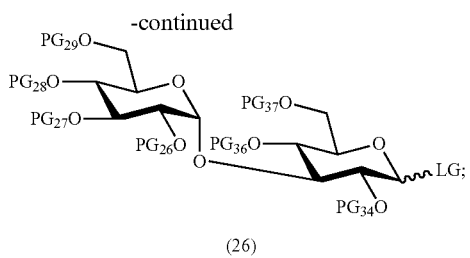

(26)

(h) removing the PG$_{20}$ protecting group of the octasaccharide 23 selectively to prepare octasaccharide 27; performing a glycosylation reaction between the octasaccharide 27 and a monosaccharide donor formula 8 under an accelerator to prepare a nonasaccharide compound 28; and removing the protecting group PG$_{32}$ of the nonasaccharide 28 selectively to prepare a nonasaccharide receptor 29, and performing a glycosylation reaction between the nonasaccharide receptor 29 and a glycosyl donor 26 under an accelerator to prepare undecasaccharide 30 by the following synthesis route:

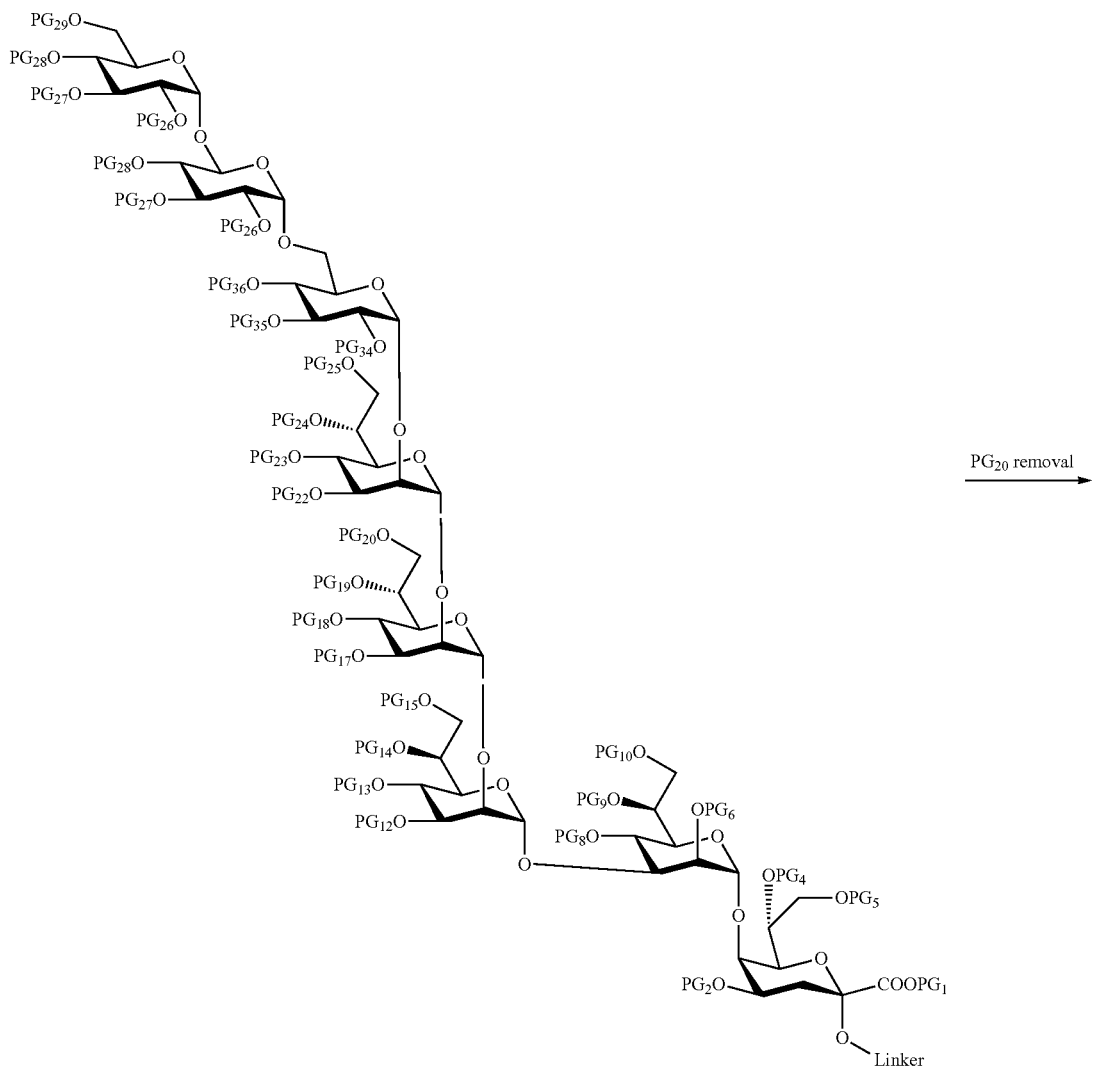

(23)

PG$_{20}$ removal →

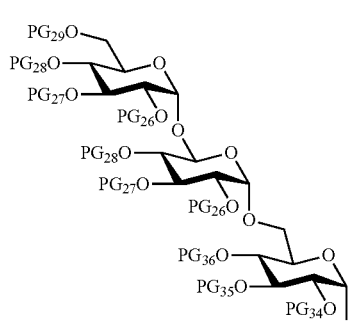

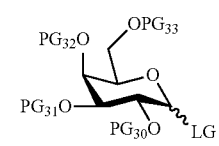

(8)

Accelerator →

-continued
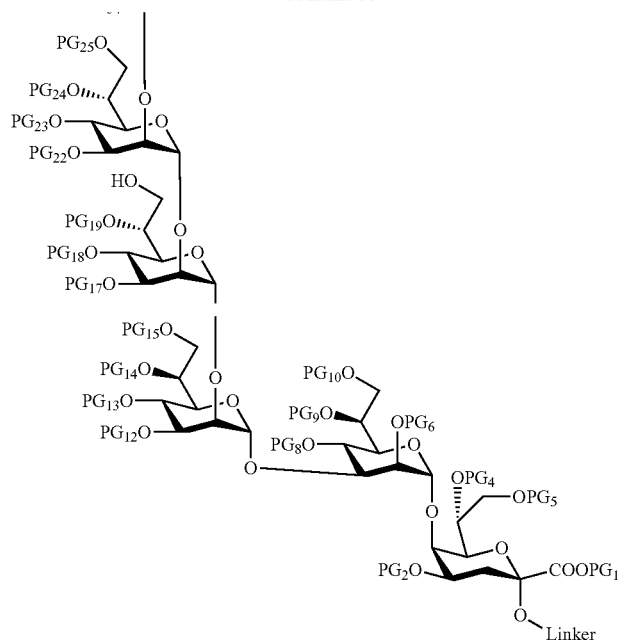
(27)
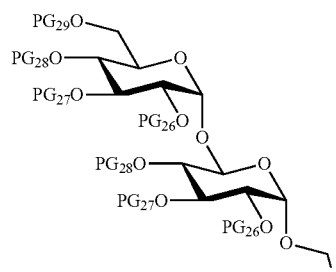
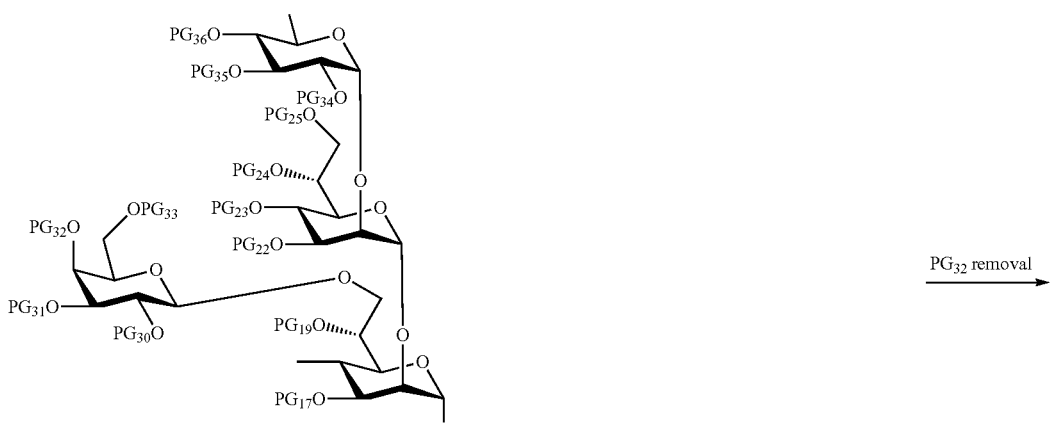
$PG_{32}$ removal
——————→

-continued
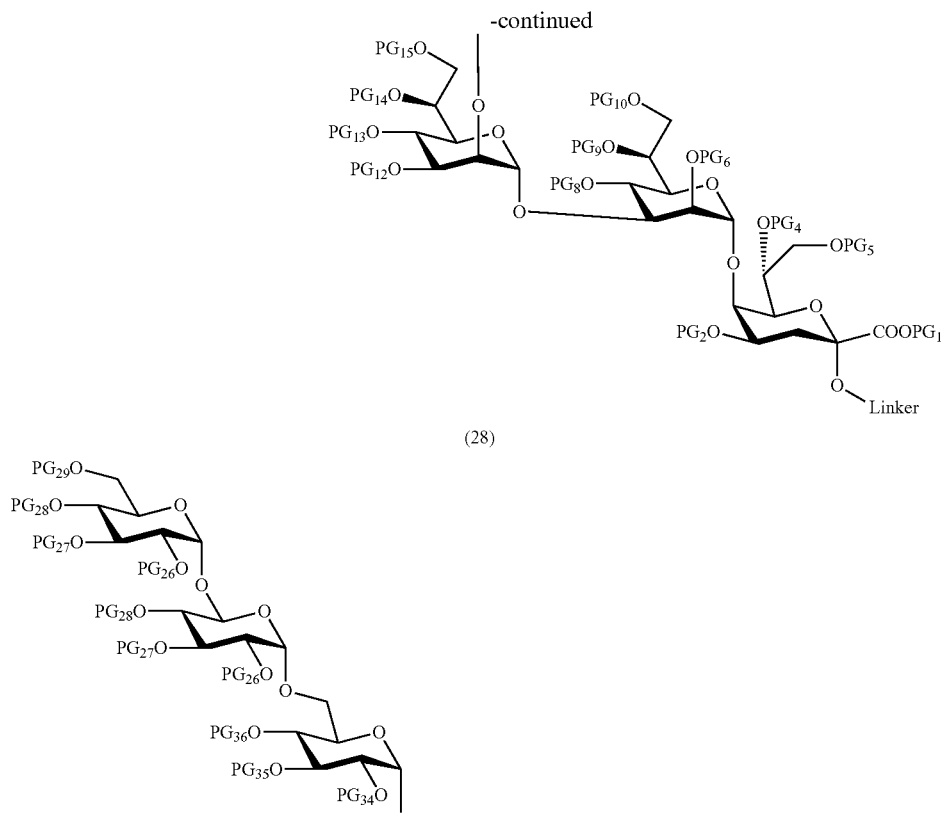
(28)
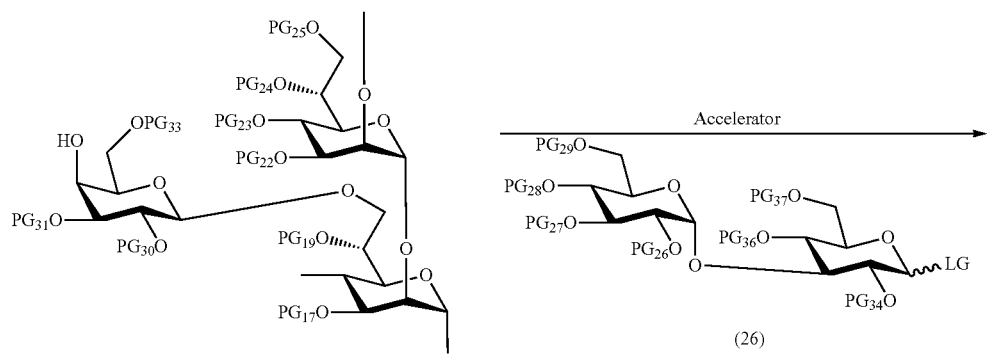
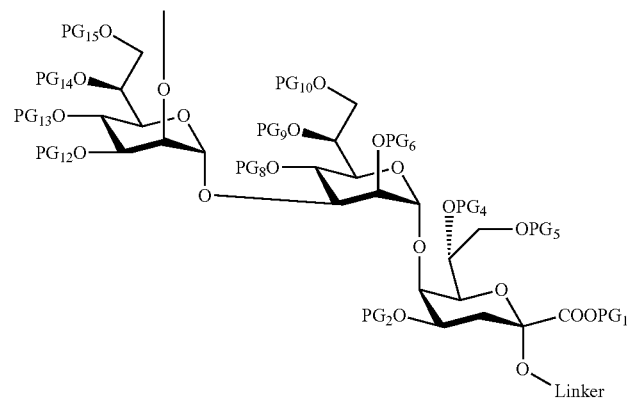
(29)

-continued
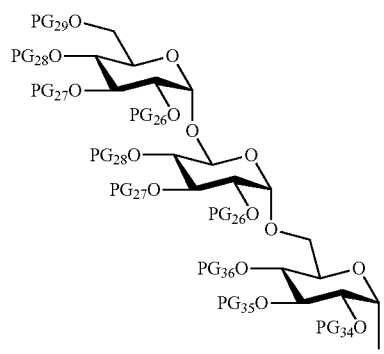
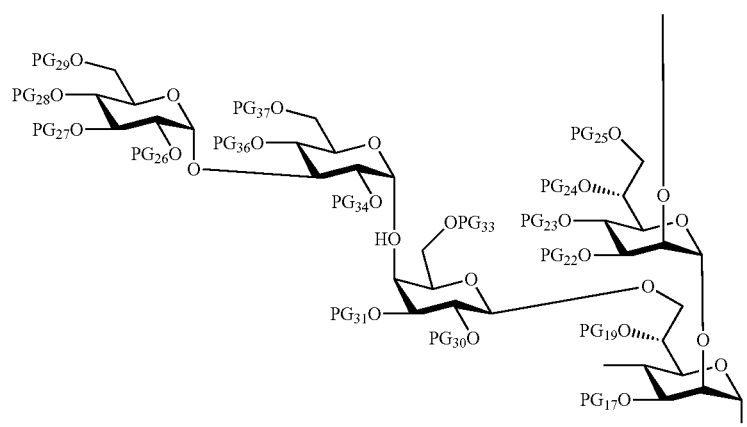
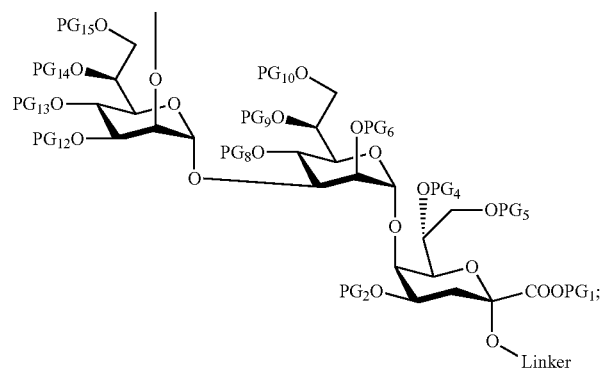
(30)

and
(i) removing an acyl protecting group of the undecasaccharide 30 under an alkaline conditions and an aromatic protecting of the undecasaccharide group under a palladium on carbon/hydrogen condition to complete deprotection, resulting in a completely deprotected *H. pylori* lipopolysaccharide core undecasaccharide antigen as shown in formula 1.

2. The method according to claim 1, wherein a molar ratio of the saccharide block donor formula 4 to the disaccharide 12 in step (b) is (1-2):1; and the glycosylation reaction is conducted at −10° C. to 0° C. for 3 hours to 7 hours by dissolving the glycosyl donor and the glycosyl receptor in dichloromethane, and adding molecular sieves and an activating reagent.

3. The method according to claim 1, wherein a molar ratio of the donor formula 5 to the trisaccharide 14 in step (c) is (1-2):1; and the glycosylation reaction is conducted at −20° C. to 0° C. for 3 hours to 7 hours by dissolving the glycosyl donor and the glycosyl receptor in dichloromethane, and adding molecular sieves and an activating reagent.

4. The method according to claim 1, wherein a molar ratio of the saccharide block donor formula 6 to the tetrasaccharide 16 in step (d) is (1-2):1; and the glycosylation reaction is conducted at −20° C. to 0° C. for 3 hours to 7 hours by dissolving the glycosyl donor and the glycosyl receptor in dichloromethane, and adding molecular sieves and an activating reagent.

5. The method according to claim 1, wherein a molar ratio of the trisaccharide donor formula 21 to the pentasaccharide 22 as receptor in step (f) is (1-2):1; and the glycosylation reaction is conducted at 0° C. to room temperature for 3 hours to 7 hours by dissolving the glycosyl donor and the glycosyl receptor in dichloromethane and ether (1:3), and adding molecular sieves and an activating reagent.

6. The method according to claim 1, wherein a molar ratio of the saccharide block donor to the receptor in step (h) is (2-5):1; and the glycosylation reaction is conducted at 0° C. to room temperature for 3 hours to 7 hours by dissolving the glycosyl donor and the glycosyl receptor in dichloromethane and ether (1:3), and adding molecular sieves and an activating reagent.

* * * * *